(12) United States Patent
Heron et al.

(10) Patent No.: US 7,528,121 B2
(45) Date of Patent: May 5, 2009

(54) PHOSPHONOOXY QUINAZOLINE DERIVATIVES AND THEIR PHARMACEUTICAL USE

(75) Inventors: Nicola Murdoch Heron, Macclesfield (GB); Andrew Austen Mortlock, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 620 days.

(21) Appl. No.: 10/539,220

(22) PCT Filed: Dec. 22, 2003

(86) PCT No.: PCT/GB03/05613

§ 371 (c)(1), (2), (4) Date: Jun. 17, 2005

(87) PCT Pub. No.: WO2004/058781

PCT Pub. Date: Jul. 15, 2004

(65) Prior Publication Data

US 2006/0116357 A1    Jun. 1, 2006

(30) Foreign Application Priority Data

Dec. 24, 2002  (EP) ................... 02293238
Jun. 2, 2003   (EP) ................... 03291315

(51) Int. Cl.
*A61K 31/53*   (2006.01)
*A61K 31/517*  (2006.01)
*A61K 31/675*  (2006.01)
*C07F 9/40*    (2006.01)
*C07D 239/94*  (2006.01)

(52) U.S. Cl. ................. 514/81; 514/266.2; 514/266.23; 544/244; 544/284

(58) Field of Classification Search ................... 514/81, 514/266.2, 266.23; 544/284, 244
See application file for complete search history.

(56) References Cited

U.S. PATENT DOCUMENTS

| 5,480,883 | A   | 1/1996 | Spada et al. |
| 5,710,158 | A   | 1/1998 | Myers et al. |
| 6,610,677 | B2  | 8/2003 | Davies et al. |
| 6,919,338 | B2* | 7/2005 | Mortlock et al. ......... 514/234.5 |
| 7,214,518 | B2* | 5/2007 | Anderson et al. ........... 435/183 |

FOREIGN PATENT DOCUMENTS

| EP | 03/26330 | B1 | 7/2002 |
| WO | 92/20642 | A1 | 11/1992 |
| WO | 95/15758 | A1 | 6/1995 |
| WO | 96/09294 | A1 | 3/1996 |
| WO | 96/15118 | A1 | 5/1996 |
| WO | 96/39145 | A1 | 12/1996 |
| WO | 97/03069 | A1 | 1/1997 |
| WO | 99/06378 | A1 | 2/1999 |
| WO | 00-21955 | * | 4/2000 |
| WO | 00/21955 | A1 | 4/2000 |
| WO | WO 01/21596 | A1 | 3/2001 |
| WO | WO 01/21597 | A1 | 3/2001 |
| WO | WO 02/00649 | A1 | 1/2002 |
| WO | WO 03/000188 | A2 | 1/2003 |
| WO | WO 03/055491 | A1 | 7/2003 |

OTHER PUBLICATIONS

Voskoglou-Nomikos, T. et. al., "Clinical Predictive Value of the in Vitro Cell Line, . . . " Clinical Cancer Research, Sep. 2003, vol. 9, pp. 4227-4239.*
Mortlock, A.A. et. al., "Discovery, Synthesis, and in Vivo Activity of a New Class of Pyrazoloquinazolines as Selective Inhibitors of Auroro B Kinase", 2007, vol. 50, pp. 2213-2224.*
Heron et al., "SAR and inhibitor complex structure determination of a novel class of potent and specific Aurora kinase inhibitors". Bioorganic & Medicinal Chemistry Letters (2006), 1320-1323, 16(5).
Jung et al., "Discovery of Novel and Potent Thiazoloquinazolines as Selective Aurora A and B Kinase Inhibitors". Journal of Medicinal Chemistry (2006), 955-970, 49(3).
Mortlock et al., "Discovery, Synthesis, and in Vivo Activity of a New Class of Pyrazoloquinazolines as Selective Inhibitors of Aurora B Kinase". Journal of Medicinal Chemistry (2007), 2213-2224, 50(9).
Mortlock et al., "Progress in the Development of Selective Inhibitors of Aurora Kinases". Current Topics in Medicinal Chemistry (2005), 807-821, 5(8).
Wilkinson et al., "AZD1152, a Selective Inhibitor of Aurora B Kinase, Inhibits Human Tumor Xenograft Growth by Inducing Apoptosis", Clinical Cancer Research (2007), 3682-3688, 13(12).

* cited by examiner

*Primary Examiner*—James O Wilson
*Assistant Examiner*—Tamthom N Truong

(57) ABSTRACT

Quinazoline derivatives of formula (I) wherein A is 5-membered heteroaryl containing a nitrogen atom and one or two further nitrogen atoms; compositions containing them, processes for their preparation and their use in therapy.

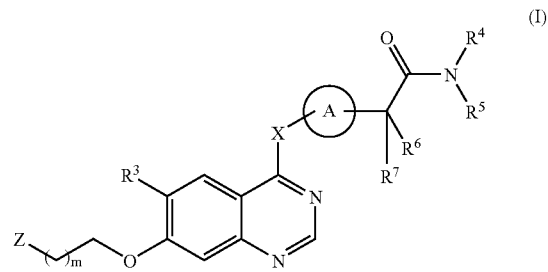

2 Claims, No Drawings

PHOSPHONOOXY QUINAZOLINE DERIVATIVES AND THEIR PHARMACEUTICAL USE

CROSS-REFERENCE TO RELATED APPLICATIONS

This application is a US National Stage under 35 U.S.C § 371 of International Application No. PCT/GB2003/005613 (filed Dec. 22, 2003) which claims priority under 35 U.S.C. § 119(a)-(d) to Application No. EP 02293238.8 filed on Dec. 24, 2002 and to Application No. EP 03291315.4 filed on Jun. 2, 2003.

The present invention relates to certain quinazoline derivatives for use in the treatment of certain diseases in particular to proliferative disease such as cancer and in the preparation of medicaments for use in the treatment of proliferative disease, to novel quinazoline compounds and to processes for their preparation, as well as pharmaceutical compositions containing them as active ingredient.

Cancer (and other hyperproliferative disease) is characterised by uncontrolled cellular proliferation. This loss of the normal regulation of cell proliferation often appears to occur as the result of genetic damage to cellular pathways that control progress through the cell cycle.

In eukaryotes, an ordered cascade of protein phosphorylation is thought to control the cell cycle. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co activators or inhibitory proteins.

The first identified, and most widely studied of these cell cycle regulators have been the cyclin dependent kinases (or CDKs). Activity of specific CDKs at specific times is essential for both initiation and coordinated progress through the cell cycle. For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D. One of the first demonstrations of a direct link between cancer and the cell cycle was made with the observation that the Cyclin D1 gene was amplified and cyclin D protein levels increased (and hence the activity of CDK4 increased) in many human tumours (Reviewed in Sherr, 1996, Science 274: 1672-1677; Pines, 1995, Seminars in Cancer Biology 6: 63-72). Other studies (Loda et al., 1997, Nature Medicine 3(2): 231-234; Gemma et al., 1996, International Journal of Cancer 68(5): 605-11; Elledge et al. 1996, Trends in Cell Biology 6; 388-392) have shown that negative regulators of CDK function are frequently down regulated or deleted in human tumours again leading to inappropriate activation of these kinases.

More recently, protein kinases that are structurally distinct from the CDK family have been identified which play critical roles in regulating the cell cycle and which also appear to be important in oncogenesis. These include the newly identified human homologues of the *Drosophila* aurora and *S. cerevisiae* Ip11 proteins. The three human homologues of these genes Aurora-A, Aurora-B and Aurora-C (also known as aurora2, aurora1 and aurora3 respectively) encode cell cycle regulated serine-threonine protein kinases (summarised in Adams et al., 2001, Trends in Cell Biology. 11(2): 49-54). These show a peak of expression and kinase activity through G2 and mitosis. Several observations implicate the involvement of human aurora proteins in cancer. The Aurora-A gene maps to chromosome 20q13, a region that is frequently amplified in human tumours including both breast and colon tumours. Aurora-A may be the major target gene of this amplicon, since Aurora-A DNA is amplified and mRNA over-expressed in greater than 50% of primary human colorectal cancers. In these tumours Aurora-A protein levels appear greatly elevated compared to adjacent normal tissue. In addition, transfection of rodent fibroblasts with human Aurora-A leads to transformation, conferring the ability to grow in soft agar and form tumours in nude mice (Bischoff et al., 1998, The EMBO Journal. 17(11): 3052-3065). Other work (Zhou et al., 1998, Nature Genetics. 20(2): 189-93) has shown that artificial overexpression of Aurora-A leads to an increase in centrosome number and an increase in aneuploidy, a known event in the development of cancer. Further work has shown an increase in expression of Aurora-B (Adams et al., 2001, Chromsoma. 110(2):65-74) and Aurora-C (Kimura et al., 1999, Journal of Biological Chemistry, 274(11): 7334-40) in tumour cells when compared to normal cells.

Importantly, it has also been demonstrated that abrogation of Aurora-A expression and function by antisense oligonucleotide treatment of human tumour cell lines (WO 97/22702 and WO 99/37788) leads to cell cycle arrest and exerts an antiproliferative effect in these tumour cell lines. Additionally, small molecule inhibitors of Aurora-A and Aurora-B have been demonstrated to have an antiproliferative effect in human tumour cells (Keen et al. 2001, Poster #2455, American Association of Cancer research annual meeting), as has selective abrogation of Aurora-B expression alone by siRNA treatment (Ditchfield et al. 2003, journal of Cell Biology, 161(2): 267-280). This indicates that inhibition of the function of Aurora-A and/or Aurora-B will have an antiproliferative effect that may be useful in the treatment of human tumours and other hyperproliferative disease. Further, inhibition of Aurora kinases as a therapeutic approach to these diseases may have significant advantages over targeting signalling pathways upstream of the cell cycle (e.g. those activated by growth factor receptor tyrosine kinases such as epidermal growth factor receptor (EGFR) or other receptors). Since the cell cycle is ultimately downstream of all of these diverse signalling events, cell cycle directed therapies such as inhibition of Aurora kinases would be predicted to be active across all proliferating tumour cells, whilst approaches directed at specific signalling molecules (e.g. EGFR) would be predicted to be active only in the subset of tumour cells which express those receptors. It is also believed that significant "cross talk" exists between these signalling pathways meaning that inhibition of one component may be compensated for by another.

A number of quinazoline derivatives have been proposed hitherto for use in the inhibition of various kinases. For example, WO 96/09294, WO 96/15118 and WO 99/06378 describe the use of certain quinazoline compounds as receptor tyrosine kinase inhibitors, which may be useful in the treatment of proliferative disease and WO 00/21955 discloses certain quinazoline derivatives as inhibitors of the effects of VEGF.

Quinazoline derivatives have also been disclosed for use in the inhibition of Aurora-A kinase. WO 02/00649 discloses quinazoline derivative bearing a 5-membered heteroaromatic ring where the ring is, in particular, substituted thiazole or substituted thiophene and co-pending patent application WO 03/055491 discloses quinazoline derivatives bearing an optionally substituted pyrazole ring. However despite the compounds of WO 02/00649 and WO 03/055491 there still exists the need for further compounds having Aurora kinase inhibitory properties.

The applicants have been successful in finding a novel series of compounds which inhibit the effects of the Aurora kinases and in particular Aurora-A and/or Aurora-B kinase and which have certain properties that make them particularly useful in formulating medicaments for the treatment of disease. In particular the compounds are of use in the treatment of proliferative disease such as cancer occurring as either solid and haematological tumours where Aurora kinases are known to be active, and especially in diseases such as colorectal, breast, lung, prostate, pancreatic or bladder and renal cancer as well as leukaemias and lymphomas.

According to one aspect of the present invention there is provided a compound of formula (I):

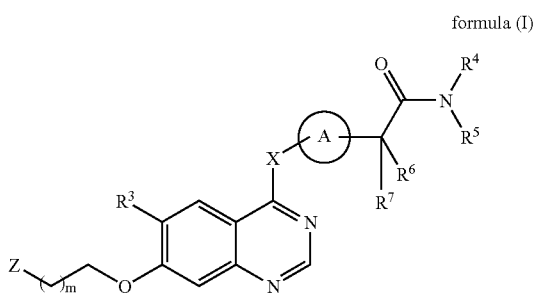

formula (I)

wherein A is 5-membered heteroaryl containing a nitrogen atom and optionally containing one or two further nitrogen atoms;

X is O, S, S(O), S(O)$_2$ or NR$^{14}$;

m is 0, 1, 2 or 3;

Z is a group selected from —NR$^1$R$^2$, phosphonooxy, C$_{3-6}$cycloalkyl which C$_{3-6}$cycloalkyl is substituted by phosphonooxy or C$_{1-4}$alkyl substituted by phosphonooxy, and a 4- to 7-membered ring linked via a carbon atom containing a nitrogen atom and optionally containing a further nitrogen atom, which ring may be saturated, partially saturated or unsaturated wherein the ring is substituted on carbon or nitrogen by phosphonooxy or C$_{1-4}$alkyl substituted by phosphonooxy, and wherein the ring is optionally further substituted on carbon or nitrogen by 1, 2 or 3 halo or C$_{1-4}$alkyl groups;

R$^1$ is a group selected from —COR$^8$, —CONR$^8$R$^9$ and C$_{1-6}$alkyl which C$_{1-6}$alkyl is substituted by phosphonooxy and optionally further substituted by 1 or 2 halo or methoxy groups;

R$^2$ is a group selected from hydrogen, —COR$^{10}$, —CONR$^{10}$R$^{11}$ and C$_{1-6}$alkyl which C$_{1-6}$alkyl is optionally substituted by 1, 2 or 3 halo or C$_{1-4}$alkoxy groups, —S(O)$_p$R$^{11}$ (where p is 0, 1 or 2) or phosphonooxy, or R$^2$ is a group selected from C$_{2-6}$alkenyl, C$_{2-6}$alkynyl, C$_{3-6}$cycloalkyl and C$_{3-6}$cycloalkylC$_{1-4}$alkyl;

or R$^1$ and R$^2$ together with the nitrogen to which they are attached form a 4- to 7-membered ring optionally containing a further nitrogen atom which ring may be saturated, unsaturated or partially saturated, wherein the ring is substituted on carbon or nitrogen by a group selected from phosphonooxy and C$_{1-4}$alkyl which C$_{1-4}$alkyl is substituted by phosphonooxy or —NR$^8$R$^9$, and where the ring is optionally further substituted on carbon or nitrogen by 1, 2 or 3 halo or C$_{1-4}$alkyl groups;

R$^3$ is a group selected from hydrogen, halo, cyano, nitro, C$_{1-6}$alkoxy, C$_{1-6}$alkyl, —OR$^{12}$, —CHR$^{12}$R$^{13}$, —OC(O)R$^{12}$, —C(O)R$^{12}$, —NR$^{12}$C(O)R$^{13}$, —C(O)NR$^{12}$R$^{13}$, —NR$^{12}$SO$_2$R$^{13}$ and —NR$^{12}$R$^{13}$;

R$^4$ is hydrogen or a group selected from C$_{1-4}$alkyl, heteroaryl, heteroarylC$_{1-4}$alkyl, aryl and arylC$_{1-4}$alkyl which group is optionally substituted by 1, 2 or 3 substitutents selected from halo, methyl, ethyl, cyclopropyl and ethynyl;

R$^5$ is selected from hydrogen, C$_{1-4}$alkyl, C$_{2-4}$alkenyl, C$_{2-4}$alkynyl, C$_{3-6}$cycloalkyl and C$_{3-6}$cycloalkylC$_{1-4}$alkyl;

R$^6$ and R$^7$ are independently selected from hydrogen, halo, C$_{1-4}$alkyl, C$_{3-6}$cycloalkyl, hydroxy and C$_{1-4}$alkoxy;

R$^8$ is C$_{1-4}$alkyl substituted by phosphonooxy and optionally further substituted by 1 or 2 halo or methoxy groups;

R$^9$ is selected from hydrogen and C$_{1-4}$alkyl;

R$^{10}$ is selected from hydrogen and C$_{1-4}$alkyl optionally substituted by halo, C$_{1-4}$alkoxy, S(O)$_q$ (where q is 0, 1 or 2) or phosphonoxy;

R$^{11}$, R$^{12}$, R$^{13}$ and R$^{14}$ are independently selected from hydrogen, C$_{1-4}$alkyl and heterocyclyl; or a pharmaceutically acceptable salt thereof.

Within the present invention, it is to be understood that, insofar as certain compounds of formula (I) herein defined may exist in optically active or racemic forms by virtue of one or more asymmetric carbon or sulphur atoms, the invention includes in its definition any such optically active or racemic form which possesses Aurora kinase inhibitory activity and in particular Aurora-A and/or Aurora-B kinase inhibitory activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of formula (I) or a salt thereof may exhibit the phenomenon of tautomerism and that the formulae drawings within this specification can represent only one of the possible tautomeric forms. It is to be understood that the invention encompasses any tautomeric form which has Aurora kinase inhibitory activity and in particular Aurora-A and/or Aurora-B kinase inhibitory activity and is not to be limited merely to any one tautomeric form utilised within the formulae drawings.

It is also to be understood that certain compounds of formula (I) and salts thereof can exist in solvated as well as unsolvated forms such as, for example, hydrated forms. It is to be understood that the invention encompasses all such solvated forms which have Aurora kinase inhibitory activity and in particular Aurora-A and/or Aurora-B kinase inhibitory activity.

The present invention relates to the compounds of formula (I) as herein defined as well as to the salts thereof. Salts for use in pharmaceutical compositions will be pharmaceutically acceptable salts, but other salts may be useful in the production of the compounds of formula (I) and their pharmaceutically acceptable salts. Pharmaceutically acceptable salts of the invention may, for example, include acid addition salts of compounds of formula (I) as herein defined which are sufficiently basic to form such salts. Such acid addition salts include but are not limited to fumarate, methanesulphonate, hydrochloride, hydrobromide, citrate and maleate salts and salts formed with phosphoric and sulphuric acid. In addition where compounds of formula (I) are sufficiently acidic, salts are base salts and examples include but are not limited to, an alkali metal salt for example sodium or potassium, an alkaline earth metal salt for example calcium or magnesium, or organic amine salt for example triethylamine, ethanolamine, diethanolamine, triethanolamine, morpholine, N-methylpiperidine, N-ethylpiperidine, dibenzylamine or amino acids such as lysine.

The compounds of formula (I) may also be provided as in vivo hydrolysable esters. An in vivo hydrolysable ester of a compound of formula (I) containing carboxy or hydroxy group is, for example a pharmaceutically acceptable ester which is cleaved in the human or animal body to produce the parent acid or alcohol. Such esters can be identified by administering, for example, intravenously to a test animal, the compound under test and subsequently examining the test animal's body fluid.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl, 1,3-dioxolen-2-onylmethyl esters for example 5-methyl-1,3-dioxolen-2-onylmethyl, and $C_{1-6}$alkoxycarbonyloxyethyl esters for example 1-methoxycarbonyloxyethyl; and may be formed at any carboxy group in the compounds of this invention.

Suitable pharmaceutically acceptable esters for hydroxy include inorganic esters such as phosphate esters (including phosphoramidic cyclic esters) and α-acyloxyalkyl ethers and related compounds which as a result of the in vivo hydrolysis of the ester breakdown to give the parent hydroxy group/s. Examples of α-acyloxyalkyl ethers include acetoxymethoxy and 2,2-dimethylpropionyloxymethoxy. A selection of in vivo hydrolysable ester forming groups for hydroxy include $C_{1-10}$alkanoyl, for example formyl, acetyl, benzoyl, phenylacetyl, substituted benzoyl and phenylacetyl; $C_{1-10}$alkoxycarbonyl (to give alkyl carbonate esters), for example ethoxycarbonyl; di-$C_{1-4}$alkylcarbamoyl and N-(di-$C_{1-4}$ alkylaminoethyl)-N-$C_{1-4}$alkylcarbamoyl (to give carbamates); di-$C_{1-4}$alkylaminoacetyl and carboxyacetyl. Examples of ring substituents on phenylacetyl and benzoyl include aminomethyl, $C_{1-4}$alkylaminomethyl and di-($C_{1-4}$alkyl)aminomethyl, and morpholino or piperazino linked from a ring nitrogen atom via a methylene linking group to the 3- or 4-position of the benzoyl ring. Other interesting in vivo hydrolysable esters include, for example, $R^4C(O)OC_{1-6}$ alkyl-CO—, wherein $R^4$ is for example, benzyloxy-$C_{1-4}$ alkyl, or phenyl. Suitable substituents on a phenyl group in such esters include, for example, 4-$C_{1-4}$piperazino-$C_{1-4}$alkyl, piperazino-$C_{1-4}$ alkyl and morpholino-$C_{1-4}$alkyl.

In this specification the generic term "alkyl" includes both straight-chain and branched-chain alkyl groups. However references to individual alkyl groups such as "propyl" are specific for the straight chain version only and references to individual branched-chain alkyl groups such as "tert-butyl" are specific for the branched chain version only. An analogous convention applies to other generic terms, for example "alkenyl" and "alkynyl".

"Cycloalkyl" is a monocyclic, saturated alkyl ring and "aryl" is a monocyclic or bicyclic aromatic ring.

Unless otherwise specified "heteroaryl" is a monocyclic or bicyclic aromatic ring containing 5 to 10 ring atoms of which 1, 2, 3 or 4 ring atoms are chosen from nitrogen, sulphur or oxygen where a ring nitrogen or sulphur may be oxidised.

"Heterocyclyl" is a saturated, unsaturated or partially saturated monocyclic or bicyclic ring containing 4 to 12 atoms of which 1, 2, 3 or 4 ring atoms are chosen from nitrogen, sulphur or oxygen, which ring may be carbon or nitrogen linked, wherein a —$CH_2$— group can optionally be replaced by a —C(O)—; wherein a ring nitrogen or sulphur atom is optionally oxidised to form the N-oxide or S-oxide(s); wherein a ring —NH is optionally substituted by acetyl, formyl, methyl or mesyl; and wherein a ring is optionally substituted by one or more halo.

"Phosphonooxy" is in one aspect a group of formula —OP(O)(OH)$_2$. However the term "phosphonooxy" also includes salts of this group such as those formed with alkali metal ions such as sodium or potassium ions or alkaline earth metal ions, for example calcium or magnesium ions.

Where optional substituents are chosen from "1 or 2", from "1,2, or 3" or from "1, 2, 3 or 4" groups or substituents it is to be understood that this definition includes all substituents being chosen from one of the specified groups i.e. all substitutents being the same or the substituents being chosen from two or more of the specified groups i.e. the substitutents not being the same.

Compounds of the present invention have been named with the aid of computer software (ACD/Name version 6.6 or ACD Name Batch version 6.0).

Suitable values for any R group ($R^1$ to $R^{14}$) or any part or substitutent for such groups include:

for $C_{1-4}$alkyl: methyl, ethyl, propyl, isopropyl, butyl, 2-methylpropyl and tert-butyl;

for $C_{1-6}$alkyl: $C_{1-4}$alkyl, pentyl, 2,2-dimethylpropyl, 3-methylbutyl and hexyl;

for $C_{2-4}$alkenyl: vinyl, allyl and 1-propenyl;

for $C_{2-6}$alkenyl: $C_{2-4}$alkenyl, 1-butenyl, 2-butenyl, 3-butenyl, 2-methylbut-2-enyl, 3-methylbut-1-enyl, 1-pentenyl, 3-pentenyl and 4-hexenyl;

for $C_{2-4}$alkynyl: ethynyl, 1-propynyl, 2-propynyl and 3-butynyl;

for $C_{2-6}$alkynyl: $C_{2-4}$alkynyl, 2-pentynyl, hexynyl and 1-methylpent-2-ynyl;

for $C_{3-6}$cycloalkyl: cyclopropyl, cyclobutyl, cyclopentyl and cyclohexyl;

for $C_{3-6}$cycloalkyl$C_{1-4}$alkyl: cyclopropylmethyl, cyclopropylethyl, cyclobutylmethyl, cyclopentylmethyl and cyclohexylmethyl;

for aryl: phenyl and naphthyl;

for aryl$C_{1-4}$alkyl: benzyl, phenethyl, naphthylmethyl and naphthylethyl;

for halo: fluoro, chloro, bromo and iodo;

for $C_{1-4}$alkoxy: methoxy, ethoxy, propoxy and isopropoxy;

for $C_{1-6}$alkoxy: $C_{1-4}$alkoxy, pentyloxy, 1-ethylpropoxy and hexyloxy;

for heteroaryl: pyridyl, imidazolyl, quinolinyl, cinnolyl, pyrimidinyl, thiophenyl, pyrrolyl, pyrazolyl, thiazolyl, triazolyl, oxazolyl, isoxazolyl and pyrazinyl and preferably thiazolyl, pyridyl, imidazolyl and pyrimidinyl;

for heteroaryl$C_{1-4}$alkyl: pyridylmethyl, pyridylethyl, pyrimidinylethyl, pyrimidinylpropyl, pyrimidinylbutyl, imidazolylpropyl, imidazolylbutyl, quinolinylpropyl, 1,3,4-triazolylpropyl and oxazolylmethyl;

for heterocyclyl: furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl, benzofuryl, piperidinyl, N-acetylpiperidinyl, N-methylpiperidinyl, N-formylpiperazinyl, N-mesylpiperazinyl, homopiperazinyl, piperazinyl, azetidinyl, oxetanyl, morpholinyl, tetrahydroisoquinolinyl, tetrahydroquinolinyl, indolinyl, pyranyl, dihydro-2H-pyranyl, tetrahydrofuranyl, 2,5-dioximidazolidinyl, 2,2-dimethyl-1,3-dioxolanyl and 3,4-dimethylenedioxybenzyl.

It should be noted that examples given for terms used in the description are not limiting.

Preferred values of A, X, m, Z, $R^3$, $R^4$, $R^5$, $R^6$ and $R^7$ are as follows. Such values may be used where appropriate with any of the definitions, claims or embodiments defined herein.

In one aspect of the invention A is pyrrolyl, pyrazolyl, imidazolyl or triazolyl. In a further aspect A is a group of formula (a), (b), (c), (d) or (e):

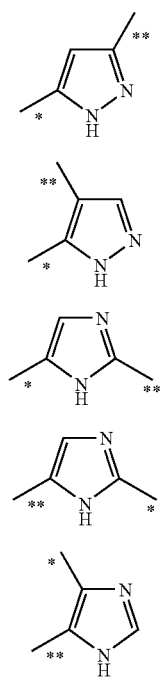

where * is the point of attachment to the X group of formula (I) and ** is the point of attachment to the $(CR^6R^7)$ group of formula (I). In a preferred aspect A is pyrazolyl. In a more preferred aspect A is a group of formula (a) as defined above.

In one aspect of the invention X is $NR^{14}$, O or S. In another aspect X is $NR^{14}$. In yet another aspect X is NH.

In one aspect of the invention m is 1, 2 or 3. In one aspect m is 1 or 2. In another aspect m is 0, 2 or 3. In another aspect m is 0, 1 or 2. In yet another aspect m is 1. In a further aspect m is 2.

In one aspect of the invention Z is —$NR^1R^2$ or a 5- to 6-membered saturated ring linked via a carbon atom containing a nitrogen atom and optionally containing a further nitrogen atom, which ring is substituted on carbon or nitrogen by phosphonooxy or $C_{1-4}$alkyl substituted by phosphonooxy. In another aspect Z is —$NR^1R^2$.

In one aspect of the invention $R^1$ is $C_{1-5}$alkyl substituted by phosphonooxy. In another aspect $R^1$ is $C_{1-5}$alkyl substituted by phosphonooxy and further substituted by 1 or 2 halo. In a further aspect $R^1$ is 2-phosphonooxyethyl, 2-phosphonooxy-1,1-dimethylethyl, 2-phosphonooxy-2-methylethyl, 3-phosphonooxy-1,1-dimethylpropyl, 3-phosphonooxypropyl and 4-phosphonooxybutyl. In yet another aspect $R^1$ is 2-phosphonooxyethyl, 2-phosphonooxy-1,1-dimethylethyl, 3-phosphonooxy-1,1-dimethylpropyl or 3-phosphonooxypropyl. In yet another aspect $R^1$ is 2-phosphonooxyethyl.

In one aspect of the invention $R^2$ is selected from hydrogen and $C_{1-6}$alkyl which $C_{1-6}$alkyl is optionally substituted by 1, 2 or 3 halo or $C_{1-4}$alkoxy groups, or $R^2$ is selected from $C_{2-6}$alkenyl, $C_{2-6}$alkynyl, $C_{3-6}$cycloalkyl and $C_{3-6}$cycloalkyl$C_{1-4}$alkyl. In another aspect $R^2$ is hydrogen, allyl, 2-propynyl, methyl, ethyl, propyl, isopropyl, 2-methylpropyl, butyl, 2,2-dimethylpropyl, cyclopropyl, cyclopropylmethyl, cyclobutyl, cyclobutylmethyl, cyclopentyl, cyclopentylmethyl, 3,3,3-trifluoropropyl or 2-methoxyethyl.

In one aspect of the invention $R^1$ and $R^2$ together with the nitrogen to which they are attached form a saturated 5- to 6-membered ring optionally containing a further nitrogen atom wherein the ring is substituted on carbon or nitrogen by a group selected from phosphonooxy and $C_{1-4}$alkyl which $C_{1-4}$alkyl is substituted by phosphonooxy or —$NR^8R^9$, and where the ring is optionally further substituted on carbon or nitrogen by 1 or 2 $C_{1-4}$alkyl groups. In another aspect of the invention $R^1$ and $R^2$ together with the nitrogen to which they are attached form a piperidine, pyrrolidine or piperazine ring which is substituted by a group selected from phosphonooxy, phosphonooxymethyl, 2-phosphonooxyethyl, N-ethyl-N-(2-phosphonooxyethyl)aminomethyl and N-(2-phosphonooxyethyl)aminomethyl and where the ring is optionally further substituted by 1 or 2 methyl. In a further aspect of the invention $R^1$ and $R^2$ together with the nitrogen to which they are attached form 4-(phosphonooxymethyl)piperidinyl, 2-(phosphonooxymethyl)pyrrolidinyl, 4-(2-phosphonooxyethyl)piperazinyl, 3-(phosphonooxy)pyrrolidinyl, 3-(phosphonooxy)piperidinyl, 2-[N-ethyl-N-(2-phosphonooxyethyl)aminomethyl]pyrrolidinyl, 4-(phosphonooxy)piperidinyl, 2-[N-(2-phosphonooxyethyl)aminomethyl]pyrrolidinyl, 4-(2-phosphonooxyethyl)piperidinyl, 2-(2-phosphonooxyethyl)pyrrolidinyl and 2-(2-phosphonooxyethyl)piperidinyl. In yet another aspect $R^1$ and $R^2$ together with the nitrogen to which they are attached form 4-(phosphonooxymethyl)piperidinyl, 2-(phosphonooxymethyl)pyrrolidinyl, 2-(2-phosphonooxyethyl)pyrrolidinyl and 3-(phosphonooxy)piperidinyl. In a further aspect $R^1$ and $R^2$ together with the nitrogen to which they are attached form 2-(phosphonooxymethyl)pyrrolidinyl.

In one aspect of the invention $R^3$ is $C_{1-4}$alkoxy, halo or hydrogen. In a further aspect $R^3$ is $C_{1-4}$alkoxy or hydrogen. In another aspect $R^3$ is methoxy. In another aspect $R^3$ is hydrogen. In yet a further aspect $R^3$ is fluoro.

In one aspect $R^4$ is phenyl optionally substituted by 1 or 2 of fluoro or chloro. In another aspect $R^4$ is 3-fluorophenyl, 3-chlorophenyl, 3,5-difluorophenyl, 3,4-difluorophenyl, 2-fluorophenyl, 2,3-difluorophenyl, 2,4-difluorophenyl and 2,5-difluorophenyl. In a further aspect $R^4$ is 3-fluorophenyl, 3,5-difluorophenyl and 2,3-difluorophenyl. In one aspect $R^4$ is 3-fluorophenyl. In a further aspect $R^4$ is 3,5-difluorophenyl. In yet another aspect $R^4$ is 2,3-difluorophenyl.

In one aspect of the invention $R^5$ is hydrogen or methyl. In another aspect $R^5$ is hydrogen.

In one aspect of the invention $R^6$ is hydrogen, fluoro, chloro or methyl. In another aspect $R^6$ is hydrogen.

In one aspect of the invention $R^7$ is hydrogen, fluoro, chloro or methyl. In another aspect $R^7$ is hydrogen.

In one aspect $R^8$ is 2-phosphonooxyethyl.

In one aspect of the invention $R^9$ is hydrogen, methyl or ethyl.

In one aspect of the invention $R^{10}$ is hydrogen, methyl or ethyl.

In one aspect of the invention $R^{11}$ is hydrogen, methyl or ethyl.

In one aspect of the invention $R^{12}$ is hydrogen or methyl.

In one aspect of the invention $R^{13}$ is hydrogen or methyl.

In one aspect of the invention $R^{14}$ is hydrogen or methyl.

A preferred class of compounds is of formula (I) wherein:
A is a group of formula (a), (b), (c), (d) or (e) as defined above;
X is NH;
m is 0, 1, 2 or 3;

Z is —NR$^1$R$^2$ or a 5- to 6-membered saturated ring linked via a carbon atom containing a nitrogen atom and optionally containing a further nitrogen atom, which ring is substituted on carbon or nitrogen by phosphonooxy or C$_{1-4}$alkyl substituted by phosphonooxy;

R$^1$ is C$_{1-5}$alkyl substituted by phosphonooxy;

R$^2$ is selected from hydrogen and C$_{1-6}$alkyl which C$_{1-6}$alkyl is optionally substituted by 1, 2 or 3 halo or C$_{1-4}$alkoxy groups or R$^2$ is selected from C$_{2-6}$alkenyl, C$_{2-6}$alkynyl, C$_{3-6}$cycloalkyl and C$_{3-6}$cycloalkylC$_{1-4}$alkyl;

or R$^1$ and R$^2$ together with the nitrogen to which they are attached form a saturated 5- to 6-membered ring optionally containing a further nitrogen atom wherein the ring is substituted on carbon or nitrogen by a group selected from phosphonooxy and C$_{1-4}$alkyl which C$_{1-4}$alkyl is substituted by phosphonooxy or —NR$^8$R$^9$, and where the ring is optionally further substituted on carbon or nitrogen by 1 or 2 C$_{1-4}$alkyl groups;

R$^3$ is C$_{1-4}$alkoxy, halo or hydrogen;

R$^4$ is phenyl optionally substituted by 1 or 2 of fluoro or chloro;

R$^5$ is hydrogen or methyl; and

R$^6$ and R$^7$ are independently hydrogen, fluoro, chloro or methyl;

or a pharmaceutically acceptable salt thereof.

A preferred class of compounds is of formula (I) wherein:

A is a group of formula (a), (b), (c), (d) or (e) as defined above;

X is NH;

m is 1, 2 or 3;

Z is —NR$^1$R$^2$;

R$^1$ is C$_{1-5}$alkyl substituted by phosphonooxy;

R$^2$ is selected from hydrogen and C$_{1-6}$alkyl which C$_{1-6}$alkyl is optionally substituted by 1, 2 or 3 halo or C$_{1-4}$alkoxy groups, or R$^2$ is selected from C$_{2-6}$alkenyl, C$_{2-6}$alkynyl, C$_{3-6}$cycloalkyl and C$_{3-6}$cycloalkylC$_{1-4}$alkyl;

R$^3$ is C$_{1-4}$alkoxy, halo or hydrogen;

R$^4$ is phenyl optionally substituted by 1 or 2 of fluoro or chloro;

R$^5$ is hydrogen or methyl; and

R$^6$ and R$^7$ are independently hydrogen, fluoro, chloro or methyl;

or a pharmaceutically acceptable salt thereof.

Another preferred class of compounds is of formula (I) wherein:

A is a group of formula (a) as defined above;

X is NH;

m is 1, 2 or 3;

Z is —NR$^1$R$^2$;

R$^1$ is C$_{1-5}$alkyl substituted by phosphonooxy;

R$^2$ is selected from hydrogen and C$_{1-6}$alkyl which C$_{1-6}$alkyl is optionally substituted by 1, 2 or 3 halo or C$_{1-4}$alkoxy groups, or R$^2$ is selected from C$_{2-6}$alkenyl, C$_{2-6}$alkynyl, C$_{3-6}$cycloalkyl and C$_{3-6}$cycloalkylC$_{1-4}$alkyl;

R$^3$ is C$_{1-4}$alkoxy, halo or hydrogen;

R$^4$ is phenyl optionally substituted by 1 or 2 of fluoro or chloro;

R$^5$ is hydrogen; and

R$^6$ and R$^7$ are each hydrogen;

or a pharmaceutically acceptable salt thereof.

Yet another preferred class of compounds is of formula (I) wherein:

A is a group of formula (a) as defined above;

X is NH;

m is 1 or 2;

Z is —NR$^1$R$^2$;

R$^1$ is C$_{1-5}$alkyl substituted by phosphonooxy;

R$^2$ is selected from hydrogen and C$_{1-6}$alkyl which C$_{1-6}$alkyl is optionally substituted by 1, 2 or 3 halo or C$_{1-4}$alkoxy groups, or R$^2$ is selected from C$_{2-6}$alkenyl, C$_{2-6}$alkynyl, C$_{3-6}$cycloalkyl and C$_{3-6}$cycloalkylC$_{1-4}$alkyl;

R$^3$ is C$_{1-4}$alkoxy;

R$^4$ is phenyl optionally substituted by 1 or 2 of fluoro or chloro;

R$^5$ is hydrogen; and

R$^6$ and R$^7$ are each hydrogen;

or a pharmaceutically acceptable salt thereof.

A further preferred class of compounds is of formula (I) wherein:

A is a group of formula (a) as defined above;

X is NH;

m is 1, 2 or 3;

Z is —NR$^1$R$^2$;

R$^1$ is C$_{1-5}$alkyl substituted by phosphonooxy;

R$^2$ is selected from hydrogen and C$_{1-6}$alkyl which C$_{1-6}$alkyl is optionally substituted by 1, 2 or 3 halo or C$_{1-4}$alkoxy groups, or R$^2$ is selected from C$_{2-6}$alkenyl, C$_{2-6}$alkynyl, C$_{3-6}$cycloalkyl and C$_{3-6}$cycloalkylC$_{1-4}$alkyl;

R$^3$ is hydrogen;

R$^4$ is phenyl optionally substituted by 1 or 2 of fluoro or chloro;

R$^5$ is hydrogen; and

R$^6$ and R$^7$ are each hydrogen;

or a pharmaceutically acceptable salt thereof.

A further preferred class of compounds is of formula (I) wherein:

A is a group of formula (a) as defined above;

X is NH;

m is 1 or 2;

Z is —NR$^1$R$^2$;

R$^1$ is C$_{1-5}$alkyl substituted by phosphonooxy;

R$^2$ is selected from hydrogen and C$_{1-6}$alkyl which C$_{1-6}$alkyl is optionally substituted by 1, 2 or 3 halo or C$_{1-4}$alkoxy groups, or R$^2$ is selected from C$_{2-6}$alkenyl, C$_{2-6}$alkynyl, C$_{3-6}$cycloalkyl and C$_{3-6}$cycloalkylC$_{1-4}$alkyl;

R$^3$ is fluoro;

R$^4$ is phenyl optionally substituted by 1 or 2 of fluoro or chloro;

R$^5$ is hydrogen; and

R$^6$ and R$^7$ are each hydrogen;

or a pharmaceutically acceptable salt thereof.

Another preferred class of compounds is of formula (I) wherein:

A is a group of formula (a), (b), (c), (d) or (e) as defined above;

X is NH;

m is 0, 1 or 2;

Z is —NR$^1$R$^2$

R$^1$ and R$^2$ together with the nitrogen to which they are attached form a saturated 5- to 6-membered ring optionally containing a further nitrogen atom which ring is substituted by a group selected from phosphonooxy and C$_{1-4}$alkyl which C$_{1-4}$alkyl is substituted by phosphonooxy or —NR$^8$R$^9$, and where the ring is optionally further substituted by 1 or 2 C$_{1-4}$alkyl groups;

R$^3$ is C$_{1-4}$alkoxy, halo or hydrogen;

R$^4$ is phenyl optionally substituted by 1 or 2 of fluoro or chloro;

R$^5$ is hydrogen or methyl; and

R$^6$ and R$^7$ are independently hydrogen, fluoro, chloro or methyl;

R$^8$ is 2-phosphonooxyethyl; and

R$^9$ is hydrogen, methyl or ethyl;

or a pharmaceutically acceptable salt thereof.

A further preferred class of compounds is of formula (I) wherein:
A is a group of formula (a) as defined above;
X is NH;
m is 0, 1 or 2;
Z is —NR$^1$R$^2$
R$^1$ and R$^2$ together with the nitrogen to which they are attached form a saturated 5- to 6-membered ring optionally containing a further nitrogen atom wherein the ring is substituted on carbon or nitrogen by a group selected from phosphonooxy and C$_{1-4}$alkyl which C$_{1-4}$alkyl is substituted by phosphonooxy or —NR$^8$R$^9$, and where the ring is optionally further substituted on carbon or nitrogen by 1 or 2 C$_{1-4}$alkyl groups;
R$^3$ is C, alkoxy, halo or hydrogen;
R$^4$ is phenyl optionally substituted by 1 or 2 of fluoro or chloro;
R$^5$ is hydrogen or methyl; and
R$^6$ and R$^7$ are independently hydrogen, fluoro, chloro or methyl;
R$^8$ is 2-phosphonooxyethyl; and
R$^9$ is hydrogen, methyl or ethyl;

or a pharmaceutically acceptable salt thereof.

A further preferred class of compounds is of formula (I) wherein:
A is a group of formula (a) as defined above;
X is NH;
m is 0, 1 or 2;
Z is —NR$^1$R$^2$
R$^1$ and R$^2$ together with the nitrogen to which they are attached form a saturated 5- to 6-membered ring optionally containing a further nitrogen atom wherein the ring is substituted on carbon or nitrogen by a group selected from phosphonooxy and C$_{1-4}$alkyl which C$_{1-4}$alkyl is substituted by phosphonooxy or —NR$^8$R$^9$, and where the ring is optionally further substituted on carbon or nitrogen by 1 or 2 C$_{1-4}$alkyl groups;
R$^3$ is C$_{1-4}$alkoxy;
R$^4$ is phenyl optionally substituted by 1 or 2 of fluoro or chloro;
R$^5$ is hydrogen; and
R$^6$ and R$^7$ are each hydrogen;
R$^8$ is 2-phosphonooxyethyl; and
R$^9$ is hydrogen, methyl or ethyl;

or a pharmaceutically acceptable salt thereof.

A further preferred class of compounds is of formula (I) wherein:
A is a group of formula (a) as defined above;
X is NH;
m is 0, 1 or 2;
Z is —NR$^1$R$^2$
R$^1$ and R$^2$ together with the nitrogen to which they are attached form a saturated 5- to 6-membered ring optionally containing a further nitrogen atom wherein the ring is substituted on carbon or nitrogen by a group selected from phosphonooxy and C$_{1-4}$alkyl which C$_{1-4}$alkyl is substituted by phosphonooxy or —NR$^8$R$^9$, and where the ring is optionally further substituted on carbon or nitrogen by 1 or 2 C$_{1-4}$alkyl groups;
R$^3$ is hydrogen;
R$^4$ is phenyl optionally substituted by 1 or 2 of fluoro or chloro;
R$^5$ is hydrogen; and
R$^6$ and R$^7$ are each hydrogen;
R$^8$ is 2-phosphonooxyethyl; and
R$^9$ is hydrogen, methyl or ethyl;

or a pharmaceutically acceptable salt thereof.

In another aspect of the invention, a preferred compound of the invention is any compound selected from:
{1-[3-({4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl dihydrogen phosphate;
2-[[3-({4-[(5-{2-[(3,5-difluorophenyl)amino]-2-oxoethyl}-1H-pyrazol-3-yl)amino]-6-methoxyquinazolin-7-yl}oxy)propyl](ethyl)amino]ethyl dihydrogen phosphate;
{(2S)-1-[3-({4-[(5-{2-[(3,5-difluorophenyl)amino]-2-oxoethyl}-1H-pyrazol-3-yl)amino]-6-methoxyquinazolin-7-yl-}oxy)propyl]pyrrolidin-2-yl}methyl dihydrogen phosphate;
{(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;
{(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;
2-[[3-({4-[(5-{2-[(2,3-difluorophenyl)amino]-2-oxoethyl}-1H-pyrazol-3-yl)amino]-6 methoxyquinazolin-7-yl}oxy)propyl](propyl)amino]ethyl dihydrogen phosphate;
2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;
2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;
2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl dihydrogen phosphate;
2-[[3-({4-[(5-{2-[(3-fluorophenyl)amino]-1H-pyrazol-3-yl)amino]-6-methoxyquinazolin-7-yl}oxy)propyl](isobutyl)amino]ethyl dihydrogen phosphate;
2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;
1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl dihydrogen phosphate;
{(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;
2-[[3-({4-[(5-{2-[(3,5-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;
2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl dihydrogen phosphate;
2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;
2-[[3-({4-[(5-{2-[(2,3-difluorophenyl)amino]-2-oxoethyl}-1H-pyrazol-3-yl)amino]-6-methoxyquinazolin-7-yl}oxy)propyl) (2-methoxyethyl)amino]ethyl dihydrogen phosphate;
2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-{(cyclobutylmethyl)[3-({4-[(5-{2-[(2,3-difluorophenyl) amino]-2-oxoethyl}-1H-pyrazol-3-yl)amino]-6-methoxyquinazolin-7-yl}oxy)propyl]amino}ethyl dihydrogen phosphate;

2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl dihydrogen phosphate;

2-{allyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{(cyclopropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-{(cyclopropylmethyl)[3-({4-[(5-{2-[(2,3-difluorophenyl) amino]-2-oxoethyl}-1H-pyrazol-3-yl)amino]-6-methoxyquinazolin-7-yl}oxy)propyl]amino}ethyl dihydrogen phosphate and 2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

or a pharmaceutically acceptable salt thereof.

A more preferred compound of the invention is any compound selected from:

2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](isopropyl)amino]ethyl dihydrogen phosphate;

3-{[3-({4-[(5-{2-[(2,3-difluorophenyl)amino]-2-oxoethyl}-1H-pyrazol-3-yl)amino]quinazolin-7-yl}oxy)propyl] amino}-3-methylbutyl dihydrogen phosphate;

2-{(2S)-1-[3-({4-[(5-{2-[(2,3-difluorophenyl)amino]-2-oxoethyl}-1H-pyrazol-3-yl)amino]-quinazolin-7-yl}oxy) propyl]pyrrolidin-2-yl}ethyl dihydrogen phosphate;

{(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl dihydrogen phosphate;

2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl dihydrogen phosphate;

{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

{(2S)-1-[3-({4-[(5 {2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

2-{cyclopentyl[3-({4-[(5-{2-[(3-fluorophenyl)amino]-2-oxoethyl}-1H-pyrazol-3-yl)amino]-quinazolin-7-yl}oxy) propyl]amino}ethyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl dihydrogen phosphate;

2-{[3-({4-[(5-{2-[(3-fluorophenyl)amino]-2-oxoethyl}-1H-pyrazol-3-yl)amino]quinazolin-7-yl}oxy)propyl]amino}-2-methylpropyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl dihydrogen phosphate;

{(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl dihydrogen phosphate 2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl dihydrogen phosphate 2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl dihydrogen phosphate;

2-[[4-({4-[(5-{2-[(2,3-difluorophenyl)amino]-2-oxoethyl}-1H-pyrazol-3-yl)amino]-quinazolin-7-yl}oxy)butyl](ethyl)amino]ethyl dihydrogen phosphate;

{(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl dihydrogen phosphate; and {(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

or a pharmaceutically acceptable salt thereof

A further preferred compound is:

2-{ethyl[3-({6-fluoro-4-[(5-{2-[(3-fluorophenyl)amino]-2-oxoethyl}-1H-pyrazol-3-yl)amino]quinazolin-7-yl}oxy) propyl]amino}ethyl dihydrogen phosphate;

or a pharmaceutically acceptable salt thereof.

A more preferred compound is any compound selected from:

{1-[3-({4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl dihydrogen phosphate;

{(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

2-[[3-({4-[(5-{2-[(3-fluorophenyl)amino]-2-oxoethyl}-1H-pyrazol-3-yl)amino]-6-methoxyquinazolin-7-yl}oxy)propyl](isobutyl)amino]ethyl dihydrogen phosphate;

2-{(2,2-dimethylpropyl)[3-({4-[(5-{2-[(3-fluorophenyl) amino]-2-oxoethyl}-1H-pyrazol-3-yl)amino]-6-methoxyquinazolin-7-yl}oxy)propyl]amino}ethyl dihydrogen phosphate;

1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl dihydrogen phosphate;

2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl dihydrogen phosphate;

2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

{(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

2-{cyclopentyl[3-({4-[(5-{2-[(3-fluorophenyl)amino]-2-oxoethyl}-1H-pyrazol-3-yl)amino]-quinazolin-7-yl}oxy)propyl]amino}ethyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl dihydrogen phosphate;

2-{[3-({4-[(5-{2-[(3-fluorophenyl)amino]-2-oxoethyl}-1H-pyrazol-3-yl)amino]quinazolin-7-yl}oxy)propyl]amino}-2-methylpropyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl dihydrogen phosphate;

{(2R)-1 [3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl dihydrogen phosphate;

2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl dihydrogen phosphate; and 2-{ethyl[3-({6-fluoro-4-[(5-{2-[(3-fluorophenyl)amino]-2-oxoethyl}-1H-pyrazol-3-yl)amino]quinazolin-7-yl}oxy)propyl]amino}ethyl dihydrogen phosphate;

or a pharmaceutically acceptable salt thereof

A further preferred compound is any compound selected from:

{1-[3-({4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl dihydrogen phosphate;

{(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

2-[[3-({4-[(5-{2-[(3-fluorophenyl)amino]-2-oxoethyl}-1H-pyrazol-3-yl)amino]-6-methoxyquinazolin-7-yl}oxy)propyl](isobutyl)amino]ethyl dihydrogen phosphate;

2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl dihydrogen phosphate;

2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl dihydrogen phosphate;

2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate; and 2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

or a pharmaceutically acceptable salt thereof.

Another preferred compound is any compound selected from:

2-[[3-({4[(5-{2-[(3-fluorophenyl)amino]-2-oxoethyl}-1H-pyrazol-3-yl)amino]-6-methoxyquinazolin-7-yl}oxy)propyl](isobutyl)amino]ethyl dihydrogen phosphate;

2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl dihydrogen phosphate;

2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino) ethyl dihydrogen phosphate; and 2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate;

or a pharmaceutically acceptable salt thereof.

A particularly preferred compound is any compound selected from:

{(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

2-{cyclopentyl[3'-({4-[(5-{2-[(3-fluorophenyl)amino]-2-oxoethyl}-1H-pyrazol-3-yl)amino]-quinazolin-7-yl}oxy)propyl]amino}ethyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl dihydrogen phosphate;

2-{[3-({4-[(5-{2-[(3-fluorophenyl)amino]-2-oxoethyl}-1H-pyrazol-3-yl)amino]quinazolin-7-yl}oxy)propyl]amino}-2-methylpropyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl dihydrogen phosphate;

{(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl dihydrogen phosphate; and 2-[[3-({4-[(5-{2-[(3-fluorophenyl)amino]-2-oxoethyl)-1H-pyrazol-3-yl)amino]quinazolin-7-yl}oxy)propyl](2-methoxyethyl)amino]ethyl dihydrogen phosphate;

or a pharmaceutically acceptable salt thereof.

An especially preferred compound of the invention is any compound selected from:

2-{cyclopentyl[3-({4-[(5-{2-[(3-fluorophenyl)amino]-2-oxoethyl}-1H-pyrazol-3-yl)amino]-quinazolin-7-yl}oxy)propyl]amino}ethyl dihydrogen phosphate;

2-[[3-({4[(5-{2-[(3-fluorophenyl)amino]-2-oxoethyl}-1H-pyrazol-3-yl)amino]-quinazolin-7-yl}oxy)propyl](ethyl)amino]ethyl dihydrogen phosphate;

2-{[3-({4-[(5-{2-[(3-fluorophenyl)amino]-2-oxoethyl}-1H-pyrazol-3-yl)amino]quinazolin-7-yl}oxy)propyl]amino}-2-methylpropyl dihydrogen phosphate;

2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl dihydrogen phosphate;

3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl dihydrogen phosphate; and 2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl dihydrogen phosphate;

or a pharmaceutically acceptable salt thereof.

A further preferred compound is any compound selected from:

2-[[3-({4-[(5-{2-[(3,5-difluorophenyl)amino]-2-oxoethyl}-1H-pyrazol-3-yl)amino]-6-methoxyquinazolin-7-yl}oxy)propyl](ethyl)amino]ethyl dihydrogen phosphate;

{(2S)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

{(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;

2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl dihydrogen phosphate; and 2-[[3-({4-[(5-{2-[(3,5-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;

or a pharmaceutically acceptable salt thereof.

A further preferred compound is any compound selected from:

2-[[3-({4-[(5-{2-[(3,5-difluorophenyl)amino]-2-oxoethyl}-1H-pyrazol-3-yl)amino]-6-methoxyquinazolin-7-yl}oxy)propyl](ethyl)amino]ethyl dihydrogen phosphate;

2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;

2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl dihydrogen phosphate; and 2-[[3-({4-[(5-{2-[(3,5-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;

or a pharmaceutically acceptable salt thereof.

Another more preferred compound is any compound selected from:

2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;

{(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](2-methoxyethyl)amino]ethyl dihydrogen phosphate;

2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{allyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{(cyclopropylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl dihydrogen phosphate;

2-[[3-(f{4-[(5-{2-[(2,3-difluorophenyl)amino]-2-oxoethyl}-1H-pyrazol-3-yl)amino]-quinazolin-7-yl}oxy)propyl](ethyl)amino]ethyl dihydrogen phosphate;

2-[[3-({4-[(5-{2-[(2,3-difluorophenyl)amino]-2-oxoethyl}-1H-pyrazol-3-yl)amino]quinazolin-7-yl}oxy)propyl](isopropyl)amino]ethyl dihydrogen phosphate;

3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl dihydrogenphosphate;

2-{(2S)-1-[3-({4[(5-{2-[(2,3-difluorophenyl)amino]-2-oxoethyl}-1H-pyrazol-3-yl)amino]-quinazolin-7-yl}oxy)propyl]pyrrolidin-2-yl}ethyl dihydrogen phosphate;

{(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl dihydrogen phosphate;

2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl dihydrogen phosphate;

{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl dihydrogen phosphate;

2-[[4-({4-[(5-{2-[(2,3-difluorophenyl)amino]-2-oxoethyl}-1H-pyrazol-3-yl)amino]-quinazolin-7-yl}oxy)butyl](ethyl)amino]ethyl dihydrogen phosphate;

{(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl dihydrogen phosphate; and {(2S)1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

or a pharmaceutically acceptable salt thereof.

A particularly preferred compound is any compound selected from:

2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;

{(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](2-methoxyethyl)amino]ethyl dihydrogen phosphate;

2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{allyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate; and 2-{(cyclopropylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

or a pharmaceutically acceptable salt thereof.

Yet another preferred compound is any compound selected from:

2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl dihydrogen phosphate;

2-[[3-({4-[(5-{2-[(2,3-difluorophenyl)amino]-2-oxoethyl}-1H-pyrazol-3-yl)amino]-6-methoxyquinazolin-7-yl}oxy)propyl](2-methoxyethyl)amino]ethyl dihydrogen phosphate;

2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{allyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

2-{cyclopentyl[3-({-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate; and 2-{(cyclopropylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate;

or a pharmaceutically acceptable salt thereof.

Another preferred compound is any compound selected from:

2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](isopropyl)amino]ethyl dihydrogen phosphate;

3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl dihydrogen phosphate;

2-f{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}ethyl dihydrogen phosphate;

{(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl dihydrogen phosphate;

2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl dihydrogen phosphate;

{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl dihydrogen phosphate;

2-[[4-({4-[(5-{2-[(2,3-difluorophenyl)amino]-2-oxoethyl}-1H-pyrazol-3-yl)amino]-quinazolin-7-yl}oxy)butyl](ethyl)amino]ethyl dihydrogen phosphate;

{(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl dihydrogen phosphate; and {(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

or a pharmaceutically acceptable salt thereof.

Yet another preferred compound is any compound selected from:

2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](isopropyl)amino]ethyl dihydrogen phosphate;

3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl dihydrogen phosphate;

2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl dihydrogen phosphate;

2-[[3-({-[(5-{2-[(2,3-difluorophenyl)amino]-2-oxoethyl}-1H-pyrazol-3-yl)amino]-quinazolin-7-yl}oxy)propyl](butyl)amino]ethyl dihydrogen phosphate;

2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl dihydrogen phosphate;

2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl dihydrogen phosphate;

2-[[4-({4-[(5-{2-[(2,3-difluorophenyl)amino]-2-oxoethyl}-1H-pyrazol-3-yl)amino]-20 quinazolin-7-yl}oxy)butyl](ethyl)amino]ethyl dihydrogen phosphate; and 2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl dihydrogen phosphate;

or a pharmaceutically acceptable salt thereof.

A further particularly preferred compound is any compound selected from:

{1-[3-(f{4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl dihydrogen phosphate;

{(2S)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

{(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogenphosphate;

{(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl dihydrogen phosphate;

{(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate;

2-{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}ethyl dihydrogen phosphate;

{(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate;

{(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

{(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate;

{(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate; and {(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate;

or a pharmaceutically acceptable salt thereof.

A further embodiment of the invention comprises any one of:

N-(2,3-difluorophenyl)-2-{3-[(7-{[1-(2-hydroxyethyl)piperidin-4-yl]methoxy}quinazolin-4-yl)amino]-1H-pyrazol-5-yl}acetamide;

N-(2,3-difluorophenyl)-2-{3-[(7-{3-[(3-hydroxy-1,1-dimethylpropyl)amino]propoxy}quinazolin-4-yl)amino]-1H-pyrazol-5-yl}acetamide;

N-(2,3-difluorophenyl)-2-{3-[(7-{3-[(2S)-2-(2-hydroxyethyl)pyrrolidin-1-yl]propoxy}-quinazolin-4-yl)amino]-1H-pyrazol-5-yl}acetamide;

N-(2,3-difluorophenyl)-2-{3-[(7-{3-[(2-hydroxyethyl)(butyl)amino]propoxy}-quinazolin-4-yl)amino]-1H-pyrazol-5-yl}acetamide;

2-{3-[(7-{3-[cyclopentyl(2-hydroxyethyl)amino]propoxy}-quinazolin-4-yl)amino]-1H-pyrazol-5-yl}-N-(2,3-difluorophenyl)acetamide;

N-(2,3-difluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide;

N-(3-fluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide;

2-{3-[(7-{3-[cyclopentyl(2-hydroxyethyl)amino]propoxy}-quinazolin-4-yl)amino]-1H-pyrazol-5-yl}-N-(3-fluorophenyl)acetamide;

N-(3-fluorophenyl)-2-{3-[(7-{3-[(3-ethyl(2-hydroxyethyl)amino]propoxy}-quinazolin-4-yl)amino]-1H-pyrazol-5-yl}acetamide;

N-(3-fluorophenyl)-2-{3-[(7-{3-[(2-hydroxy-1,1-dimethylethyl)amino]propoxy}quinazolin-4-yl)amino]-1H-pyrazol-5-yl}acetamide;

N-(3-fluorophenyl)-2-{3-[(7-{3-[(2-hydroxyethyl)(propyl)amino]propoxy}-quinazolin-4-yl)amino]-1H-pyrazol-5-yl}acetamide;

N-(3-fluorophenyl)-2-{3-[(7-{3-[(2R)-2-(hydroxymethyl)pyrrolidin-1-yl]propoxy}-quinazolin-4-yl)amino]-1H-pyrazol-5-yl}acetamide;

N-(2,3-difluorophenyl)-2-{3-[(7-{4-[(2-hydroxyethyl)(propyl)amino]butoxy}-quinazolin-4-yl)amino]-1H-pyrazol-5-yl}acetamide;

N-(3-fluorophenyl)-2-{3-[(7-{4-[ethyl(2-hydroxyethyl)amino]butoxy}-quinazolin-4-yl)amino]-1H-pyrazol-5-yl}acetamide;

N-(2,3-difluorophenyl)-2-{3-[(7-{4-[(2R)-2-(hydroxymethyl)pyrrolidin-1-yl]butoxy}-quinazolin-4-yl)amino]-1H-pyrazol-5-yl}acetamide;

N-(2,3-difluorophenyl)-2-{3-[(7-{4-[(2-hydroxyethyl)(methyl)amino]butoxy}quinazolin-4-yl)amino]-1H-pyrazol-5-yl}acetamide;

N-(2,3-difluorophenyl)-2-{3-[(7-{4-[(2S)-2-(hydroxymethyl)pyrrolidin-1-yl]butoxy}-quinazolin-4-yl)amino]-1H-pyrazol-5-yl}acetamide;

2-{3-[(7-{3-[ethyl(3-hydroxypropyl)amino]propoxy}-quinazolin-4-yl)amino]-1H-pyrazol-5-yl}-N-(3-fluorophenyl)acetamide;

N-(3-fluorophenyl)-2-{3-[(7-{3-[(2-hydroxyethyl)(2-methoxyethyl)amino]propoxy}quinazolin-4-yl)amino]-1H-pyrazol-5-yl}acetamide; and 2-{3-[(7-{3-[ethyl(2-hydroxyethyl)amino]propoxy}-6-fluoroquinazolin-4-yl)amino]-1H-pyrazol-5-yl}-N-(3-fluorophenyl)acetamide;

or a pharmaceutically acceptable salt thereof.

Synthetic routes to any of compounds can be found in the examples.

A preferred compound of this embodiment is any compound selected from:

N-(3-fluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide;

2-{3-[(7-{3-[cyclopentyl(2-hydroxyethyl)amino]propoxy}-quinazolin-4-yl)amino]-1H-pyrazol-5-yl}-N-(3-fluorophenyl)acetamide;

N-(3-fluorophenyl)-2-{3-[(7-{3-[ethyl(2-hydroxyethyl)amino]propoxy}-quinazolin-4-yl)amino]-1H-pyrazol-5-yl}acetamide;

N-(3-fluorophenyl)-2-{3-[(7-{3-[(2-hydroxy-1,1-dimethylethyl)amino]propoxy}quinazolin-4-yl)amino]-1H-pyrazol-5-yl}acetamide;

N-(3-fluorophenyl)-2-{3-[(7-{3-[(2-hydroxyethyl)(propyl)amino]propoxy}-quinazolin-4-yl)amino]-1H-pyrazol-5-yl}acetamide;

N-(3-fluorophenyl)-2-{3-[(7-{3-[(2R)-2-(hydroxymethyl)pyrrolidin-1-yl]propoxy}-quinazolin-4-yl)amino]-1H-pyrazol-5-yl}acetamide;

N-(3-fluorophenyl)-2-{3-[(7-{4-[ethyl(2-hydroxyethyl)amino]butoxy}-quinazolin-4-yl)amino]-1H-pyrazol-5-yl}acetamide;

2-{3-[(7-{3-[ethyl(3-hydroxypropyl)amino]propoxy}-quinazolin-4-yl)amino]-1H-pyrazol-5-yl}-N-(3-fluorophenyl)acetamide;

N-(3-fluorophenyl)-2-{3-[(7-{3-[(2-hydroxyethyl)(2-methoxyethyl)amino]propoxy}quinazolin-4-yl)amino]-1H-pyrazol-5-yl}acetamide; and 2-{3-[(7-{3-[ethyl(2-hydroxyethyl)amino]propoxy}-6-fluoroquinazolin-4-yl)amino]-1H-pyrazol-5-yl}-N-(3-fluorophenyl)acetamide;

or a pharmaceutically acceptable salt thereof.

Another preferred compound is any compound selected from:

N-(2,3-difluorophenyl)-2-{3-[(7-{[1-(2-hydroxyethyl)piperidin-4-yl]methoxy}quinazolin-4-yl)amino]-1H-pyrazol-5-yl}acetamide;

N-(2,3-difluorophenyl)-2-{3-[(7-{3-[(3-hydroxy-1,1-dimethylpropyl)amino]propoxy}quinazolin-4-yl)amino]-1H-pyrazol-5-yl}acetamide;

N-(2,3-difluorophenyl)-2-{3-[(7-{3-[(2S)-2-(2-hydroxyethyl)pyrrolidin-1-yl]propoxy}-quinazolin-4-yl)amino]-1H-pyrazol-5-yl}acetamide;

N-(2,3-difluorophenyl)-2-{3-[(7-{3-[(2-hydroxyethyl)(butyl)amino]propoxy}-quinazolin-4-yl)amino]-1H-pyrazol-5-yl}acetamide;

2-{3-[(7-{3-[cyclopentyl(2-hydroxyethyl)amino]propoxy}-quinazolin-4-yl)amino]-1H-pyrazol-5-yl}-N-(2,3-difluorophenyl)acetamide;

N-(2,3-difluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide;

N-(2,3-difluorophenyl)-2-{3-[(7-{4-[(2-hydroxyethyl)(propyl)amino]butoxy}-quinazolin-4-yl)amino]-1H-pyrazol-5-yl}acetamide;

N-(2,3-difluorophenyl)-2-{3-[(7-{4-[(2R)-2-(hydroxymethyl)pyrrolidin-1-yl]butoxy}-quinazolin-4-yl)amino]-1H-pyrazol-5-yl}acetamide;

N-(2,3-difluorophenyl)-2-{3-[(7-{4-[(2-hydroxyethyl)(methyl)amino]butoxy}quinazolin-4-yl)amino]-1H-pyrazol-5-yl}acetamide; and N-(2,3-difluorophenyl)-2-{3-[(7-{4-[(2S)-2-(hydroxymethyl)pyrrolidin-1-yl]butoxy}-quinazolin-4-yl)amino]-1H-pyrazol-5-yl}acetamide;

or a pharmaceutically acceptable salt thereof.

In another aspect the present invention provides a process for the preparation of a compound of formula (I) or a pharmaceutically acceptable salt thereof, which process comprises converting a compound of formula (II) into a compound of formula (I by phosphorylation of an appropriate hydroxy group:

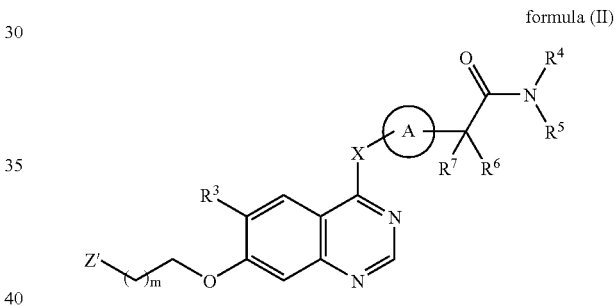

formula (II)

where A, X, m, $R^3$, $R^4$, $R^5$, $R^6$, $R^7$ and $R^9$ are as defined for formula (I); and Z' is a group selected from —$NR^{1'}R^{2'}$, hydroxy, $C_{3-6}$cycloalkyl which $C_{3-6}$cycloalkyl is substituted by hydroxy or $C_{1-4}$alkyl substituted by hydroxy, and a 4- to 7-membered ring linked via a carbon atom containing a nitrogen atom and optionally containing a further nitrogen atom, which ring may be saturated, unsaturated or partially saturated wherein the ring is substituted on carbon or nitrogen by hydroxy or $C_{1-4}$alkyl substituted by hydroxy and wherein the ring is optionally further substituted on carbon or nitrogen by 1, 2 or 3 halo or $C_{1-4}$alkyl groups; $R^{1'}$ is a group selected from —$COR^{8'}$, —$CONR^{8'}R^9$ and $C_{1-6}$alkyl which $C_{1-6}$alkyl is substituted by hydroxy and optionally further substituted by 1 or 2 halo or methoxy groups; $R^{2'}$ is a group selected from hydrogen, —COR $^{10'}$, —$CONR^{10}R^{11}$ and $C_{1-6}$alkyl which $C_{1-6}$alkyl is optionally substituted by 1, 2 or 3 halo or $C_{1-4}$alkoxy groups or —$S(O)_pR^{11}$ (where p is 0, 1 or 2) or hydroxy, or $R^2$ is selected from $C_{2-6}$alkenyl, $C_{2-6}$alkynyl, $C_{3-6}$cycloalkyl and $C_{3-6}$cycloalkyl$C_{1-4}$alkyl;

or $R^{1'}$ and $R^{2'}$ together with the nitrogen to which they are attached form a 4- to 7-membered ring optionally containing a further nitrogen atom which may be saturated, unsaturated or partially saturated wherein the ring is substituted on carbon or nitrogen by a group selected from hydroxy and $C_{1-4}$alkyl substituted by hydroxy or —$NR^8R^9$ and where the ring is optionally further substituted on carbon or nitrogen by 1, 2 or 3 halo or $C_{1-4}$alkyl groups; and where $R^{8'}$ is $C_{1-4}$alkyl substituted by hydroxy and optionally further substituted by 1 or 2 halo or methoxy groups:

and thereafter if necessary:
i) converting a compound of the formula (I) into another compound of the formula (I); and/or
ii) removing any protecting groups; and/or
iii) forming a pharmaceutically acceptable salt thereof.

Phosphorylation may be suitably performed by treatment with 1-H tetrazole (or a suitable replacement such as S-ethyl tetrazole or pyridinium hydrochloride) and di-tert-butyldiethylphosphoramidite or dibenzyldiethylphosphoramidite at 5 to 35° C. under an inert atmosphere for 30 minutes to 4 hours followed by treatment with an oxidizing agent such as meta-chloroperbenzoic acid (mCPBA) or 30% aqueous hydrogen peroxide at −10 to 25° C. for 2 to 18 hours. Deprotection of the tert-butyl groups to yield the phosphate group is required as a final step with these reagents and may be readily achieved by treatment with 4.0 N hydrochloric acid in 1,4-dioxane at 10 to 35° C. for 12 to 18 hours.

This process may further comprise a method for the preparation of a compound of formula (II) where Z' is —$NR^{1'}R^{2'}$ which method comprises the reaction of a compound of formula (III) where L is a leaving group such as halo (e.g. chloro):

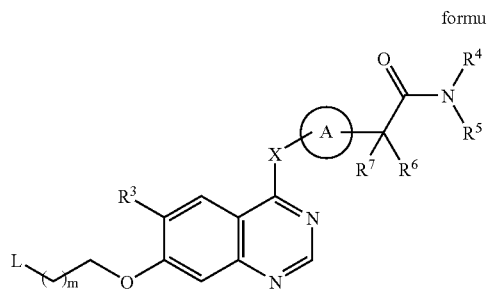

formula (III)

with an amine of formula (IV):

formula (IV)

Suitable reaction conditions for this method include heating a compound of formula (III) with an excess of amine of formula (IV) in an inert solvent such as dimethylacetamide, with or without the addition of a suitable catalyst (such as tetra-n-butylammoniuim iodide or potassium iodide) at a temperature of 50 to 100° C. for 12 to 72 hours. In an alternative procedure, the leaving group L in formula (III) may be a carboxaldehyde and the reaction with amine (IV) may be carried out under reductive conditions using a reducing agent such as sodium cyanoborohydride.

The amines of formula (IV) are known in the art or may be prepared by the skilled person using methods known in the art.

The process may further comprise a method for the preparation of a compound of formula (III) where X is $NR^{14}$ which method comprises the reaction of a compound of formula (V)

where R' and R" are alkyl groups such as methyl and ethyl and L is as defined in relation to formula (III):

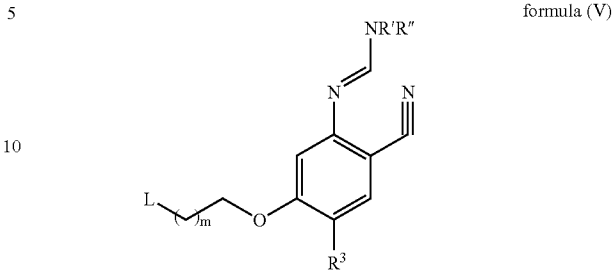

formula (V)

with a compound of formula (VI) where R may be either hydrogen or a group such as tert-butoxycarbonyl (Boc) or trityl:

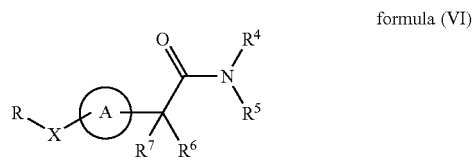

formula (VI)

Such a reaction can be achieved under a range of conditions described in the literature, such as heating a compound of formula (V) with a compound of formula (VI) in a solvent such as acetic acid at a temperature of 100 to 130° C. for 2 to 18 hours.

Alternatively, the process may further comprise a method for the preparation of a compound of formula (III) where X is $NR^{14}$, O or S which method comprises the reaction of a compound of formula (VII) where R* is a leaving group such as halo (e.g. chloro):

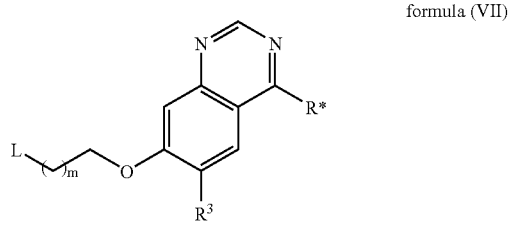

formula (VII)

with a compound of formula (VI) where R is either hydrogen or tert-butoxycarbonyl (Boc) or trityl. Such a reaction can be achieved under a range of conditions described in the literature, such as heating a compound of formula (VII) with a compound of formula (VI) in a solvent such as isopropanol or dimethylacetamide, in the presence of an acid catalyst such as hydrochloric acid, at a temperature of 80 to 100° C. for 2 to 6 hours. Alternatively the reaction may be effected using a base such as sodium hydride carrying out the reaction in an inert solvent such as dimethylformamide at a temperature of 50 to 80° C. for 2 to 6 hours.

Compounds of formula (V) can be prepared from a compound of formula (VIII) where P is a hydroxy protecting group such as benzyl:

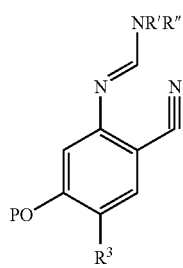

formula (VIII)

by reaction with a compound of formula (IX) where L' is a leaving group such as halo (e.g. bromo) and L is as defined in relation to formula (III):

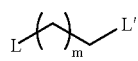

formula (IX)

Such a reaction can be achieved (after removal of the protecting group using a method selected from those already described in the literature) under a range of conditions described in the literature such as heating a compound of formula (VIII) with a compound of formula (IX) in the presence of a catalyst such as caesium carbonate in a solvent such as acetonitrile at a temperature of 80 to 100° C. for 1 to 4 hours.

A method for the preparation of a compound of formula (VIII) comprises the reaction of a compound of formula (X) where P is as defined in relation for formula (VIII):

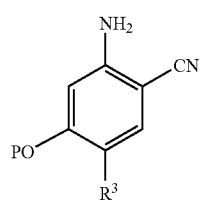

formula (X)

with an appropriate acetal such as N,N-dimethylformamide dimethyl acetal. The reaction is suitably effected in an organic solvent such as toluene or benzene, at elevated temperature, conveniently at the reflux temperature of the solvent.

Compounds of formula (X) are either known compounds or they can be prepared by the skilled person using conventional methods. In particular, compounds of formula (X) may be prepared by reduction of the corresponding nitro compound of formula (XI) where P is as described in relation to formula (VIII):

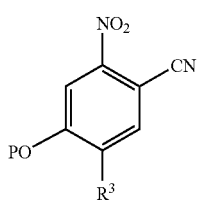

formula (XI)

Suitable reaction conditions are illustrated hereinafter.

Compounds of formula (XI) may be obtained by nitration of a compound of formula (XII) where P is as defined in relation to formula (VIII)

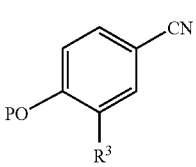

formula (XII)

for example, using nitric acid as the nitrating agent. Again, suitable reaction conditions are illustrated hereinafter.

The nitrile of formula (XII) may be derived by reaction of the corresponding aldehyde of formula (XIII) with hydroxylamine as illustrated hereinafter:

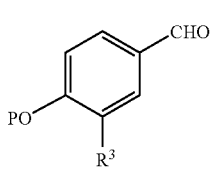

formula (XIII)

The process may further comprise a method for the preparation of a compound according to formula (VII) which method comprises the reaction of a compound of formula (XIV)

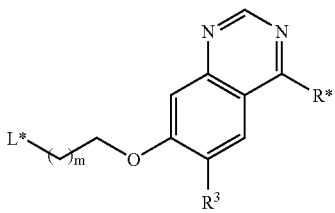

formula (XIV)

where L* is a hydroxy group, with a suitable chlorinating agent such as thionyl chloride, phoshoryl chloride or phoshorus pentachloride. Again, suitable reaction conditions are illustrated hereinafter.

Compounds of formula (XIV) are either known compounds or they can be prepared by the skilled person using conventional methods. In particular, compounds of formula (XIV) may be prepared by reaction of a compound of formula (XV) where L" is a leaving group such as halo (fluoro)

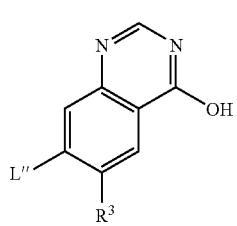

formula (XV)

with a compound of formula (XVI) where L* is a hydroxy group:

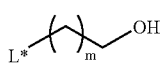

formula (XVI)

Suitable reaction conditions are illustrated hereinafter.

Compounds of formula (XV) are either known compounds or they can be prepared by the skilled person using conventional methods. In particular, compounds of formula (XV) may be prepared by reaction of a compound of formula (XVII) (where L" is a leaving group such as halo (fluoro) and L'" is an alkoxy or hydroxy group) by reaction with neat formamide at a temperature of 140 to 200° C. for 3 to 6 hours.

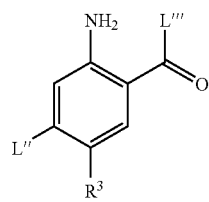

formula (XVII)

Suitable reaction conditions are illustrated hereinafter.

Compounds of formula (XVII) are either known compounds or they can be prepared by the skilled person using conventional methods. In particular, compounds of formula (XVII) may be prepared by reduction of a compound of formula (XVIII) (where L" is a leaving group such as halo (fluoro) and L'" is an alkoxy or hydroxy group) using a reducing agent such as sodium dithionite in a water: dichloromethane solvent system at ambient temperature for 1 to 3 hours.

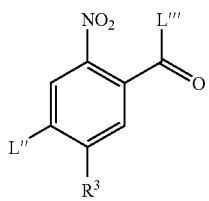

formula (XVIII)

Compounds of formula (XVIII) may be obtained by nitration of a compound of formula (XIX) where L" and L'" are as defined in relation to formula (XVIII)

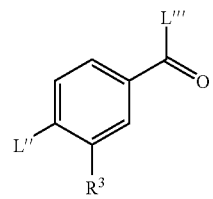

formula (XIX)

for example, using nitric acid as the nitrating agent. Again, suitable reaction conditions are illustrated hereinafter.

The process may further comprise a method for the preparation of a compound according to formula (VI) where X is $NR^{14}$, O or S which method comprises the reaction of a compound of formula (XX), where P is a suitable protecting group:

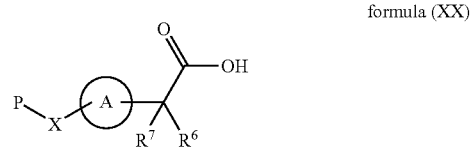

formula (XX)

with an amine of formula $HNR^4R^5$ in the presence of a coupling reagent (such as O-(7-azabenzotriazol-1-yl)-N,N,N', N'-tetramethyluronium hexafluorophosphate) and diisopropylethylamine in a solvent (such as dimethylacetamide) under inert and anhydrous conditions.

A compound of formula (XX) where X is $NR^{14}$ and P is COOR may be prepared from a compound of formula (XXI):

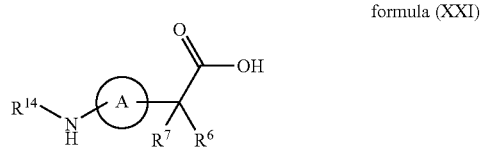

formula (XXI)

with a compound of formula (XXII) where L is an appropriate leaving group:

formula (XXII)

Suitable reagent and reaction conditions for this reaction include the use of di(tert-butyl)dicarbonate and triethylamine in tetrahydrofuran at 0° C. under a nitrogen atmosphere.

A compound of formula (III) may also be prepared (following deprotection) from a compound of formula (XX) by reacting it with a compound of formula (V) under a range of conditions described in the literature, such as heating the reaction mixture in a solvent such as acetic acid at a temperature of 100 to 130° C. for 2 to 18 hours. The product, a compound of formula (XXIII):

formula (XXIII)

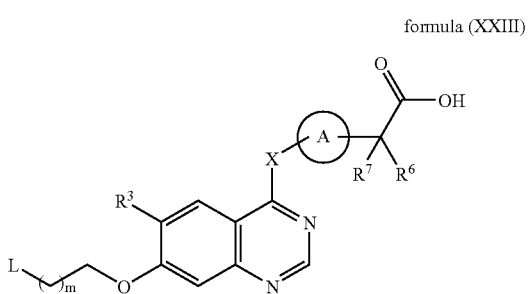

may then be reacted with an amine of formula $HNR^4R^5$ in the presence of a coupling agent (such as O-(7-azabenzotriazol-1-yl)-N,N,N',N'-tetramethyluronium hexafluorophosphate) and diisopropylethylamine in a solvent (such as dimethylacetamide) under inert and anhydrous conditions.

Further a compound of formula (XXIII) may also be prepared by reacting a deprotected compound of formula (XX) with a compound of formula (VII) under a range of conditions described in the literature, such as heating the reaction mixture in a solvent such as isopropanol or dimethylacetamide, in the presence of an acid catalyst such as hydrochloric acid, at a temperature of 80 to 100° C. for 2 to 6 hours. Alternatively the reaction may be effected using a base such as sodium hydride; carrying out the reaction in an inert solvent such as dimethylformamide at a temperature of 50 to 80° C. for 2 to 6 hours.

Compounds of formula (XXI) which comprise a heteroaromatic ring are made according to the literature. However for illustrative purpose, when A is a pyrazole ring, a compound of formula (XXI) may be prepared according to the following scheme:

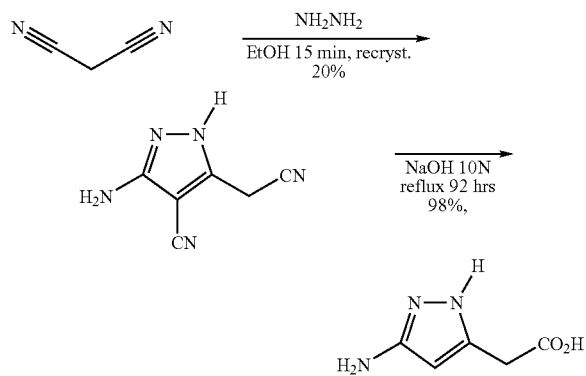

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

According to a further aspect of the invention there is provided a pharmaceutical composition which comprises a compound formula (I), or a pharmaceutically acceptable salt thereof, as defined herein in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, soya bean oil, coconut oil, or preferably olive oil, or any other acceptable vehicle.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible or lyophilised powders and granules suitable for preparation of an aqueous suspension or solution by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, solutions, emulsions or particular systems, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in polyethylene glycol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30 µm or much less preferably 5 µm or less and more preferably between 5 µm and 1 µm, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

Therefore in a further aspect of the invention there is provided a compound of formula (I), or a pharmaceutically acceptable salt thereof, for use in therapy. Further provided is a compound of formula (I), or a pharmaceutically acceptable salt thereof, for use as a medicament. A compound of formula (I), or a pharmaceutically acceptable salt thereof, is also provided for use in the treatment of a disease where the inhibition of one or more Aurora kinase is beneficial. In particular it is envisaged that inhibition of Aurora-A kinase and/or Aurora-B kinase may be beneficial. Preferably inhibition of Aurora-B kinase is beneficial. A compound of formula (I), or a pharmaceutically acceptable salt thereof, has further use in the treatment of hyperproliferative diseases such as cancer and in particular colorectal, breast, lung, prostate, pancreatic or bladder and renal cancer or leukemias or lymphomas.

Additionally a compound of formula (I), or a pharmaceutically acceptable salt thereof is provided for use in a method of treatment of a warm-blooded animal such as man by therapy. According to this aspect, there is provided a compound of formula (I) or a pharmaceutically acceptable salt thereof for use in the method of treating a human suffering from a disease in which the inhibition of one or more Aurora kinases is beneficial, comprising the steps of administering to a person in need thereof a therapeutically effective amount of a compound of formula (I) or a pharmaceutically acceptable salt thereof. In particular it is envisaged that inhibition of Aurora-A kinase and/or Aurora-B kinase may be beneficial. Preferably inhibition of Aurora-B kinase is beneficial. Further provided is a compound of formula (I) or a pharmaceutically acceptable salt thereof for use in the method of treating a human suffering from a hyperproliferative disease such as cancer and in particular particular colorectal, breast, lung, prostate, pancreatic or bladder and renal cancer or leukemias or lymphomas, comprising the steps of administering to a person in need thereof a therapeutically effective amount of a compound of formula (I) or a pharmaceutically acceptable salt thereof.

In another aspect of the invention, there is provided the use of a compound of formula (I) or a pharmaceutically acceptable salt thereof, in the preparation of a medicament for the treatment of a disease where the inhibition of one or more Aurora kinase is beneficial. In particular it is envisaged that inhibition of Aurora-A kinase and/or Aurora-B kinase may be beneficial. Preferably inhibition of Aurora-B kinase is beneficial. In another aspect of the invention, there is provided the use of a compound of formula (I) or a pharmaceutically acceptable salt thereof, in the preparation of a medicament for the treatment of hyperproliferative diseases such as cancer and in particular colorectal, breast, lung, prostate, pancreatic or bladder and renal cancer or leukemias or lymphomas.

For the above mentioned therapeutic uses the dose administered will vary with the compound employed, the mode of administration, the treatment desired, the disorder indicated and the age and sex of the animal or patient. The size of the dose would thus be calculated according to well known principles of medicine.

In using a compound of formula (I) for therapeutic or prophylactic purposes it will generally be administered so that a daily dose in the range, for example, 0.05 mg/kg to 50 mg/kg body weight is received, given if required in divided doses. In general lower doses will be administered when a parenteral route is employed. Thus, for example, for intravenous administration, a dose in the range, for example, 0.05 mg/kg to 25 mg/kg body weight will generally be used. Similarly, for administration by inhalation, a dose in the range, for example, 0.05 mg/kg to 25 mg/kg body weight will be used.

The treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine-threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex vivo and in vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In addition a compound of the invention may be used in combination with one or more cell cycle inhibitors. In particular with cell cycle inhibitors which inhibit bub1, bubR1 or CDK. Such conjoint treatment may be achieved by way of the simultaneous, sequential or separate dosing of the individual components of the treatment. Such combination products employ the compounds of this invention within the dosage range described hereinbefore and the other pharmaceutically active agent within its approved dosage range.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

The compounds of the invention inhibit the serine-threonine kinase activity of the Aurora kinases, in particular Aurora-A and/or Aurora-B and thus inhibit the cell cycle and cell proliferation. These properties may be assessed for example, using one or more of the procedures set out below. Whilst not wishing to be bound by theoretical constraints, it is believed that the compounds of formula (I) described herein may act as prodrugs. In procedures (c) and (d) set out below it is believed that a phosphonooxy group present in the compound of formula (I) is cleaved in situ to yield a hydroxy group and that such cleavage is necessary for activity is these assays.

(a) In Vitro Aurora-A Kinase Inhibition Test

This assay determines the ability of a test compound to inhibit serine-threonine kinase activity. DNA encoding Aurora-A may be obtained by total gene synthesis or by cloning. This DNA may then be expressed in a suitable expression system to obtain polypeptide with serine-threonine kinase activity. In the case of Aurora-A, the coding sequence was isolated from cDNA by polymerase chain reaction (PCR) and cloned into the BamH1 and Not1 restriction endonuclease sites of the baculovirus expression vector pFastBac HTc (GibcoBRL/Life technologies). The 5' PCR primer contained a recognition sequence for the restriction endonuclease BamH1 5' to the Aurora-A coding sequence. This allowed the insertion of the Aurora-A gene in frame with the 6 histidine residues, spacer region and rTEV protease cleavage site encoded by the pFastBac HTc vector. The 3' PCR primer replaced the Aurora-A stop codon with additional coding sequence followed by a stop codon and a recognition sequence for the restriction endonuclease Not1. This additional coding sequence (5' TAC CCA TAC GAT GTT CCA GAT TAC GCT TCT TAA 3') encoded for the polypeptide sequence YPYDVPDYAS. This sequence, derived from the influenza hemagglutin protein, is frequently used as a tag epitope sequence that can be identified using specific monoclonal antibodies. The recombinant pFastBac vector therefore encoded for an N-terminally 6 his tagged, C terminally influenza hemagglutin epitope tagged Aurora-A protein. Details of the methods for the assembly of recombinant DNA molecules can be found in standard texts, for example Sambrook et al. 1989, Molecular Cloning—A Laboratory Manual, $2^{nd}$ Edition, Cold Spring Harbor Laboratory press and Ausubel et al. 1999, Current Protocols in Molecular Biology, John Wiley and Sons Inc.

Production of recombinant virus can be performed following manufacturer's protocol from GibcoBRL. Briefly, the pFastBac-1 vector carrying the Aurora-A gene was transformed into *E. coli* DH10Bac cells containing the baculovirus genome (bacmid DNA) and via a transposition event in the cells, a region of the pFastBac vector containing gentamycin resistance gene and the Aurora-A gene including the baculovirus polyhedrin promoter was transposed directly into the bacmid DNA. By selection on gentamycin, kanamycin, tetracycline and X-gal, resultant white colonies should contain recombinant bacmid DNA encoding Aurora-A. Bacmid DNA was extracted from a small scale culture of several BH10Bac white colonies and transfected into *Spodoptera frugiperda* Sf21 cells grown in TC100 medium (GibcoBRL) containing 10% serum using CellFECTIN reagent (GibcoBRL) following manufacturer's instructions. Virus particles were harvested by collecting cell culture medium 72 hrs post transfection. 0.5 mls of medium was used to infect 100 ml suspension culture of Sf21s containing $1 \times 10^7$ cells/ml. Cell culture medium was harvested 48 hrs post infection and virus titre determined using a standard plaque assay procedure. Virus stocks were used to infect Sf9 and "High 5" cells at a multiplicity of infection (MOI) of 3 to ascertain expression of recombinant Aurora-A protein.

For the large scale expression of Aurora-A kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached $1.2 \times 10^6$ cells ml$^{-1}$ they were infected with plaque-pure Aurora-A recombinant virus at a multiplicity of infection of 1 and harvested 48 hours later. All subsequent purification steps were performed at 4° C. Frozen insect cell pellets containing a total of $2.0 \times 10^8$ cells were thawed and diluted with lysis buffer (25 mM HEPES (N-[2-hydroxyethyl]piperazine-N'-[2-ethanesulphonic acid]) pH7.4 at 4° C., 100 mM KCl, 25 mM NaF, 1 mM $Na_3VO_4$, 1 mM PMSF (phenylmethylsulphonyl fluoride), 2 mM 2-mercaptoethanol, 2 mM imidazole, 1 µg/ml aprotinin, 1 µg/ml pepstatin, 1 µg/ml leupeptin), using 1.0 ml per 3×10⁷ cells. Lysis was achieved using a dounce homogeniser, following which the lysate was centrifuged at 41,000 g for 35 minutes. Aspirated supernatant was pumped onto a 5 mm diameter chromatography column containing 500 µl Ni NTA (nitrilo-tri-acetic acid) agarose (Qiagen, product no. 30250) which had been equilibrated in lysis buffer. A baseline level of UV absorbance for the eluent was reached after washing the column with 12 ml of lysis buffer followed by 7 ml of wash buffer (25 mM HEPES pH7.4 at 4° C., 100 mM KCl, 20 mM imidazole, 2 mM 2-mercaptoethanol). Bound Aurora-A protein was eluted from the column using elution buffer (25 mM HEPES pH7.4 at 4° C., 100 mM KCl, 400 mM imidazole, 2 mM 2-mercaptoethanol). An elution fraction (2.5 ml) corresponding to the peak in WV absorbance was collected. The elution fraction, containing active Aurora-A kinase, was dialysed exhaustively against dialysis buffer (25 mM HEPES pH7.4 at 4° C., 45% glycerol (v/v), 100 mM KCl, 0.25% Nonidet P40 (v/v), 1 mM dithiothreitol).

Each new batch of Aurora-A enzyme was titrated in the assay by dilution with enzyme diluent (25 mM Tris-HCl pH7.5, 12.5 mM KCl, 0.6 mM DTT). For a typical batch, stock enzyme is diluted 1 in 666 with enzyme diluent and 20 µl of dilute enzyme is used for each assay well. Test compounds (at 10 mM in dimethylsulphoxide (DMSO) were diluted with water and 10 µof diluted compound was transferred to wells in the assay plates. "Total" and "blank" control wells contained 2.5% DMSO instead of compound. Twenty microliters of freshly diluted enzyme was added to all wells, apart from "blank" wells. Twenty microliters of enzyme diluent was added to "blank" wells. Twenty microliters of reaction mix (25 mM Tris-HCl, 78.4 mM KCl, 2.5 mM NaF, 0.6 mM dithiothreitol, 6.25 mM MnCl₂, 6.25 mM ATP, 7.5 µM peptide substrate [biotin-LRRWSLGLRRWSLGLRRWSLGLRRWSLG]) containing 0.2 µCi [γ³³P]ATP (Amersham Pharmacia, specific activity≧2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) and then assayed for incorporation of ³³P with a Beta plate counter. "Blank" (no enzyme) and "total" (no compound) control values were used to determine the dilution range of test compound which gave 50% inhibition of enzyme activity.

In this test, the compounds of the invention give 50% inhibition of enzyme activity at concentrations of 0.3 nM to 1000 nM and in particular compound 5 in Table 1 gave 50% inhibition of enzyme activity at a concentration of 5.5 nM.

(b) In Vitro Aurora-B Kinase Inhibition Test

This assay determines the ability of a test compound to inhibit serine-threonine kinase activity. DNA encoding Aurora-B may be obtained by total gene synthesis or by cloning. This DNA may then be expressed in a suitable expression system to obtain polypeptide with serine-threonine kinase activity. In the case of Aurora-B, the coding sequence was isolated from cDNA by polymerase chain reaction (PCR) and cloned into the pFastBac system in a manner similar to that described above for Aurora-A (i.e. to direct expression of a 6-histidine tagged Aurora-B protein).

For the large scale expression of Aurora-B kinase activity, Sf21 insect cells were grown at 28° C. in TC100 medium supplemented with 10% foetal calf serum (Viralex) and 0.2% F68 Pluronic (Sigma) on a Wheaton roller rig at 3 r.p.m. When the cell density reached 1.2×10⁶ cells ml⁻¹ they were infected with plaque-pure Aurora-B recombinant virus at a multiplicity of infection of 1 and harvested 48 hours later. All subsequent purification steps were performed at 4° C. Frozen insect cell pellets containing a total of 2.0×10⁸ cells were thawed and diluted with lysis buffer (50 mM HEPES (N-[2-hydroxyethyl]piperazine-N'-[2-ethanesulphonic acid]) pH7.5 at 4° C., 1 mM Na₃VO₄, 1 mM PMSF (phenylmethylsulphonyl fluoride), 1 mM dithiothreitol, 1 µg/ml aprotinin, 1 µg/ml pepstatin, 1 µg/ml leupeptin), using 1.0 ml per 2×10⁷ cells. Lysis was achieved using a sonication homogeniser, following which the lysate was centrifuged at 41,000 g for 35 minutes. Aspirated supernatant was pumped onto a 5 mm diameter chromatography column containing 1.0 ml CM sepharose Fast Flow (Amersham Pharmacia Biotech) which had been equilibrated in lysis buffer. A baseline level of UV absorbance for the eluent was reached after washing the column with 12 ml of lysis buffer followed by 7 ml of wash buffer (50 mM HEPES pH7.4 at 4° C., 1 mM dithiothreitol). Bound Aurora-B B protein was eluted from the column using a gradient of elution buffer (50 mM HEPES pH7.4 at 4° C., 0.6 M NaCl, 1 mM dithiothreitol, running from 0% elution buffer to 100% elution buffer over 15 minutes at a flowrate of 0.5 ml/min). Elution fractions (1.0 ml) corresponding to the peak in UV absorbance was collected. Elution fractions were dialysed exhaustively against dialysis buffer (25 mM HEPES pH7.4 at 4° C., 45% glycerol (v/v), 100 mM KCl, 0.05% (v/v) IGEPAL CA630 (Sigma Aldrich), 1 mM dithiothreitol). Dialysed fractions were assayed for Aurora-B kinase activity.

Each new batch of Aurora-B enzyme was titrated in the assay by dilution with enzyme diluent (25 mM Tris-HCl pH7.5, 12.5 mM KCl, 0.6 mM DTT). For a typical batch, stock enzyme is diluted 1 in 40 with enzyme diluent and 20 µl of dilute enzyme is used for each assay well. Test compounds (at 10 mM in dimethylsulphoxide (DMSO) were diluted with water and 10 µl of diluted compound was transferred to wells in the assay plates. "Total" and "blank" control wells contained 2.5% DMSO instead of compound. Twenty microliters of freshly diluted enzyme was added to all wells, apart from "blank" wells. Twenty microliters of enzyme diluent was added to "blank" wells. Twenty microliters of reaction mix (25 mM Tris-HCl, 78.4 mM KCl, 2.5 mM NaF, 0.6 mM dithiothreitol, 6.25 mM MnCl₂, 37.5 mM ATP, 25 µM peptide substrate [biotin-LRRWSLGLRRWSLGLRRWSLGLRRWSLG]) containing 0.2 µCi [γ³³P]ATP (Amersham Pharmacia, specific activity≧2500 Ci/mmol) was then added to all test wells to start the reaction. The plates were incubated at room temperature for 60 minutes. To stop the reaction 100 µl 20% v/v orthophosphoric acid was added to all wells. The peptide substrate was captured on positively-charged nitrocellulose P30 filtermat (Whatman) using a 96-well plate harvester (TomTek) and then assayed for incorporation of ³³P with a Beta plate counter. "Blank" (no enzyme) and "total" (no compound) control values were used to determine the dilution range of test compound which gave 50% inhibition of enzyme activity.

In this test, the compounds of the invention give 50% inhibition of enzyme activity at concentrations of 0.3 nM to 1000 nM and in particular compound 5 in Table 1 gave 50% inhibition of enzyme activity at a concentration of 1.6 nM.

(c) In Vitro Cell Proliferation Assay

This and other assays can be used to determine the ability of a test compound to inhibit the growth of adherent mammalian cell lines, for example the human tumour cell line SW620 (ATCC CCL-227). This assay determines the ability of at test compound to inhibit the incorporation of the thymidine analogue, 5'-bromo-2'-deoxy-uridine (BrdU) into cellular DNA. SW620 or other adherent cells were typically seeded at $1\times10^5$ cells per well in L-15 media (GIBCO) plus 5% foetal calf serum, 1% L-glutamine (100 µl/well) in 96 well tissue culture treated 96 well plates (Costar) and allowed to adhere overnight. The following day the cells were dosed with compound (diluted from 10 mM stock in DMSO using L-15 (with 5% FCS, 1% L-glutamine). Untreated control wells and wells containing a compound known to give 100% inhibition of BrdU incorporation were included on each plate. After 48 hours in the presence/absence of test compound the ability of the cells to incorporate BrdU over a 2 hour labelling period was determined using a Boehringer (Roche) Cell Proliferation BrdU ELISA kit (cat. No. 1 647 229) according to manufacturers directions. Briefly, 15 µl of BrdU labelling reagent (diluted 1:100 in media—L-15, 5% FCS, 1% L-glutamine) was added to each well and the plate returned to a humidified (+5% $CO_2$) 37° C. incubator for 2 hours. After 2 hours the labelling reagent was removed by decanting and tapping the plate on a paper towel. FixDenat solution (50 µl per well) was added and the plates incubated at room temperature for 45 minutes with shaking. The FixDenat solution was removed by decanting and tapping the inverted plate on a paper towel. The plate was then washed once with phosphate buffered saline (PBS) and 100 µl/well of Anti-BrdU-POD antibody solution (diluted 1:100 in antibody dilution buffer) added. The plate was then incubated at room temperature with shaking for 90 minutes. Unbound Anti-BrdU-POD antibody was removed by decanting and washing the plate 4 times with PBS before being blotted dry. TMB substrate solution was added (100 µl/well) and incubated for approximately 10 minutes at room temperature with shaking until a colour change was apparent. The optical density of the wells was then determined at 690 nm wavelength using a Titertek Multiscan plate reader. The values from compound treated, untreated and 100% inhibition controls were used to determine the dilution range of a test compound that gave 50% inhibition of BrdU incorporation. The compounds of the invention are active at 0.3 nM to 10000 nM in this test and in particular compound 5 in table 1 was active at 0.1 nM.

(d) In Vitro Cell Cycle Analysis Assay

This assay determines the ability of a test compound to arrest cells in specific phases of the cell cycle. Many different mammalian cell lines could be used in this assay and SW620 cells are included here as an example. SW620 cells were seeded at $7\times10^5$ cells per T25 flask (Costar) in 5 ml L-15 (5% FCS, 1% L-glutamine). Flasks were then incubated overnight in a humidified 37° C. incubator with 5% $CO_2$. The following day, 5 µl of L-15 (5% FCS, 1% L-glutamine) carrying the appropriate concentration of test compound solubilised in DMSO was added to the flask. A no compound control treatments was also included (0.5% DMSO). The cells were then incubated for a defined time (24 hours) with compound. After this time the media was aspirated from the cells and they were washed with 5 ml of prewarmed (37° C.) sterile PBSA, then detached from the flask by brief incubation with trypsin and followed by resuspension in 5 ml of 1% Bovine Serum Albumin (BSA, Sigma-Aldrich Co.) in sterile PBSA. The samples were then centrifuged at 2200 rpm for 10 minutes. The supernatant was aspirated to leave 200 µl of the PBS/BSA solution. The pellet was resuspended in this 200 µl of solution by pipetting 10 times to create a single cell suspension. One ml of ice-cold 80% ethanol was slowly added to each cell suspension and the samples stored at −20° C. overnight or until required for staining. Cells were pelleted by centrifugation, ethanol aspirated off and pellets resuspended in 200 µl PBS containing 100 µg/ml RNAse (Sigma Aldrich) and 10 µg/ml Propidium Iodide (Sigma Aldrich). Cell suspensions were incubated at 37° C. for 30 min, a further 200 µl PBS added and samples stored in the dark at 4° C. overnight.

Each sample was then syringed 10 times using 21-gauge needle. The samples were then transferred to LPS tubes and DNA content per cell analysed by Fluorescence activated cell sorting (FACS) using a FACScan flow cytometer (Becton Dickinson). Typically 30,000 events were counted and recorded using CellQuest v1.1 software (Verity Software). Cell cycle distribution of the population was calculated using Modfit software (Verity Software) and expressed as percentage of cells with 2N (G0/G1), 2N-4N(S phase) and with 4N (G2/M) DNA content.

The compounds of the invention are active in this test at 0.3 nM to 10000 nM.

The invention will now be illustrated in the following non limiting examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18-25° C. and in air unless stated, or unless the skilled person would otherwise operate under an atmosphere of an inert gas such as argon;

(iii) column chromatography (by the flash procedure) and medium pressure liquid chromatography (NPLC) were performed on Merck Kieselgel silica (Art. 9385);

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated dimethyl sulphoxide (DMSO $d_6$) (unless otherwise stated) on the delta scale (ppm downfield from tetramethylsilane) using one of the following four instruments Varian Gemini 2000 spectrometer operating at a field strength of 300 MHz Bruker DPX300 spectrometer operating at a field strength of 300 MHz JEOL EX 400 spectrometer operating at a field strength of 400 MHz Bruker Avance 500 spectrometer operating at a field strength of 500 MHz Peak multiplicities are shown as follows: s, singlet; d, doublet; dd, double doublet; t, triplet; q, quartet; qu, quintet; m, multiplet; br s, broad singlet.

(vi) robotic synthesis was carried out using a Zymate XP robot, with solution additions via a Zymate Master Laboratory Station and stirred via a Stem RS5000 Reacto-Station at 25° C.;

(vii) work up and purification of reaction mixtures from robotic synthesis was carried out as follows: evaporations were carried out in vacuo using a Genevac HT 4; column chromatography was performed using either an Anachem Sympur MPLC system on silica using 27 mm diameter columns filled with Merck silica (60 µm, 25 g); the structures of the final products were confirmed by LCMS on a Waters 2890/ZMD micromass system using the following and are quoted as retention time (RT) in minutes:

| Column: | waters symmetry C18 3.5 μm 4.6 × 50 mm |
|---|---|
| Solvent A: | H₂O |
| Solvent B: | CH₃CN |
| Solvent C: | methanol + 5% HCOOH |
| Flow rate: | 2.5 ml/min |
| Run time: | 5 minutes with a 4.5 minute gradient from 0-100% C |
| Wavelength: | 254 nm, bandwidth 10 nm |
| Mass detector: | ZMD micromass |
| Injection volume | 0.005 ml |

(viii) Analytical LCMS for compounds which had not been prepared by robotic synthesis was performed on a Waters Alliance HT system using the following and are quoted as retention time (RT) in minutes:

| Column: | 2.0 mm × 5 cm Phenomenex Max-RP 80A |
|---|---|
| Solvent A: | Water |
| Solvent B: | Acetonitrile |
| Solvent C: | Methanol/1% formic acid or Water/1% formic acid |
| Flow rate: | 1.1 ml/min |
| Run time: | 5 minutes with a 4.5 minute gradient from 0-95% B + constant 5% solvent C |
| Wavelength: | 254 nm, bandwidth 10 nm |
| Injection volume | 0.005 ml |
| Mass detector: | Micromass ZMD |

(ix) Preparative high performance liquid chromatography (HPLC) was performed on either Waters preparative LCMS instrument, with retention time (RT) measured in minutes:

| Column: | β-basic Hypercil (21 × 100 mm) 5 μm |
|---|---|
| Solvent A: | Water/0.1% Ammonium carbonate |
| Solvent B: | Acetonitrile |
| Flow rate: | 25 ml/min |
| Run time: | 10 minutes with a 7.5 minute gradient from 0-100% B |
| Wavelength: | 254 nm, bandwidth 10 nm |
| Injection volume | 1-1.5 ml |
| Mass detector: | Micromass ZMD |

Gilson preparative HPLC instrument, with retention time (RT) measured in minutes:

| Column: | 21 mm × 15 cm Phenomenex Luna2 C18 |
|---|---|
| Solvent A: | Water + 0.2% trifluoracetic acid, |
| Solvent B: | Acetonitrile + 0.2% trifluoracetic acid |
| Flow rate: | 21 ml/min |
| Runtime: | 20 minutes with various 10 minute gradients from 5-100% B |
| Wavelength: | 254 nm, bandwidth 10 nm |
| Injection volume | 0.1-4.0 ml |

(x) intermediates were not generally fully characterised and purity was assessed by thin layer chromatography (TLC), HPLC, infra-red (IR), MS or NMR analysis.

Particular examples of compounds of formula (I) are set out in the following tables, in which * represents the point of attachment of the groups in each table to the compound of formula (I) above each table:

TABLE 1

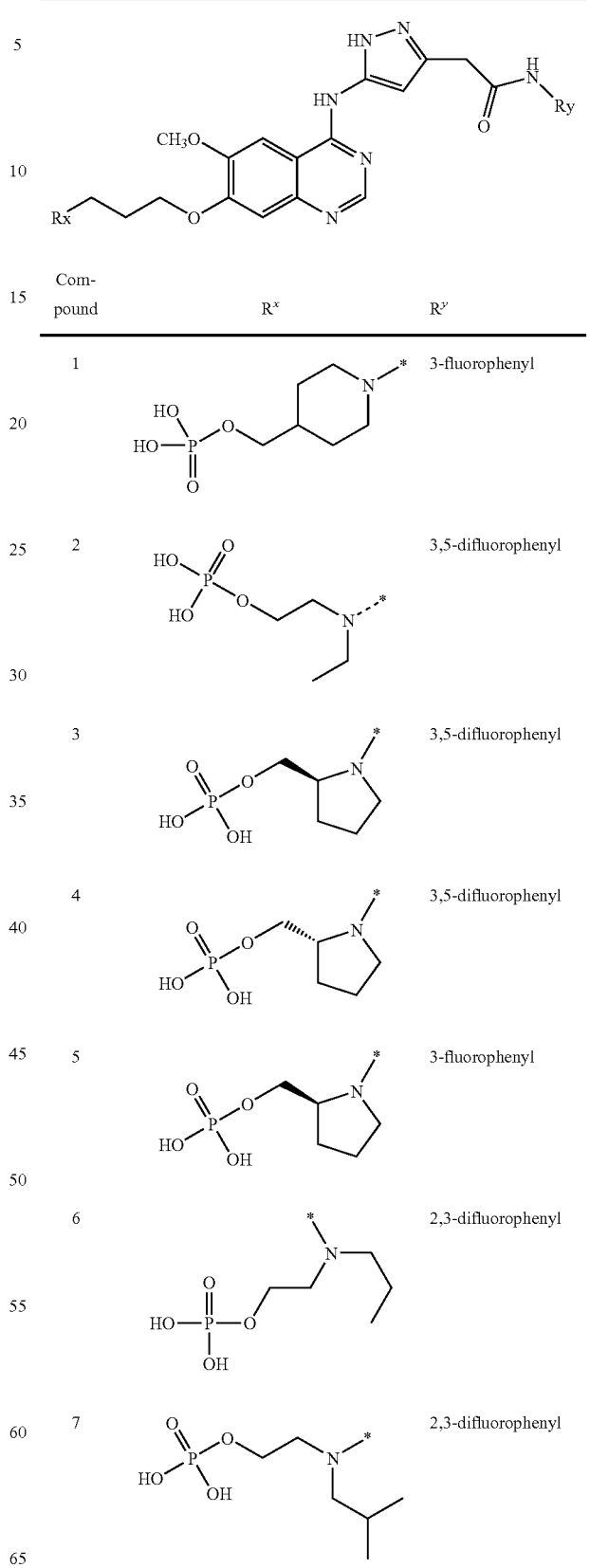

| Compound | $R^x$ | $R^y$ |
|---|---|---|
| 1 | 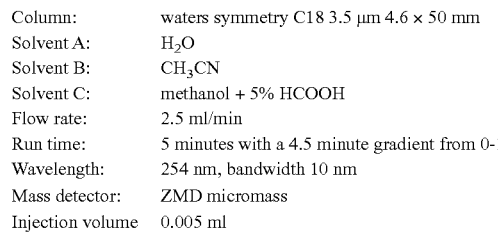 | 3-fluorophenyl |
| 2 | 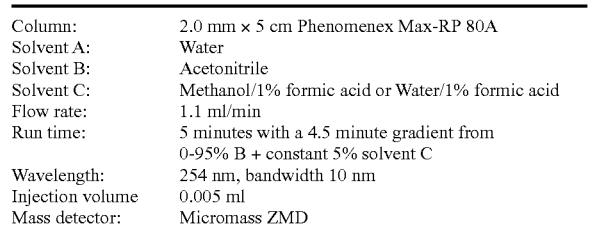 | 3,5-difluorophenyl |
| 3 | 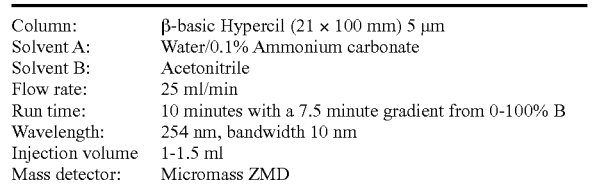 | 3,5-difluorophenyl |
| 4 | 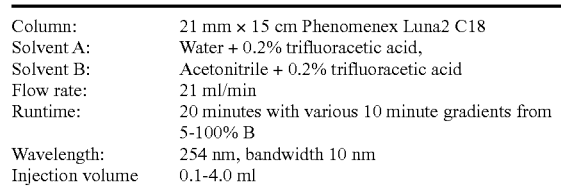 | 3,5-difluorophenyl |
| 5 | | 3-fluorophenyl |
| 6 | | 2,3-difluorophenyl |
| 7 | | 2,3-difluorophenyl |

TABLE 1-continued

| Compound | R$^x$ | R$^y$ |
|---|---|---|
| 8 | phosphate-O-CH2CH2-N(isobutyl)-* | 3,5-difluorophenyl |
| 9 | phosphate-O-CH2CH2-N(propyl)-* | 3,5-difluorophenyl |
| 10 | *-N(isobutyl)-CH2CH2-O-phosphate | 3-fluorophenyl |
| 11 | phosphate-O-CH2CH2-N(neopentyl)-* | 3-fluorophenyl |
| 12 | 1-*-piperidin-3-yl-O-phosphate | 3-fluorophenyl |
| 13 | (S)-1-*-pyrrolidin-2-yl-CH2-O-phosphate | 2,3-difluorophenyl |
| 14 | phosphate-O-CH2CH2-N(propargyl)-* | 3,5-difluorophenyl |
| 15 | phosphate-O-CH2CH2-N(isopropyl)-* | 2,3-difluorophenyl |
| 16 | phosphate-O-CH2CH2-N(propargyl)-* | 2,3-difluorophenyl |
| 17 | phosphate-O-CH2CH2-N(CH2CH2OCH3)-* | 2,3-difluorophenyl |
| 18 | phosphate-O-CH2CH2-NH-* | 3-fluorophenyl |
| 19 | phosphate-O-CH2CH2-N(CH2-cyclobutyl)-* | 2,3-difluorophenyl |
| 20 | phosphate-O-CH2CH2-N(CH2CH2CF3)-* | 3-fluorophenyl |
| 21 | phosphate-O-CH2CH2-N(allyl)-* | 2,3-difluorophenyl |
| 22 | phosphate-O-CH2CH2-N(cyclobutyl)-* | 2,3-difluorophenyl |

TABLE 1-continued

| Compound | Rˣ | Rʸ |
|---|---|---|
| 23 | N-cyclopentyl, CH₂CH₂-O-P(O)(OH)₂ | 2,3-difluorophenyl |
| 24 | N-cyclopropyl, CH₂CH₂-O-P(O)(OH)₂ | 3-fluorophenyl |
| 25 | N-(cyclopropylmethyl), CH₂-O-P(O)(OH)₂ | 2,3-difluorophenyl |
| 26 | N-cyclobutyl, CH₂CH₂-O-P(O)(OH)₂ | 3-fluorophenyl |

TABLE 2

| Compound | Rˣ | Rʸ |
|---|---|---|
| 27 | CH₂CH₂-O-P(O)(OH)₂ | 2,3-difluorophenyl |

TABLE 3

| Compound | Rˣ | Rʸ |
|---|---|---|
| 28 | N-ethyl, CH₂CH₂-O-P(O)(OH)₂ | 2,3-difluorophenyl |
| 29 | N-isopropyl, CH₂CH₂-O-P(O)(OH)₂ | 2,3-difluorophenyl |
| 30 | NH-C(CH₃)₂-CH₂CH₂-O-P(O)(OH)₂ | 2,3-difluorophenyl |
| 31 | (S)-2-pyrrolidinyl-CH₂CH₂-O-P(O)(OH)₂ | 2,3-difluorophenyl |
| 32 | (S)-2-pyrrolidinyl-CH₂-O-P(O)(OH)₂ | 2,3-difluorophenyl |
| 33 | N-propyl, CH₂CH₂-O-P(O)(OH)₂ | 2,3-difluorophenyl |
| 34 | N-butyl, CH₂CH₂-O-P(O)(OH)₂ | 2,3-difluorophenyl |
| 35 | N-cyclopentyl, CH₂CH₂-O-P(O)(OH)₂ | 2,3-difluorophenyl |

TABLE 3-continued

| Compound | Rx | Ry |
|---|---|---|
| 36 | (S)-pyrrolidin-2-ylmethyl phosphate | 2,3-difluorophenyl |
| 37 | (S)-pyrrolidin-2-ylmethyl phosphate | 3-fluorophenyl |
| 38 | 2-(cyclopentylamino)ethyl phosphate | 3-fluorophenyl |
| 39 | 2-(ethylamino)ethyl phosphate | 3-fluorophenyl |
| 40 | 3-amino-3-methylbutyl phosphate | 3-fluorophenyl |
| 41 | 2-(propylamino)ethyl phosphate | 3-fluorophenyl |
| 42 | (R)-pyrrolidin-2-ylmethyl phosphate | 3-fluorophenyl |
| 43 | 3-(ethylamino)propyl phosphate | 3-fluorophenyl |

TABLE 3-continued

| Compound | Rx | Ry |
|---|---|---|
| 44 | 2-((2-methoxyethyl)amino)ethyl phosphate | 3-fluorophenyl |

TABLE 4

| Compound | Rx | Ry |
|---|---|---|
| 45 | 2-(propylamino)ethyl phosphate | 2,3-difluorophenyl |
| 46 | 2-(ethylamino)ethyl phosphate | 2,3-difluorophenyl |
| 47 | (S)-pyrrolidin-2-ylmethyl phosphate | 2,3-difluorophenyl |

TABLE 4-continued

| Compound | Rx | Ry |
|---|---|---|
| 48 | ![structure with phosphate-ethyl-N-methyl] | 2,3-difluorophenyl |
| 49 | ![structure with phosphate-methyl-pyrrolidinyl] | 2,3-difluorophenyl |

TABLE 5

| Compound | Rx | Ry |
|---|---|---|
| 50 | ![structure with phosphate-ethyl-N-ethyl] | 3-fluorophenyl |

EXAMPLE 1

Preparation of Compound 1 in Table 1—{1-[3-({4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl dihydrogen phosphate Di(tert-butyl) {1-[3-({4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl phosphate (400 mg, 0.53 mmol) was suspended in dioxane (20 ml) and treated with a solution of hydrochloric acid (4.0 N) in dioxane (795 μl, 3.18 mmol) at ambient temperature for 15 hours. The solid was recovered by filtration, washed with dioxane, dried in vacuo at 50° C. to yield compound 1 in table 1 (360 mg, 94% yield):

$^1$H-NMR (DMSO $d_6$, AcOD): 8.88 (s, 1H), 8.27 (s, 1H), 7.61 (m, 1H), 7.35 (m, 3H), 6.84 (m, 1H), 6.81 (s, 1H), 4.28 (m, 2H), 3.98 (s, 3H), 3.83 (s, 2H), 3.75 (t, 2H), 3.58 (d, 2H), 3.26 (m, 2H), 3.26 (m, 2H), 2.32 (m, 2H), 1.85 (m, 3H), 1.54 (m, 2H):

MS (+ve ESI): 644.5 (M+H)$^+$.

Di(tert-butyl) {1-[3-({4-[(5-{2-[(3-fluorophenyl)amino]-2-oxoethyl}-1H-pyrazol-3-yl)amino]-6-methoxyquinazolin-7-yl}oxy)propyl]piperidin-4-yl}methyl phosphate, used as the starting material, was obtained as follows:

a) A mixture of 4-benzyloxy-3-methoxybenzaldehyde (157 g, 649 mmol), sodium acetate (106 g, 1.29 mol), hydroxylamine hydrochloride (90 g, 1.29 mol) and acetic acid (500 ml) was refluxed for 21 hours. The solvent was evaporated and ice/water (1000 ml) was added to the residue forming a sticky solid. The mixture was neutralised with aqueous sodium hydroxide solution then extracted with dichloromethane (2×500 ml). The organic solution was washed with 1.0 N sodium hydroxide (100 ml), brine (100 ml) and then dried over magnesium sulphate. Solvent evaporation, trituration of the residue with hexane:ethyl acetate (3:1) and collection of the solid by vacuum filtration yielded 4-benzyloxy-3-methoxybenzonitrile (123 g, 80% yield) as a brown solid:

$^1$H-NMR (DMSO $d_6$): 7.38 (m, 7H), 7.19 (m, 1H), 5.18 (s, 2H), 3.80 (s, 3H): MS (−ve ESI): 238 (M−H)$^−$.

b) Acetic acid (17 ml) was added slowly to nitric acid (40 ml, 440 mmol) at 5° C. Powdered 4-benzyloxy-3-methoxybenzonitrile (10 g, 42 mmol) was added and the mixture warmed to 23° C. over 10 minutes. An exotherm occurred and the temperature was controlled at <30° C. using an ice bath. The mixture was stirred at 23° C. for 20 hours then poured into ice/water (1000 ml). After stirring for two hours the yellow solid was collected by suction filtration, washed with water and dried to yield 4-benzyloxy-3-methoxy-6-nitrobenzonitrile (10.1 g, 85% yield) as a yellow solid:

$^1$H-NMR (DMSO $d_6$): 7.95 (s, 1H), 7.70 (s, 1H), 7.40 (m, 5H), 5.30 (s, 2H), 3.95 (s, 3H):

MS (−ve ESI): 283 (M−H)$^−$.

c) A mixture of 4-benzyloxy-3-methoxy-6-nitrobenzonitrile (46 g, 162 mmol), sodium bicarbonate (95 g, 1.13 mol), water (750 ml), dichloromethane (550 ml) and tetrabutylammonium chloride (30 g, 108 mmol) was rapidly stirred at 20° C. and treated with sodium dithionite (66 g, 379 mmol) portionwise over 2 hours. The mixture was stirred for a further hour then the phases separated. The aqueous phase was extracted with dichloromethane (2×200 ml) and the combined organic solution washed with water (300 ml) and dried over magnesium sulphate. The solution was concentrated to 250 ml and 4.0 M hydrochloric acid in 1,4-dioxane (150 ml, 0.6 mol) added, then diluted with diethyl ether (1000 ml) and cooled on ice. The resulting solid was collected by vacuum filtration and washed with diethyl ether. The solid was stirred in methanol (1000 ml) and sodium bicarbonate solution (800 ml) added to pH 8 and stirred for 1 hour. The solid was collected by vacuum filtration, washed with water then methanol and dried in vacuo to yield 2-amino-4-(benzyloxy)-5-methoxybenzonitrile (34 g, 82% yield) as light brown solid:

$^1$H-NMR (DMSO $d_6$): 7.40 (m, 5H), 6.90 (s, 1H), 6.50 (s, 1H), 5.60 (br s, 2H), 5.02 (s, 2H), 3.65 (s, 3H):

MS (+ve ESI): 254 (M+H)$^+$.

d) 2-amino-4-(benzyloxy)-5-methoxybenzonitrile (100 g, 394 mmol) in toluene (1400 ml) was treated with dimethylformamide dimethylacetal (100 ml, 940 mmol) at reflux with slow distillation of solvent to maintain the internal temperature at 105° C. After 3 hours the solution was cooled and filtered to remove a small amount of solid. The filtrate was evaporated in vacuo and the residue triturated with diethyl ether and the solid collected by vacuum filtration and dried in vacuo to yield N'-(5-(benzyloxy)-2-cyano-4-methoxyphenyl) -N,N-dimethylimidoformamide (110 g, 90% yield) as a brown solid:

$^1$H-NMR (DMSO d$_6$): 7.90 (s, 1H), 7.40 (m, 5H), 7.10 (s, 1H), 6.88 (s, 1H), 5.15 (s, 2H), 3.70 (s, 3H), 3.02 (s, 3H), 2.95 (s, 3H):

MS (+ve ESI): 310 (M+H)$^+$
MS (−ve ESI): 308 (M−H)$^-$.

e) N-(5-(benzyloxy)-2-cyano-4-methoxyphenyl)-N,N-dimethylimidoformamide (110 g, 356 mmol) and trifluoroacetic acid (600 ml) were refluxed together for 15 min. Evaporation and co-evaporation with toluene, trituration with diethyl ether and collection of the solid by vacuum filtration and drying in vacuo yielded N'-(2-cyano-5-hydroxy-4-methoxyphenyl) -N,N-dimethylimidoformamide (112 g, 95% yield) as a light brown trifluoroacetate salt:

$^1$H-NMR (DMSO d$_6$): 8.39 (s, 1H), 7.38 (s, 1H), 6.90 (s, 1H), 3.80 (s, 3H), 3.25 (s, 3H), 3.17 (s, 3H):

MS (+ve ESI): 220 (M+H)$^+$
MS (−ve ESI): 218 (M−H)$^-$.

f) A mixture of N'-(2-cyano-5-hydroxy-4-methoxyphenyl)-N,N-dimethylimidoformamide (21.9 g, 66 mmol), cesium carbonate (998 g, 300 mmol) and 1-bromo-3-chloropropane (11 ml, 110 mmol) in acetonitrile (300 ml) was refluxed for 1 hour. The reaction mixture was cooled and the solvent evaporated in vacuo. The residue in water (200 ml) was extracted with dichloromethane (2×150 ml). The organic solution was washed with brine (50 ml) and dried over magnesium sulphate. Solvent was evaporated in vacuo and the residue triturated with diethyl ether. The solid was collected by vacuum filtration and dried in vacuo to yield N'-(5-(3-chloropropoxy)-2-cyano-4-methoxyphenyl) -N,N-dimethylimidoformamide (17.7 g, 91% yield) as a white solid:

$^1$H-NMR (DMSO d$_6$): 8.89 (s, 1H), 7.07 (s, 1H), 6.75 (s, 1H), 4.15 (t, 2H), 3.77 (t, 2H), 3.70 (s, 3H), 3.05 (s, 3H), 2.95 (s, 3H), 2.18 (m, 2H):

MS (+ve ESI): 296.4 (M+H)$^+$.

g) N'-(5-(3-chloropropoxy)-2-cyano-4-methoxyphenyl)-N,N-dimethylimidoformamide (230 mg, 0.78 mmol) in acetic acid (0.7 ml) was reacted with methyl (5-amino-1H-pyrazol-3-yl)acetate (CAS 174891-10-2; WO 95/33724) (110 mg, 0.74 mmol) at reflux for 1 hour. The mixture was cooled, the acetic acid evaporated, and the residue purified by chromatography on silica gel, eluting with dichloromethane/1% methanolic ammonia (90:10), to give methyl (5-((7-(3-chloropropoxy)-6-methoxyquinazolin-4-yl)amino)-1H-pyrazol-3-yl)acetate (219 mg, 69% yield) as a cream solid:

$^1$H-NMR (DMSO d$_6$, TFA): 8.93 (s, 1H), 8.28 (s, 1H), 7.32 (s, 1H), 6.80 (s, 1H), 4.02 (m, 2H), 4.00 (s, 3H), 3.75-3.85 (m, s, 4H), 3.65 (s, 3H), 2.30 (m, 2H), 1.90 (s, 3H):

MS (+ve ESI): 406.5 (M+H)$^+$.

h) Methyl (5-((7-(3-chloropropoxy)-6-methoxyquinazolin-4-yl)amino)-1H-pyrazol-3-yl)acetate (100 mg, 0.247 mmol) in tetrahydrofuran (1.2 ml)/water (0.6 ml), was reacted with lithium hydroxide (21 mg, 0.493 mmol) at ambient temperature over night. The mixture was acidified with 6.0 N hydrochloric acid to pH 4 and the solid was recovered by filtration, washed with water and dried to give (5-((7-(3-chloropropoxy)-6-methoxyquinazolin-4-yl) amino)-1H-pyrazol-3-yl)acetic acid (72 mg, 75% yield) as a beige solid:

$^1$H-NMR (DMSO d$_6$, TFA): 8.95 (s, 1H), 8.28 (s, 1H), 7.32 (s, 1H), 6.80 (s, 1H), 4.33 (m, 2H), 4.00 (s, 3H), 3.83 (m, 2H), 3.74 (s, 2H), 2.40-2.50 (m, 2H):

MS (+ve ESI): 392.5, 394.5 (M+H)$^+$.

i) (5-((7-(3-chloropropoxy)-6-methoxyquinazolin-4-yl) amino)-1H-pyrazol-3-yl) acetic acid (7.83 g, 20 mmol) in dimethylformamide (78 ml) was reacted with 3-fluoroaniline (2.44 g, 22 mmol) in the presence of 1-(3-dimethylamino-propyl)-3-ethylcarbodiimide hydrochloride (4.2 g, 22 mmol), 2-hydroxypyridin-1-oxide (2.22 g, 20 mmol) and diisopropylethylamine (2.8 g, 22 mmol) at 50° C. for 1.7 hours. The solvent was removed by evaporation under vacuum, the residue was triturated with water (twice), and purified by silica gel chromatography, eluting with dichloromethane:methanol (95:3 to 85:15) to give 2-(5-((7-(3-chloropropoxy)-6-methoxyquinazolin-4-yl) amino)-1H-pyrazol-3-yl)-N-(3-fluorophenyl) acetamide (4.5 g, 46% yield) as a beige solid:

$^1$H-NMR (DMSO d$_6$): 8.47 (s, 1H), 8.02 (s, 1H), 7.60-7.68 (m, 1H), 7.30-7.41 (m, 2H), 7.20 (s, 1H), 6.88 (m, 1H), 6.84 (s, 1H), 4.27 (m, 2H), 3.96 (s, 3H), 3.84 (m, 2H), 3.78 (s, 2H), 2.26 (m, 2H):

MS (+ve ESI): 485.6 (M+H)$^+$.

j) Piperidin-4-ylmethanol (115 mg, 1 mmol) was added to a solution of 2-(5-((7-(3-chloropropoxy)-6-methoxyquinazolin-4-yl)amino)-1H-pyrazol-3-yl)-N-(3-fluorophenyl) acetamide (121 mg, 0.25 mmol) in dimethylacetamide (1 ml) and the reaction was heated at 90° C. for 9 hours. The reaction was cooled to ambient temperature and the volatile substances removed in vacuo. Purification by reverse phase hplc yielded N-(3-fluorophenyl)-2-{3-[(7-{3-[4(hydroxymethyl)piperidin-1-yl]propoxy}-6-methoxyquinazolin-4-yl)amino]-1H-pyrazol-5-yl}acetamide (80 mg, 57% yield) as an off-white solid:

$^1$H-NMR (DMSO d$_6$, TFA): 8.96 (s, 1H), 8.30 (s, 1H), 7.63 (m, 1H), 7.36 (m, 3H), 6.90 (m, 1H), 6.84 (s, 1H), 4.30 (t, 2H), 4.01 (s, 3H), 3.85 (m, 2H), 3.62 (d, 2H), 3.32 (d, 2H), 3.27 (m, 2H), 2.98 (t, 2H), 2.29 (m, 2H), 1.90 (d, 2H), 1.67 (m, 1H), 1.42 (m, 2H):

MS (+ve ESI): 564.6 (M+H)$^+$.

k) N-(3-fluorophenyl)-2-{3-[(7-{3-[4-(hydroxymethyl)piperidin-1-yl]propoxy}-6-methoxyquinazolin-4-yl)amino]-1H-pyrazol-5-yl}acetamide (450 mg, 1 mmol) was dissolved in dimethylformamide (2 ml), tetrazole (224 mg, 4 mmol) and di-tert-butyl-diethyl-phosphoramidite (479 µl, 2 mmol) were added to the mixture at ambient temperature, and stirring was continued for 3 hours under argon. The reaction mixture was then cooled to −60° C. and a solution of monoperoxyphthalic acid magnesium salt (297 mg, 0.6 mmol) in dimethylformamide (1.5 ml) was slowly added to the reaction mixture. This mixture was then stirred for 1.5 hours at 60° C., sodium metabisulphite (1.5 g, 10 mmol) in solution in water (2 ml) was then added and the reaction mixture was slowly allowed to warm to ambient temperature, evaporated, and the residue was purified by silica gel chromatography, eluting with dichloromethane: 3.0 N methanolic ammonia (100:0 to 92:8), to give di(tert-butyl) {1-[3-({4-[(5-{2-[(3-fluorophenyl)amino]-2-oxoethyl}-1H-pyrazol-3-yl)amino]-6-methoxyquinazolin-7-yl}oxy) propyl]piperidin-4-yl}methyl phosphate (420 mg, 70% yield) as a cream solid:

$^1$H-NMR (DMSO d$_6$): 8.46 (s, 1H), 7.99 (s, 1H), 7.63 (d, 1H), 7.36 (m, 2H), 7.35 (s, 1H), 7.15 (s, 1H), 6.90 (m, 1H), 6.88 (s, 1H), 4.17 (t, 2H), 3.95 (s, 3H), 3.77 (s, 2H), 3.72 (t, 2H), 2.91 (d, 2H), 2.46 (t, 2H), 1.96 (m, 4H), 1.65 (m, 2H), 1.58 (m, 1H), 1.41 (s, 18H), 1.25 (m, 2H):

MS (+ve ESI): 756.6 (M+H)$^+$.

EXAMPLE 2

Preparation of Compound 2 in Table 1—2-[[3-({4-[(5-{2-[(3,5-difluorophenyl)amino]-2-oxoethyl}-1H-pyrazol-3-yl)amino]-6-methoxyquinazolin-7-yl}oxy)propyl](ethyl)amino]ethyl dihydrogen phosphate An analogous reaction to that described in example 1, but starting with di(tert-butyl) 2-[[3-({4-[(5-{2-[(3,5-difluorophenyl)amino-]-2-oxoethyl}-1H-pyrazol-3-yl)amino]-6-methoxyquinazolin-7-yl}oxy)propyl](ethyl)amino]ethyl phosphate (320 mg, 0.428 mmol) yielded compound 2 in table 1 (260 mg, 86% yield) as an off-white solid:

$^1$H-NMR (DMSO $d_6$, $CD_3COOD$): 8.92 (s, 1H), 8.31 (s, 1H), 7.41 (m, 3H), 6.88 (t, 1H), 6.84 (s, 1H), 4.32 (m, 4H), 3.97 (s, 3H), 3.89 (s, 2H), 3.42 (m, 6H), 2.32 (m, 2H), 1.31 (t, 3H):

MS (+ve ESI): 636.4 (M+H)$^+$.

Di(tert-butyl) 2-[[3-({4-[(5-{2-[(3,5-difluorophenyl)amino]-2-oxoethyl}-1H-pyrazol-3-yl)amino]-6-methoxyquinazolin-7-yl}oxy)propyl](ethyl)amino]ethyl phosphate, used as the starting material, was obtained as follows:

a) A suspension of 3-{[7-(3-chloropropoxy)-6-methoxyquinazolin-4-yl]amino}-1H-pyrazol-5-yl)acetic acid (3.91 g, 10 mmol) in dimethylformamide (20 ml) was reacted with 3,5-difluoroaniline (1.42 g, 11 mmol) in the presence of 1-(3-dimethylaminopropyl)-3-ethylcarbodiimide hydrochloride (2.01 g, 10.5 mmol) and 2-hydroxypyridine-1-oxide (1.11 g, 10 mmol) at 60° C. for 1.75 hours. The solvent was evaporated in vacuo and the residue was triturated twice with water. The resulting wet paste was dissolved in a mixture of dichloromethane:water (80:20), adsorbed onto silica gel and purified by chromatography on silica gel, eluting with dichloromethane:methanol (95:5 to 85:15) to give 2-(5-((7-(3-chloropropoxy)-6-methoxyquinazolin-4-yl)amino)-1H-pyrazol-3-yl)-N-(3,5-difluorophenyl) acetamide (2.45 g, 49% yield) as a beige solid:

$^1$H-NMR (DMSO $d_6$): 8.47 (s, 1H), 8.02 (s, 1H), 7.36 (m, 2H), 7.20 (s, 1H), 6.94 (t, 1H), 6.84 (s, 1H), 4.27 (m, 2H), 3.96 (s, 3H), 3.83 (m, 2H), 3.79 (s, 2H), 2.27 (m, 2H):

MS (+ve ESI): 503.5, 505.5 (M+H)$^+$.

b) An analogous reaction to that described in example 1j, but starting with 2-(ethylamino)ethanol (89 mg, 1 mmol) and 2-(5-((7-(3-chloropropoxy)-6-methoxyquinazolin-4-yl)amino)-1H-pyrazol-3-yl)-N-(3,5-difluorophenyl) acetamide (130 mg, 0.26 mmol) yielded N-(3,5-difluorophenyl)-2-{3-[(7-{3-[ethyl(2-hydroxyethyl)amino]propoxy}-6-methoxyquinazolin-4-yl)amino]-1H-pyrazol-5-yl}acetamide (124 mg, 86% yield) as an off-white solid:

$^1$H-NMR (DMSO $d_6$, TFA): 8.96 (s, 1H), 8.30 (s, 1H), 7.35 (m, 2H), 7.33 (s, 1H), 6.90 (m, 1H), 6.84 (s, 1H), 4.30 (m, 2H), 4.01 (s, 3H), 3.86 (s, 2H), 3.78 (t, 2H), 3.30 (m, 6H), 2.29 (m, 2H), 1.27 (t, 3H):

MS (+ve ESI): 556.5 (M+H)$^+$.

c) An analogous reaction to that described in example 1k, but starting with N-(3,5-difluorophenyl)-2-{3-[(7-{3-[ethyl(2-hydroxyethyl)amino]propoxy}-6-methoxyquinazolin-4-yl)amino]-1H-pyrazol-5-yl}acetamide (400 mg, 0.72 mmol) yielded di(tert-butyl) 2-[[3-({4-[(5-{2-[(3,5-difluorophenyl)amino]-2-oxoethyl}-1H-pyrazol-3-yl)amino]-6-methoxyquinazolin-7-yl}oxy)propyl](ethyl)amino]ethyl phosphate (320 mg, 60% yield) as an off-white solid: tk $^1$H-NMR (DMSO $d_6$): 8.36 (s, 1H), 7.88 (s, 1H), 7.26 (m, 2H), 7.04 (s, 1H), 6.83 (t, 2H), 6.73 (s, 1H), 4.07 (m, 2H), 3.85 (s, 3H), 3.77 (q, 2H), 2.68 (s, 2H), 2.55 (m, 4H), 2.43 (m, 2H), 1.81 (m, 2H), 0.88 (t, 3H):

MS (+ve ESI): 748.5 (M+H)$^+$.

EXAMPLE 3

Preparation of Compound 3 in Table 1—{(2S)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate An analogous reaction to that described in example 1, but starting with di(tert-butyl) {(2S)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl phosphate (130 mg, 0.171 mmol) yielded compound 3 in table 1 (91 mg, 74% yield):

$^1$H-NMR (DMSO $d_6$, $CD_3COOD$): 8.91 (s, 1H), 8.29 (s, 1H), 7.40 (m, 3H), 6.89 (t, 1H), 6.82 (s, 1H), 4.31 (m, 2H), 4.20 (m, 2H), 4.00 (s, 3H), 3.88 (s, 2H), 3.80 (m, 1H), 3.70 (m, 1H), 3.60 (m, 1H), 3.28 (m, 1H), 3.23 (m, 1H), 2.30 (m, 2H), 2.20 (m, 1H), 2.03 (m, 1H), 1.95 (m, 1H), 1.82 (m, 1H):

MS (+ve ESI): 648.3 (M+H)$^+$.

di(tert-butyl) {(2S)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl phosphate, used as the starting material, was obtained as follows:

a) An analogous reaction to that described in example 2b, but starting with L-prolinol (101 mg, 1 mmol) yielded N-(3,5-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide (85 mg, 57% yield) as an off-white solid:

$^1$H-NMR (DMSO $d_6$, TFA): 8.96 (s, 1H), 8.30 (s, 1H), 7.30-7.40 (m, 3H), 6.85-6.95 (m, 1H), 6.84 (s, 1H), 4.30 (m, 2H), 4.01 (s, 3H), 3.86 (s, 2H), 3.72-3.82 (m, 1H), 3.50-3.70 (m, 4H), 3.15-3.30 (m, 2H), 2.25-2.40 (m, 2H), 1.95-2.20 (m, 2H), 1.85-1.95 (m, 1H), 1.70-1.85 (m, 1H):

MS (+ve ESI): 568.6 (M+H)$^+$.

b) N-(3,5-difluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide (650 mg, 1.14 mmol) was dissolved in dimethylacetamide (4 ml). Tetrazole (160 mg, 2.3 mmol) and di-tert-butyl-diethylphosphoramidite (637 µl, 2.3 mmol) were added to the mixture and stirring was continued at ambient temperature under argon for 3 hours. The reaction mixture was then diluted with dichloromethane (50 ml) and washed with a saturated solution of sodium bicarbonate. The organic phase was recovered, dried over magnesium sulphate, filtered and concentrated. The crude product was dissolved in tetrahydrofuran (18 ml) at 0° C. and hydrogen peroxide (30%, 335 µl) was added to the solution, which was stirred for 15 hours at ambient temperature. The mixture was then cooled to 0° C. and sodium metabisulphite (1.08 g) in water (5 ml) was added at 0° C., and the reaction was allowed to warm to ambient temperature. The mixture was diluted with ethyl acetate (50 ml), washed with a saturated solution of sodium bicarbonate. The organic phase was recovered, dried over magnesium sulphate, filtered and concentrated in vacuo. The crude product was purified by chromatography on silica gel, eluting with dichloromethane:methanol: 3.0 N methanolic ammonia (95:5:0 to 95:0:5), to give di(tert-butyl) {(2S)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl phosphate (133 mg, 15% yield) as an off-white solid:

¹H-NMR (DMSO d₆): 8.44 (s, 1H), 7.96 (s, 1H), 7.35 (m, 2H), 7.13 (s, 1H), 6.92 (m, 1H), 6.82 (s, 1H), 4.18 (m, 2H), 3.93 (s, 3H), 3.75 (m, 3H), 3.56 (m, 1H), 3.08 (m, 1H), 2.92 (m, 1H), 2.67 (m, 1H), 2.46 (m, 1H), 2.20 (q, 1H), 1.95 (m, 2H), 1.83 (m, 1H), 1.68 (m, 2H), 1.59 (m, 1H), 1.38 (s, 18H):

MS (+ve ESI): 760.5 (M+H)⁺.

EXAMPLE 4

Preparation of Compound 4 in Table 1—{(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate An analogous reaction to that described in example 1, but starting with di(tert-butyl) {(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl phosphate (350 mg, 0.46 mmol) yielded compound 4 in table 1 (305 mg, 92% yield) as an off-white solid:

¹H-NMR (DMSO d₆): 8.90 (s, 1H), 8.29 (s, 1H), 7.40 (m, 3H), 6.87 (t, 1H), 6.81 (s, 1H), 4.31 (m, 2H), 4.20 (m, 2H), 4.00 (s, 3H), 3.88 (s, 2H), 3.80 (m, 1H), 3.70 (m, 1H), 3.60 (m, 1H), 3.28 (m, 1H), 3.23 (m, 1H), 2.32 (m, 2H), 2.20 (m, 1H), 2.04 (m, 1H), 1.95 (m, 1H), 1.84 (m, 1H):

MS (+ve ESI): 648.4 (M+H)⁺.

di(tert-butyl) {(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl phosphate, used as the starting material, was obtained as follows:

a) An analogous reaction to that described in example 2b, but starting with D-prolinol (101 mg, 1 mmol) yielded N-(3,5-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide (85 mg, 57% yield) as an off-white solid:

¹H-NMR (DMSO d₆, TFA): 8.96 (s, 1H), 8.30 (s, 1H), 7.35 (m, 2H), 7.33 (s, 1H), 6.91 (m, 1H), 6.84 (s, 1H), 4.31 (m, 2H), 4.01 (s, 3H), 3.86 (s, 2H), 3.78 (m, 1H), 3.63 (m, 4H), 3.22 (m, 2H), 2.30 (m, 2H), 2.13 (m, 1H), 2.03 (m, 1H), 1.80 (m, 1H), 1.78 (m, 1H):

MS (+ve ESI): 568.5 (M+H)⁺.

b) An analogous reaction to that described in example 3b, but starting with N-(3,5-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide (600 mg, 1.06 mmol) yielded di(tert-butyl) {(2R)-1-[3-({4-[(5-{2-[(3,5-difluorophenyl)amino]-2-oxoethyl}-1H-pyrazol-3-yl)amino]-6-methoxyquinazolin-7-yl}oxy)propyl]pyrrolidin-2-yl}methyl phosphate (361 mg, 45% yield) as an off-white solid:

¹H-NMR (DMSO d₆): 8.45 (s, 1H), 7.96 (s, 1H), 7.35 (m, 2H), 7.13 (s, 1H), 6.93 (m, 1H), 6.82 (s, 1H), 4.18 (m, 2H), 3.95 (s, 3H), 3.75 (m, 3H), 3.58 (m, 1H), 3.08 (m, 1H), 2.93 (m, 1H), 2.67 (m, 1H), 2.46 (m, 1H), 2.22 (q, 1H), 1.96 (m, 2H), 1.86 (m, 1H), 1.69 (m, 2H), 1.61 (m, 1H), 1.38 (s, 18H):

MS (+ve ESI): 760.5 (M+H)⁺.

EXAMPLE 5

Preparation of Compound 5 in Table 1—{(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate An analogous reaction to that described in example 1, but starting with di(tert-butyl) {(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl phosphate (282 mg, 0.38 mmol) yielded compound 5 in table 1 (265 mg, 97% yield) as an off-white solid:

¹H-NMR (DMSO d₆): 8.90 (s, 1H), 8.30 (s, 1H), 7.66 (d, 1H), 7.46 (s, 1H), 7.40 (m, 2H), 6.90 (m, 1H), 6.81 (s, 1H), 4.31 (m, 2H), 4.20 (m, 2H), 4.00 (s, 3H), 3.88 (s, 2H), 3.80 (m, 1H), 3.70 (m, 1H), 3.60 (m, 1H), 3.28 (m, 1H), 3.22 (m, 1H), 2.32 (m, 2H), 2.20 (m, 1H), 2.04 (m, 1H), 1.95 (m, 1H), 1.84 (m, 1H):

MS (+ve ESI): 630.6 (M+H)⁺.

di(tert-butyl) {(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl phosphate, used as the starting material, was obtained as follows:

a) An analogous reaction to that described in example 1j, but starting with L-prolinol (121 mg, 0.25 mmol) yielded N-(3-fluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide (86 mg, 62% yield) as an off-white solid:

¹H-NMR (DMSO d₆, TFA): 8.95 (s, 1H), 8.29 (s, 1H), 7.60-7.70 (m, 1H), 7.28-7.40 (m, 3H), 6.85-6.92 (m, 1H), 6.82 (s, 1H), 4.31 (m, 2H), 4.00 (s, 3H), 3.84 (s, 2H), 3.70-3.80 (m, 1H), 3.50-3.70 (m, 4H), 3.10-3.30 (m, 2H), 2.20-2.40 (m, 2H), 2.05-2.20 (m, 1H), 1.95-2.10 (m, 1H), 1.85-1.95 (m, 1H), 1.70-7.85 (m, 1H):

MS (+ve ESI): 549.6 (M+H)⁺.

b) An analogous reaction to that described in example 1k, but starting with N-(3-fluorophenyl)-2-{3-[(7-{3-[(2S)-2-(hydroxymethyl)pyrrolidin-1-yl]propoxy}-6-methoxyquinazolin-4-yl)amino]-1H-pyrazol-5-yl}acetamide (275 mg, 0.5 mmol) yielded di(tert-butyl) {(2S)-1-[3-({4-[(5-{2-[(3-fluorophenyl)amino]-2-oxoethyl}-1H-pyrazol-3-yl)amino]-6-methoxyquinazolin-7-yl}oxy)propyl]pyrrolidin-2-yl}methyl phosphate (255 mg, 69% yield) as an off-white solid:

¹H-NMR (DMSO d₆): 8.46 (s, 1H), 7.98 (s, 1H), 7.64 (d, 1H), 7.36 (m, 2H), 7.15 (s, 1H), 6.89 (m, 1H), 6.81 (s, 1H), 4.18 (m, 2H), 3.93 (s, 3H), 3.75 (m, 3H), 3.58 (m, 1H), 3.11 (m, 1H), 2.97 (m, 1H), 2.67 (n, 1H), 2.46 (m, 1H), 2.22 (m, 1H), 1.98 (m, 2H), 1.82 (m, 1H), 1.71 (m, 2H), 1.62 (m, 1H), 1.38 (s, 18H):

MS (+ve ESI): 742.7 (M+H)⁺.

EXAMPLE 6

Preparation of compound 6 in table 1—2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-6- methoxyquinazolin-7-yl}oxy)propyl](propyl)amino]ethyl phosphate (316 mg, 0.41 mmol) yielded compound 6 in table 1 (300 mg, 100% yield):

¹H-NMR (DMSO d₆, TFA): 8.96 (s, 1H), 8.31 (s, 1H), 7.75 (m, 1H), 7.36 (s, 1H), 7.20 (m, 2H), 6.84 (s, 1H), 4.31 (t, 2H), 4.24 (m, 2H), 4.01 (s, 3H), 3.94 (s, 2H), 3.50 (m, 2H), 3.38 (m, 2H), 3.19 (m, 2H), 2.32 (m, 2H), 1.74 (m, 2H), 0.95 (t, 3H):

MS (+ve ESI): 650.3 (M+H)⁺.

di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl phosphate used as starting material was obtained as follows:

a) 5-{[7-(3-chloropropoxy)-6-methoxyquinazolin-4-yl]amino}-1H-pyrazol-3-yl)acetic acid (3.91 g, 10 mmol) was suspended in pyridine (20 ml) in the presence of 2,3-difluoroaniline (1.55 g, 12 mmol) under argon at 0° C. Phosphorus oxychloride (1.53 g, 10 mmol) in ethyl acetate (2 ml) was slowly added at 0° C. and the resulting mixture was allowed to warm to ambient temperature over 1.5 hours. The reaction mixture was diluted with ethyl acetate (150 ml) and diethyl ether (50 ml) resulting in the precipitation of a red solid. The solid was recovered by suction filtration, dried and re-suspended in water (100 ml). The mixture was cooled to 0° C. and the pH adjusted to 7 by addition of 1.5 N aqueous ammonium hydroxide solution. After 15 minutes stirring, the solid was recovered, dried, and purified by chromatography on silica gel, eluting with dichloromethane:methanol (9515) and increased polarity to dichloromethane:methanolic ammonia (95:2) to yield 2-(3-{[7-(3-chloropropoxy)-6-methoxyquinazolin-4-yl]amino}-1H-pyrazol-5-yl)-N-(2,3-difluorophenyl)acetamide as a pink solid (2.55 g, 50% yield):

¹H-NMR (DMSO d₆, TFA): 8.94 (s, 1H), 8.28 (s, 1H), 7.73 (m, 1H), 7.33 (s, 1H), 7.15-7.22 (m, 1H), 6.84 (s, 1H), 4.30 (m, 2H), 4.00 (s, 3H), 3.94 (s, 2H), 3.84 (m, 2H), 2.30 (m, 2H):

MS (+ve ESI): 503.9 (M+H)⁺.

b) 2-(propylamino)ethanol (700 mg, 68 mmol) and potassium iodide (564 mg, 34 mmol) were added to a solution of 2-(3-{[7-(3-chloropropoxy)-6-methoxyquinazolin-4-yl]amino}-1H-pyrazol-5-yl)-N-(2,3-difluorophenyl)acetamide (855 mg, 17 mmol) in dimethylacetamide (8 ml) and the reaction heated at 85° C. for 5 hours. The solvent was evaporated in vacuo, the residue triturated with diethyl ether and the solid was collected by suction filtration. Purification by chromatography on silica gel, eluting with, dichloromethane/methanol (90:10) to dichloromethane/methanol/ammonia (7.0 N) to give N-(2,3-difluorophenyl)-2-{3-[(7-{3-[(2-hydroxyethyl)(propyl)amino]propoxy}-6-methoxyquinazolin-4-yl)amino]-1H-pyrazol-5-yl}acetamide (650 mg, 67% yield):

¹H-NMR (DMSO d₆, TFA): 8.96 (s, 1H), 8.30 (s, 1H), 7.75 (m, 1H), 7.33 (s, 1H), 7.18-7.22 (m, 2H), 6.84 (s, 1H), 4.30 (m, 2H), 4.00 (s, 3H), 3.94 (s, 2H), 3.78 (m, 2H), 3.30-3.45 (m, 2H), 3.28 (m, 2H), 3.15-3.20 (m, 2H), 2.28 (m, 2H), 1.73 (m, 2H), 0.95 (t, 3H):

MS (+ve ESI): 570.3 (M+H)⁺.

c) Di-tert-butyl-diethylphosphoramidite (417 μm, 1.5 mmol) was slowly added to a solution of N-(2,3-difluorophenyl)-2-{3-[(7-{3-[(2-hydroxyethyl)(propyl) amino]propoxy}-6-methoxyquinazolin-4-yl)amino]-1H-pyrazol-5-yl}acetamide (569 mg, 1 mmol) in dimethylformamide (2.5 ml) in the presence of tetrazole (210 mg, 3 mmol) at ambient temperature under argon. The mixture was stirred at ambient temperature for 1.5 hours, cooled to –10° C. and hydrogen peroxide (134 μm of a 9.0 N solution, 1.2 mmol) was slowly added. The resulting mixture was stirred at ambient temperature for 2 hours. Sodium metabisulphite (570 mg, 3 mmol) in water (2 ml) was then added at 0° C. and the mixture was stirred at ambient temperature for 0.5 hour. The mixture was concentrated, dichloromethane/methanol (8:2) was added before the solid was filtered and washed with dichloromethane/methanol. Concentration of the filtrate in vacuo followed by chromatography on silica gel, eluting with dichloromethane/methanol (90:10) to dichloromethane/methanol/ammonia (7.0 N) (90:10:1), yielded di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino] ethyl phosphate as an off-white solid (319 mg, 42% yield):

¹H-NMR (DMSO d₆, TFA): 8.95 (s, 1H), 8.29 (s, 1H), 7.72 (m, 1H), 7.33 (s, 1H), 7.18 (m, 2H), 6.84 (s, 1H), 4.20-4.35 (m, 4H), 4.00 (s, 3H), 3.94 (s, 2H), 3.53 (m, 2H), 3.39 (m, 2H), 3.20 (m, 2H), 2.30 (m, 2H), 1.73 (m, 2H), 1.44 (s, 18H), 0.95 (t, 3H):

MS (+ve ESI): 762.5 (M+H)⁺.

Compound 6, synthesised above as the dihydrochloride salt, could also be prepared as the free base according to the following method:

d) 2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl dihydrogen phosphate dihydrochloride (10 g, 13 mmol) was solubilized in methanol (300 ml) and cyclohexane oxide (12,7 g, 130 mmol) was added to the solution. The solution was stirred at ambient temperature for 48 hours, during which time a white solid precipitated. The mixture was diluted with diethyl ether (100 ml) and the solid was recovered by filtration, washed with ether and dried in vacuo to give 2-[[3-({4-[(5-{2-[(2,3-difluorophenyl)amino]-2-oxoethyl}-1H-pyrazol-3-yl)amino]-6-methoxyquinazolin-7-yl}oxy)propyl](propyl)amino]ethyl dihydrogen phosphate (7.65 g, 88% yield) as a light yellow powder:

¹H-NMR (DMSO d₆, TFA): 8.96 (s, 1H), 8.30 (s, 1H), 7.74 (m, 1H), 7.34 (s, 1H), 7.19 (m, 2H), 6.84 (s, 1H), 4.31 (m, 2H), 4.24 (m, 2H), 4.01 (s, 3H), 3.94 (s, 2H), 3.51 (m, 2H), 3.38 (m, 2H), 3.18 (m, 2H), 2.29 (m, 2H), 1.73 (m, 2H), 0.96 (t, 3H):

MS (+ve ESI): 650 (M+H)⁺.

$C_{28}H_{34}F_2N_7O_7P$+1.04$H_2O$ +0.03 $Et_2O$ requires C, 50.37%; H, 5.47%; N, 14.62%; Found C, 50.02%; H, 5.54%; N, 14.48%.

EXAMPLE 7

Preparation of compound 7 in table 1—2-[[3-({4-[(5-{2-[(2,3-difluorophenyl)amino]-2-oxoethyl}-1H-pyrazol-3-yl)amino]-6-methoxyquinazolin-7-yl}oxy) propyl](isobutyl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl phosphate (465 mg, 0.6 mmol) yielded compound 7 in table 1 (480 mg, 100% yield):

¹H-NMR (DMSO 44, TFA): 8.95 (s, 1H), 8.34 (s, 1H), 7.76 (m, 1H), 7.43 (s, 1H), 7.18 (m, 2H), 6.86 (s, 1H), 4.33 (m, 4H), 4.02 (s, 3H), 3.97 (s, 2H), 3.54 (m, 2H), 3.40 (m, 2H), 3.12 (d, 2H), 2.35 (m, 2H), 2.17 (m, 1H), 1.05 (d, 6H).

di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl phosphate used as starting material was obtained as follows:
a) A cooled (−60° C.) solution of ethylene oxide (5.28 g, 120 mmol) in methanol (14 ml), was added slowly to a solution of isobutylamine (30.7 g, 420 mmol) in methanol (100 ml) at −65° C. under argon. The mixture was allowed to warmn to ambient temperature over 14 hours, concentrated in vacuo and the residual oil was purified by distillation (b.p. 130° C./0.5 mmHg) to yield 2-(isobutylamino)ethanol (11 g, 78% yield):
$^1$H-NMR (DMSO d$_6$): 4.40 (m, 1H), 3.42 (m, 2H), 2.50 (m, 2H), 2.30 (d, 2H), 1.63 (m, 1H), 0.85 (d, 6H).
b) An analogous reaction to that described in example 6b, but starting with 2-(isobutylamino)ethanol (936 mg, 80 mmol) and heating at 90° C. for 3.5 hours, yielded N-(2,3-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide as an off-white solid (810 mg, 69% yield):
$^1$H-NMR (DMSO d$_6$, TFA): 8.96 (s, 1H), 8.30 (s, 1H), 7.45 (m, 1H), 7.34 (s, 1H), 7.21 (m, 2H), 6.84 (s, 1H), 4.31 (m, 2H), 4.00 (s, 3H), 3.95 (s, 2H), 3.81 (m, 2H), 3.36 (m, 2H), 3.30 (m, 2H), 3.12 (m, 1H), 3.06 (m, 1H), 2.31 (m, 2H), 2.13 (m, 1H), 1.01 (d, 6H):
MS (+ve ESI): 584.3 (M+H)$^+$.
c) An analogous reaction to that described to that described in example 6c, but starting with N-(2,3-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide (4.96 mg, 8.5 mmol) yielded di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](isobutyl)amino]ethyl phosphate (4.7 g, 71% yield):
$^1$H-NMR (DMSO d$_6$, TFA): 8.96 (s, 1H), 8.30 (s, 1H), 7.74 (m, 1H), 7.34 (s, 1H), 7.19 (m, 2H), 6.84 (s, 1H), 4.30 (m, 4H), 4.00 (s, 3H), 3.94 (s, 2H), 3.54 (m, 2H), 3.39 (m, 2H), 3.12 (d, 2H), 2.32 (m, 2H), 2.14 (m, 1H), 1.45 (s, 18H), 1.02 (d, 6H)
MS (+ve ESI): 776.8 (M+H)$^+$.

EXAMPLE 8

Preparation of compound 8 in table 1—2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl dihydrogen phosphate An analogous reaction to that described in example 1, but starting with di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl phosphate (325 mg, 0.42 mmol) yielded compound 8 in table 1 (315 mg, 98% yield):
$^1$H-NMR (DMSO d$_6$, TFA): 8.95 (s, 1H), 8.32 (s, 1H), 7.39 (d, 1H), 7.38 (s, 1H), 7.36 (d, 1H), 6.91 (t, 1H), 6.84 (s, 1H), 4.30 (m, 2H), 4.01 (s, 3H), 3.87 (s, 2H), 3.53 (m, 2H), 3.39 (m, 2H), 3.11 (d, 1H), 2.32 (m, 2H), 2.14 (m, 1H), 1.02 (d, 6H):
MS (+ve ESI): 664.3 (M+H)$^+$.

di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl phosphate used as starting material was obtained as follows:
a) 2-(3-{[7-(3-chloropropoxy)-6-methoxyquinazolin-4-yl]amino}-1H-pyrazol-5-yl)-N-(3,5-difluorophenyl)acetamide (2.0 g, 4.0 mmol) in 1-methyl-2-pyrrolidinone (20 ml), potassium iodide (1.33 g, 8.0 mmol) was reacted with 2-(isobutylamino)ethanol (1.88 g, 16 mmol) under argon, at 60° C. for 8 hours. The solvent was evaporated in vacuo, and the residue was purified by chromatography on silica gel, eluting with dichloromethane/methanol (95:5) to dichloromethane/methanol/ammonia (7.0 N) (95:5:1) to yield N-(3,5-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide (1.05 g, 45% yield):
$^1$H-NMR (DMSO d$_6$, TFA): 8.95 (s, 1H), 8.29 (s, 1H), 7.35 (d, 2H), 7.34 (s, 1H), 6.92 (t, 1H), 6.83 (s, 1H), 4.30 (m, 2H), 4.00 (s, 3H), 3.86 (s, 2H), 3.82 (t, 2H), 3.89 (m, 2H), 3.29 (m, 2H), 2.17-2.98 (m, 2H), 2.30 (m, 2H), 2.13 (m, 1H), 1.01 (d, 6H):
MS (+ve ESI): 584.3 (M+H)$^+$.
b) Di-tert-butyl-diethylphosphoramidite (1.25 ml, 4.18 mmol) was slowly added to a solution of N-(3,5-difluorophenyl)-2-{3-[(7-{3-[(2-hydroxyethyl)(isobutyl)amino]propoxy}-6-methoxyquinazolin-4-yl)amino]-1H-pyrazol-5-yl}acetamide (1.03 g, 1.73 mmol) in dimethylformamide (6 ml) in the presence of tetrazole (431 mg, 6.16 mmol). The mixture was stirred at ambient temperature for 2 hours before dichloromethane (30 ml) was added. The resulting mixture was washed with a saturated solution of sodium bicarbonate (15 ml), the aqueous phase was extracted with dichloromethane (3×25 ml), dried and concentrated in vacuo. The crude product was dissolved in tetrahydrofuran (25 ml), cooled to 0° C. and hydrogen peroxide (30% w/w, 0.40 ml, 3.9 mmol) was slowly added to the solution. The reaction was stirred for 2 hours at ambient temperature, cooled to 0° C., and treated with a solution of sodium metabisulphite (1.08 g, 5.7 mmol) in water (2 ml). The mixture was stirred for 0.5 hour at ambient temperature, diluted with ethyl acetate (30 ml), washed with aqueous sodium bicarbonate solution (15 ml) and extracted twice with ethyl acetate (20 ml) Solvent evaporation in vacuo followed by purification by chromatography on silica gel, eluting with dichloromethane/methanol (98:2) to dichloromethane/methanol/ammonia (7.0 N) (95:5:1) yielded di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](isobutyl)amino]ethyl phosphate (335 mg, 25% yield):
$^1$H-NMR (DMSO d$_6$, TFA): 12.35 (s, 1H), 10.64 (s, 1H), 10.16 (s, 1H), 8.45 (s, 1H), 7.99 (s, 1H), 7.36 (d, 2H), 7.13 (s, 1H), 6.94 (t, 1H), 6.84 (s, 1H), 4.19 (t, 2H), 3.95 (s, 3H), 3.87 (q, 2H), 3.79 (s, 2H), 2.65 (m, 4H), 2.21 (d, 2H), 1.91 (m, 2H), 1.70 (m, 1H), 1.39 (s, 18H), 0.83 (d, 6H):
MS (+ve ESI): 776.4 (M+H)$^+$.

EXAMPLE 9

Preparation of compound 9 in table 1—2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl dihydrogen phosphate An analogous reaction to that described in example 1 but starting with di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl phosphate (510 mg, 0.67 mmol) yielded compound 9 in table 1 (503 mg, 42% yield):
$^1$H-NMR (DMSO (16, TFA): 8.94 (s, 1H), 8.31 (s, 1H), 7.38 (d, 1H), 7.37 (s, 2H), 7.36 (d, 1H), 6.92 (t, 1H), 6.83 (s, 1H), 4.30 (t, 2H), 4.24 (t, 2H), 4.00 (s, 3H), 3.87 (s, 2H), 3.49 (t, 2H), 3.36 (t, 2H), 3.18 (t, 2H), 2.26-2.36 (m, 2H), 1.68-1.79 (m, 2H), 0.94 (t, 3H):

MS (+ve ESI): 649.9 (M+H)+.

di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl phosphate used as starting material was obtained as follows:

a) An analogous reaction to that described in example 8a, but starting with 2-(propylamino)ethanol (1.83 ml, 16 mmol) yielded N-(3,5-difluorophenyl)-2-{3-[(7-{3-[(2-hydroxyethyl)(propyl)amino]propoxy}-6-methoxyquinazolin-4-yl)amino]-1H-pyrazol-5-yl}acetamide (900 mg, 39% yield):

1H-NMR (DMSO d6): 10.63 (s, 1H), 10.17 (s, 1H), 8.46 (s, 1H), 8.00 (s, 1H), 7.36 (d, 2H), 7.14 (s, 1H), 6.94 (t, 1H), 6.85 (s, 1H), 4.35 (br s, 1H), 4.20 (t, 2H), 3.95 (s, 3H), 3.79 (s, 2H), 3.46 (m, 2H), 2.63 (m, 2H), 2.52 (m, 2H), 2.42 (m, 2H), 1.92 (m, 2H), 1.42 (m, 2H), 0.83 (t, 3H):

MS (+ve ESI): 570.3 (M+H)+.

b) An analogous reaction to that described in example 8b, but starting with N-(3,5-difluorophenyl)-2-{3-[(7-{3-[(2-hydroxyethyl)(propyl)amino]propoxy}-6-methoxyquinazolin-4-yl)amino]-1H-pyrazol-5-yl}acetamide (880 mg, 1.54 mmol) yielded di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](propyl)amino]ethyl phosphate (525 mg, 45% yield):

1H-NMR (DMSO d6, TFA): 12.35 (s, 1H), 10.63 (s, 1H), 10.16 (s, 1H), 8.45 (s, 1H), 7.99 (s, 1H), 7.37 (d, 1H), 7.34 (d, 1H), 7.13 (s, 1H), 6.94 (t, 1H), 6.84 (s, 1H), 4.17 (t, 2H), 3.94 (s, 3H), 3.87 (q, 2H), 3.79 (s, 2H), 2.67 (t, 2H), 2.63 (t, 2H), 2.43 (t, 2H), 1.91 (t, 2H), 1.39 (s, 18H), 0.83 (t, 3H):

MS (+ve ESI): 762.6 (M+H)+.

EXAMPLE 10

Preparation of compound 10 in table 1—2-[[3-({4[(5-{2-[(3-fluorophenyl)amino]-2-oxoethyl}-1H-pyrazol-3-yl)amino]-6-methoxyquinazolin-7-yl}oxy)propyl](isobutyl)amino]ethyl dihydrogen phosphate An analogous reaction to that described in example 1, but starting with di-tert-butyl 2-[[3-({4-[(5-{2-[(3-fluorophenyl)amino]-2-oxoethyl}-1H-pyrazol-3-yl)amino]-6-methoxyquinazolin-7-yl}oxy)propyl](isobutyl)amino]ethyl phosphate (450 mg, 0.59 mmol) yielded compound 10 in table 1 (420 mg, 99% yield):

1H-NMR (DMSO d6, TFA): 8.90 (s, 1H), 8.30 (s, 1H), 7.64 (m, 1H), 7.36 (m, 3H), 6.85 (m, 2H), 4.30 (m, 4H), 4.00 (s, 3H), 3.86 (s, 2H), 3.53 (m, 2H), 3.37 (m, 2H), 3.09 (m, 2H), 2.34 (m, 2H), 2.14 (m, 1H), 1.05 (m, 6H):

MS (+ve ESI): 646.6 (M+H)+.

di-tert-butyl 2-[[3-({4-[(5-{2-[(3-fluorophenyl)amino]-2-oxoethyl}-1H-pyrazol-3-yl)amino]-6-methoxyquinazolin-7-yl}oxy)propyl](isobutyl)amino]ethyl phosphate used as starting material was obtained as follows:

a) An analogous reaction to that described in example 5a, but starting with 2-(isobutyl amino)ethanol (181 mg, 1.55 mmol) yielded N-(3-fluorophenyl)-2-{3-[(7-{3-[(2-hydroxyethyl)(isobutyl)amino]propoxy}-6-methoxyquinazolin-4-yl)amino]-1H-pyrazol-5-yl}acetamide (101 mg, 57% yield):

1H-NMR (DMSO d6, TFA): 8.96 (s, 1H), 8.30 (s, 1H), 7.63 (d, 1H), 7.32-7.41 (m, 2H), 7.34 (s, 1H), 6.90 (t, 1H), 6.83 (s, 1H), 4.30 (t, 2H), 4.00 (s, 3H), 3.84 (s, 2H), 3.80 (t, 2H), 3.37 (t, 2H), 3.28 (t, 2H), 3.15-3.00 (m, 2H), 2.29 (m, 2H), 2.12 (m, 2H), 1.00 (d, 6H):

MS (+ve ESI): 566.3 (M+H)+.

b) An analogous reaction to that described in example 5b, but starting with N-(3-fluorophenyl)-2-{3-[(7-{3-[(2-hydroxyethyl)(isobutyl)amino]propoxy}-6-methoxyquinazolin-4-yl)amino]-1H-pyrazol-5-yl}acetamide (565 mg, 1 mmol) yielded di-tert-butyl 2-[[3-({4-[(5-{2-[(3-fluorophenyl)amino]-2-oxoethyl}-1H-pyrazol-3-yl)amino]-6-methoxyquinazolin-7-yl}oxy)propyl](isobutyl)amino]ethyl phosphate (420 mg, 55% yield):

1H-NMR (DMSO d6, TFA): 8.37 (s, 1H), 7.88 (s, 1H), 7.55 (m, 1H), 7.26 (m, 2H), 7.04 (s, 1H), 6.81 (m, 2H), 4.09 (t, 2H), 3.82 (s, 3H), 3.76 (m, 2H), 3.67 (m, 2H), 2.57 (m, 4H), 2.11 (m, 2H), 1.82 (m, 2H), 1.60 (m, 1H), 1.29 (s, 18H), 0.74 (d, 6H):

MS (+ve ESI): 758.5 (M+H)+.

EXAMPLE 11

Preparation of compound 11 in table 1—2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (350 mg, 0.45 mmol) yielded compound 11 in table 1 (325 mg, 100% yield):

1H-NMR (DMSO d6, TFA): 8.94 (s, 1H), 8.3 (s, 1H), 7.63 (d, 1H), 7.36 (s, 1H), 7.34 (m, 2H), 6.88 (m, 1H), 6.82 (s, 1H), 4.30 (m, 4H), 3.99 (s, 3H), 3.84 (s, 2H), 3.54 (m, 2H), 3.38 (m, 2H), 3.19 (m, 2H), 2.37 (m, 2H), 1.09 (s, 9H):

MS (+ve ESI): 660.4 (M+H)+.

di-tert-butyl 2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) Ethylene oxide (2.5 ml, 5.0 mmol) cooled to −20° C. was slowly added to a solution of (2,2-dimethylpropyl)amine (13 g, 150 mmol) in methanol (15 ml) at −30° C. under argon. The mixture was stirred at ambient temperature for 16 hours. The solvent was evaporated in vacuo, and the residue was purified by distillation (b.p. 132° C./9 mmHg) to yield 2-((2,2-dimethylpropyl)amino)ethanol (6.4 g, 97% yield):

1H-NMR (DMSO d6, TFA): 3.70 (m, 2H), 3.02 (m, 2H), 2.81 (m, 2H), 0.98 (s, 9H).

b) An analogous reaction to that described in example 5a, but starting with 2-(2,2-dimethylpropyl)amino)ethanol (203 mg, 1.55 mmol) yielded 2-{3-[(7-{3-[(2,2-dimethylpropyl)(2-hydroxyethyl)amino]propoxy}-6-methoxyquinazolin-4-yl)amino]-1H-pyrazol-5-yl}-N-(3-fluorophenyl)acetamide (111 mg, 61% yield):

1H-NMR (DMSO d6, TFA): 8.96 (s, 1H), 8.30 (s, 1H), 7.64 (d, 1H), 7.32-7.41 (m, 2H), 7.34 (s, 1H), 6.90 (t, 1H), 6.83 (s, 1H), 4.31 (t, 2H), 3.99 (s, 3H), 3.84 (s, 2H), 3.83 (t, 2H), 3.42 (t, 2H), 3.32 (t, 2H), 3.20 (dd, 2H), 2.35 (m, 2H), 1.07 (s, 9H):

MS (+ve ESI): 580.3 (M+H)+.

c) An analogous reaction to that described in example 5b, but starting with 2-{3-[(7-{3-[(2,2-dimethylpropyl)(2-hydroxyethyl)amino]propoxy}-6-methoxyquinazolin-4-yl)amino]-1H-pyrazol-5-yl}-N-(3-fluorophenyl)acetamide (1.33 g, 2.3 mmol) yielded di-tert-butyl 2-{(2,2-dimethylpropyl)[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (620 mg, 40% yield):

¹H-NMR (DMSO d₆, TFA): 8.95 (s, 1H), 8.3 (s, 1H), 7.64 (d, 1H), 7.28-7.40 (m, 2H), 7.34 (s, 1H), 6.88 (m, 1H), 6.84 (s, 1H), 4.31 (m, 4H), 4.00 (s, 3H), 3.85 (s, 2H), 3.56 (m, 2H), 3.39 (m, 2H), 3.21 (m, 2H), 2.32 (m, 2H), 1.43 (s, 9H), 1.10 (s, 9H):

MS (+ve ESI): 716.4 (M+H)⁺.

EXAMPLE 12

Preparation of compound 12 in table 1—1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl dihydrogen phosphate An analogous reaction to that described in example 1, but starting with di-tert-butyl 1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl phosphate (540 mg, 0.72 mmol) yielded compound 12 in table 1 (500 mg, 98% yield):

¹H-NMR (DMSO d₆, TFA): 8.92 (s, 1H), 8.28 (s, 1H), 7.62 (d, 1H), 7.32 (m, 3H), 6.82 (m, 2H), 4.45-4.66 (m, 2H), 4.27 (m, 2H), 3.99 (s, 3H), 3.84 (s, 2H), 3.55 (m, 2H), 3.30 (m, 2H), 3.00 (m, 2H), 2.30 (m, 2H), 2.05 (m, 2H), 1.65 (m, 2H):

MS (+ve ESI): 630.2 (M+H)⁺.

di-tert-butyl 1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl phosphate used starting material was obtained as follows:

a) An analogous reaction to that described in example 5a, but starting with piperidin-3-ol (101 mg, 1 mmol) yielded N-(3-fluorophenyl)-2-[3-({7-[3-(3-hydroxypiperidin-1-yl)propoxy]-6-methoxyquinazolin-4-yl}amino)-1H-pyrazol-5-yl]acetamide (65 mg, 47% yield):

¹H-NMR (DMSO d₆, TFA): 8.96 (s, 1H), 8.29 (s, 1H), 7.62 (d, 1H), 7.38 (m, 2H), 7.34 (m, 2H), 7.34 (s, 1H), 6.90 (m, 1H), 6.84 (s, 1H), 4.28 (m, 2H), 4.10 (m, 1H), 4.00 (s, 3H), 3.85 (s, 2H), 2.80-3.50 (m, 6H), 1.30-2.40 (m, 6H):

MS (+ve ESI): 550.6 (M+H)⁺.

b) An analogous reaction to that described in example 5b, but starting with N-(3-fluorophenyl)-2-[3-({7-[3-(3-hydroxypiperidin-1-yl)propoxy]-6-methoxyquinazolin-4-yl}amino)-1H-pyrazol-5-yl]acetamide (604 mg, 1.11 mmol) yielded di-tert-butyl 1-[3-({4-[(5-{2-[(3-fluorophenyl)amino]-2-oxoethyl}-1H-pyrazol-3-yl)amino]-6-methoxyquinazolin-7-yl}oxy)propyl]piperidin-3-yl phosphate (550 mg, 67% yield):

¹H-NMR (DMSO d₆, TFA): 8.38 (s, 1H), 7.90 (s, 1H), 7.55 (d, 1H), 7.30 (m, 2H), 7.06 (s, 1H), 6.80 (m, 2H), 4.09 (m, 3H), 3.86 (s, 3H), 3.68 (s, 2H), 2.80 (m, 1H), 2.55 (m, 1H), 2.03 (m, 2H), 1.87 (m, 3H), 1.60 (m, 1H), 1.35 (m, 22H):

MS (+ve ESI): 742.5 (M+H)⁺.

EXAMPLE 13

Preparation of compound 13 in table 1—{(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl dihydrogen phosphate An analogous reaction to that described in example 1, but starting with di-tert-butyl {(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl phosphate (445 mg, 0.59 mmol) yielded compound 13 in table 1 (440 mg, 94% yield):

¹H-NMR (DMSO d₆, TFA): 8.94 (s, 1H), 8.31 (s, 1H), 7.73 (m, 1H), 7.40 (s, 1H), 7.19 (m, 2H), 6.83 (s, 1H), 4.31 (t, 2H), 4.20 (m, 2H), 4.01 (s, 3H), 3.94 (s, 2H), 3.82 (m, 1H), 3.70 (m, 1H), 3.60 (m, 1H), 3.31 (m, 1H), 3.23 (m, 1H), 2.32 (m, 2H), 2.19 (m, 1H), 2.04 (m, 1H), 1.95 (m, 1H), 1.85 (m, 1H):

MS (+ve ESI): 648.3 (M+H)⁺.

di-tert-butyl {(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl phosphate used as starting material was obtained as follows:

a) An analogous reaction to that described in example 6b, but starting with (2R)-pyrrolidin-2-ylmethanol (101 mg, 1 mmol) yielded N-(2,3-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide (134 mg, 79% yield):

¹H-NMR (DMSO d₆, TFA): 8.95 (s, 1H), 8.29 (s, 1H), 7.75 (m, 1H), 7.32 (s, 1H), 7.16 (m, 2H), 6.84 (s, 1H), 4.30 (m, 2H), 4.00 (s, 3H), 3.94 (s, 2H), 3.70-3.85 (m, 1H), 3.52-3.70 (m, 4H), 3.15-3.30 (m, 2H), 2.25-2.35 (m, 2H), 1.75-2.20 (m, 4H):

MS ES⁺: 568.2 (M+H)⁺

MS (+ve ESI): 568.2 (M+H)⁺.

b) An analogous reaction to that described in example 6c, but starting with N-(2,3-difluorophenyl)-2-{3-[(7-{3-[(2R)-2-(hydroxymethyl)pyrrolidin-1-yl]propoxy}-6-methoxyquinazolin-4-yl)amino]-1H-pyrazol-5-yl}acetamide (1.1 g, 1.9 mmol) yielded di-tert-butyl {(2R)-1-[3-({4-[(5-{2-[(2,3-difluorophenyl)amino]-2-oxoethyl}-1H-pyrazol-3-yl)amino]-6-methoxyquinazolin-7-yl}oxy)propyl]pyrrolidin-2-yl}methyl phosphate (453 mg, 31% yield):

¹H-NMR (DMSO d₆, TFA): 10.24 (s, 1H), 10.15 (s, 1H), 8.44 (s, 1H), 7.98 (s, 1H), 7.72 (t, 1H), 7.19 (m, 2H), 7.13 (s, 1H), 6.83 (s, 1H), 4.17 (br s, 2H), 3.93 (s, 3H), 3.85 (s, 1H), 3.77 (m, 1H), 3.56 (t, 1H), 3.54 (t, 1H), 3.08 (t, 1H), 2.94 (m, 1H), 2.66 (m, 1H), 2.47 (m, 1H), 2.20 (q, 1H), 1.94 (m, 2H), 1.86 (m, 1H), 1.69 (m, 2H), 1.60 (m, 1H), 1.37 (s, 9H), 1.36 (s, 9H):

MS (+ve ESI): 758.5 (M+H)⁺.

Compound 13, synthesised above as the dihydrochloride salt, could also be prepared as the free base according to the following method:

c) An analogous reaction to that described in example 6d, but starting with Compound 13 yielded the free base of Compound 13 as a pale yellow solid:

¹H-NMR (DMSO d₆): 10.30 (s, 1H), 10.20 (s, 1H), 8.50 (s, 1H), 8.00 (s, 1H), 7.70-7.80 (m, 1H), 7.20-7.30 (m, 3H), 6.70 (s, 1H), 4.30-4.40 (m, 2H), 4.10-4.20 (m, 1H), 3.90 (s, 3H), 3.80 (s, 2H), 3.70-3.75 (m, 1H), 3.40-3.50 (m, 1H), 3.30-3.35 (m, 1H), 3.20-3.25 (m, 1H), 3.05-3.15 (m, 1H), 2.90-3.00 (m, 1H), 2.10-2.20 (m, 2H), 1.90-2.00 (m, 1H), 1.70-1.80 (m, 3H):

MS (+ve ESI): 648 (M+H)⁺.

$C_{28}H_{32}F_2N_7O_7P+2.3H_2O$ requires C, 48.8%; H, 5.35%; N, 14.23%; Found C, 48.95%; H, 5.03%; N, 14.15%

EXAMPLE 14

Preparation of compound 14 in table 1—2-[[3-({4-[(5-}2-[(3,5-difluorophenyl)amino]-2-oxoethyl}-1H-pyrazol-3-yl)amino]-6-methoxyquinazolin-7-yl]oxy)propyl](prop-2-yn-1-yl)amino]ethyl dihydrogen phosphate An analogous reaction to that described in example 1, but starting with di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](prop-2-yn-1-yl)amino]ethyl phosphate (400 mg, 0.53 mmol) yielded compound 14 in table 1 (290 mg, 77% yield):

$^1$H-NMR (DMSO d$_6$, TFA): 8.94 (s, 1H), 8.34 (s, 1H), 7.42 (m, 3H), 6.89 (m, 2H), 4.37 (m, 6H), 4.04 (s, 3H), 3.92 (s, 2H), 3.87 (s, 1H), 3.57 (m, 2H), 3.47 (m, 2H), 2.39 (m, 2H):

MS (+ve ESI): 646.4 (M+H)$^+$.

di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](prop-2-yn-1-yl)amino]ethyl phosphate used as starting material was obtained as follows:

a) A cooled (−40° C.) solution of ethylene oxide (3.3 g, 75 mmol) in methanol (10 ml) was slowly added to a solution of propargylamine (16.5 g, 300 mmol) in methanol (60 ml) cooled to −65° C. under argon. The mixture was allowed to warm to ambient temperature over 16 hours, the solvent was evaporated in vacuo, and the residue was purified by distillation to yield 2-(prop-2-yn-1-ylamino)ethanol (5.0 g, 67% yield):

$^1$H-NMR (DMSO d$_6$, TFA): 3.91 (m, 2H), 3.65 (m, 3H), 3.06 (m, 2H).

b) An analogous reaction to that described in example 8a, but starting with 2-(prop-2-yn-1-ylamino)ethanol (99 mg, 1 mmol) and heating at 105° C. for 12 hours yielded N-(3,5-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide (50 mg, 31% yield):

$^1$H-NMR (DMSO d$_6$, TFA): 8.95 (s, 1H), 8.29 (s, 1H), 7.34 (m, 2H), 7.31 (s, 1H), 6.91 (m, 1H), 6.83 (s, 1H), 4.29 (m, 4H), 4.00 (s, 3H), 3.89 (m, 1H), 3.86 (s, 2H), 3.80 (m, 2H), 3.43 (m, 2H), 3.36 (m, 2H), 2.30 (m, 2H):

MS (+ve ESI): 566.2 (M+H)$^+$.

c) An analogous reaction to that described in example 8b, but starting with N-(3,5-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide (734 mg, 1.3 mmol) yielded di-tert-butyl 2-[[3-({4-[(5-{2-[(3,5-difluorophenyl)amino]-2-oxoethyl}-1H-pyrazol-3-yl)amino]-6-methoxyquinazolin-7-yl}oxy)propyl](prop-2-yn-1-yl)amino]ethyl phosphate (400 mg, 41% yield):

$^1$H-NMR (DMSO d$_6$, TFA): 8.51 (s, 1H), 7.99 (s, 1H), 7.35 (m, 2H), 7.28 (s, 1H), 6.93 (m, 1H), 6.72 (s, 1H), 4.21 (m, 2H), 3.95 (m, 5H), 3.75 (m, 2H), 3.60 (m, 2H), 3.28 (s, 1H), 2.85 (m, 2H), 2.79 (m, 2H), 1.97 (m, 2H), 1.37 (s, 9H).

EXAMPLE 15

Preparation of compound 15 in table 1—2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl phosphate (450 mg, 0.59 mmol) yielded compound 15 in table 1 (405 mg, 95% yield):

$^1$H-NMR (DMSO d$_6$): 8.90 (s, 1H), 8.32 (s, 1H), 7.69 (m, 1H), 7.51 (s, 1H), 7.21 (m, 2H), 6.81 (s, 1H), 4.33 (m, 2H), 4.26 (m, 2H), 4.00 (s, 3H), 3.92 (s, 2H), 3.72 (m, 1H), 3.40 (m, 2H), 3.29 (m, 2H), 2.32 (m, 2H), 1.31 (m, 6H):

MS (+ve ESI): 650.3 (M+H)$^+$.

di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl phosphate used as starting material was obtained as follows:

a) An analogous reaction to that described in example 6b, but starting with 2-(isopropylamino)ethanol (103 mg, 1 mmol) yielded N-(2,3-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide (84 mg, 49% yield):

$^1$H-NMR (DMSO d$_6$, TFA): 8.97 (s, 1H), 8.33 (s, 1H), 7.79 (m, 1H), 7.35 (s, 1H), 7.18 (m, 2H), 6.88 (s, 1H), 4.34 (t, 2H), 4.03 (s, 3H), 3.98 (s, 2H), 3.81 (m, 3H), 3.40 (m, 3H), 3.20 (m, 1H), 2.35 (m, 2H), 1.33 (m, 6H):

MS (+ve ESI): 570.2 (M+H)$^+$.

b) An analogous reaction to that described in example 6c, but starting with N-(2,3-difluorophenyl)-2-{3-[(7-{3-[(2-hydroxyethyl)(isopropyl)amino]propoxy}-6-methoxyquinazolin-4-yl)amino]-1H-pyrazol-5-yl}acetamide (650 mg, 1.14 mmol) yielded di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](isopropyl)amino]ethyl phosphate (520 mg, 60% yield):

$^1$H-NMR (DMSO d$_6$): 8.44 (s, 1H), 7.98 (s, 1H), 7.73 (m, 1H), 7.19 (m, 2H), 7.12 (s, 1H), 6.83 (s, 1H), 4.16 (t, 2H), 3.93 (s, 3H), 3.85 (s, 2H), 3.77 (m, 2H), 2.90 (m, 1H), 2.60 (m, 4H), 1.86 (m, 2H), 1.36 (s, 18H), 0.94 (m, 6H):

MS (+ve ESI): 762.7 (M+H)$^+$. EXAMPLE 16

Preparation of compound 16 in table 1—2-[[3-({4-[(5-{2-[(2,3-difluorophenyl)amino]-2-oxoethyl-1H-pyrazol-3-yl)amino]-6-methoxyquinazolin-7-yl}oxy)propyl](prop-2-yn-1-yl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl phosphate (630 mg, 0.84 mmol) yielded compound 16 in table 1 ((540 mg, 86% yield):

$^1$H-NMR (DMSO d$_6$, AcOD): 8.89 (s, 1H), 8.29 (m, 1H), 7.70 (m, 1H), 7.37 (m, 1H), 7.16 (m, 2H), 6.81 (m, 1H), 4.29 (m, 6H), 3.99 (m, 3H), 3.92 (m, 2H), 3.82 (m, 1H), 3.52 (m, 2H), 3.43 (m, 2H), 2.32 (m, 2H):

MS (+ve ESI): 646.3 (M+H)$^+$.

di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl phosphate used as starting material was obtained as follows:

a) An analogous reaction to that described in example 6b, but starting with 2-(prop-2-yn-1-ylamino)ethanol (99 mg, 1 mmol) yielded N-(2,3-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide (128 mg, 75% yield):

$^1$H-NMR (DMSO d$_6$, TFA): 8.95 (s, 1H), 8.29 (s, 1H), 7.74 (m, 1H), 7.31 (s, 1H), 7.18 (m, 2H), 6.83 (s, 1H), 4.30 (m, 4H), 4.00 (s, 3H), 3.94 (s, 2H), 3.87 (m, 1H), 3.80 (m, 2H), 3.44 (m, 2H), 3.35 (m, 2H), 2.30 (m, 2H):

MS (+ve ESI): 566.2 (M+H)+.

b) An analogous reaction to that described in example 6c, but starting with N-(2,3-difluorophenyl)-2-{3-[(7-{3-[(2-hydroxyethyl)(prop-2-yn-1-yl)amino]propoxy}-6-methoxyquinazolin-4-yl)amino]-1H-pyrazol-5-yl}acetamide (680 mg, 1.2 mmol) yielded di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](prop-2-yn-1-yl)amino]ethyl phosphate (630 mg, 70% yield):

$^1$H-NMR (DMSO d$_6$): 8.45 (s, 1H), 7.98 (s, 1H), 7.72 (m, 1H), 7.17 (m, 3H), 6.83 (s, 1H), 4.16 (m, 2H), 3.85 (m, 7H), 3.45 (m, 2H), 3.13 (m, 1H), 2.69 (m, 4H), 1.90 (m, 2H), 1.35 (m, 18H):

MS (+ve ESI): 758.5 (M+H)+.

EXAMPLE 17

Preparation of compound 17 in table 1—2-[[3-({4-[(5-{2-[(2,3-difluorophenyl)amino]-2-oxoethyl}-1H-Pyrazol-3-yl)amino]-6-methoxyquinazolin-7-yl]oxy)propyl](2-methoxyethyl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](2-methoxyethyl)amino]ethyl phosphate (500 mg, 0.64 mmol) yielded compound 17 in table 1 (450 mg, 94% yield):

$^1$H-NMR (DMSO d$_6$, AcOD): 8.91 (s, 1H), 8.33 (s, 1H), 7.74 (m, 1H), 7.43 (s, 1H), 7.18 (m, 2H), 6.85 (s, 1H), 4.32 (m, 4H), 4.02 (s, 3H), 3.96 (s, 2H), 3.77 (m, 2H), 3.56 (m, 2H), 3.49 (m, 2H), 3.44 (m, 2H), 3.34 (s, 3H), 2.34 (m, 2H):

MS (+ve ESI): 666.2 (M+H)+.

di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](2-methoxyethyl)amino]ethyl phosphate used as starting material was obtained as follows:

a) An analogous reaction to that described in example 6b, but starting with 2-((2-methoxyethyl)amino)ethanol (119 mg, 1 mmol—prepared according to A. A. Santilli et al, *J. Heterocycl. Chem.* 1972, 9, 309-13) yielded N-(2,3-difluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide (124 mg, 71% yield):

$^1$H-NMR (DMSO d$_6$, TFA): 8.97 (s, 1H), 8.31 (s, 1H), 7.76 (m, 1H), 7.33 (s, 1H), 7.19 (m, 2H), 6.85 (s, 1H), 4.31 (t, 2H), 4.02 (s, 3H), 3.95 (s, 2H), 3.80 (t, 2H), 3.73 (t, 2H), 3.45 (m, 4H), 3.36 (m, 5H), 2.31 (m, 2H):

MS (+ve ESI): 586.2 (M+H)+.

b) An analogous reaction to that described in example 6c, but starting with N-(2,3-difluorophenyl)-2-{3-[(7-{3-[(2-hydroxyethyl)(2-methoxyethyl)amino]propoxy}-6-methoxyquinazolin-4-yl)amino]-1H-pyrazol-5-yl}acetamide (800 mg, 1.4 mmol) yielded di-tert-butyl 2-[[3-({4-[(5-{2-[(2,3-difluorophenyl)amino]-2-oxoethyl}-1H-pyrazol-3-yl)amino]-6-methoxyquinazolin-7-yl}oxy)propyl](2-methoxyethyl)amino]ethyl phosphate (560 mg, 53% yield):

$^1$H-NMR (DMSO d$_6$): 8.44 (s, 1H), 7.99 (s, 1H), 7.72 (m, 1H), 7.20 (m, 2H), 7.12 (s, 1H), 6.84 (s, 1H), 4.16 (t, 2H), 3.93 (t, 3H), 3.85 (m, 4H), 3.38 (m, 2H), 3.20 (s, 3H), 2.74 (m, 2H), 2.67 (m, 4H), 1.90 (m, 2H), 1.39 (m, 18H):

MS (+ve ESI): 778.6 (M+H)+.

EXAMPLE 18

Preparation of compound 18 in table 1—2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (729 mg, 1.04 mmol) yielded compound 18 in table 1 (505 mg, 72% yield):

$^1$H-NMR (DMSO d$_6$, AcOD): 8.85 (s, 1H), 8.25 (s, 1H), 7.60 (d, 1H), 7.33 (m, 3H), 6.83 (m, 1H), 6.80 (s, 1H), 4.27 (m, 2H), 4.15 (m, 2H), 3.97 (s, 3H), 3.83 (s, 2H), 3.26 (m, 2H), 3.15 (m, 2H), 2.24 (m, 2H):

MS (+ve ESI): 590.1 (M+H)+.

di-tert-butyl 2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) An analogous reaction to that described in example 5a, but starting with 2-(cyclopropylamino)ethanol (156 mg, 1.55 mmol) yielded 2-{3-[(7-{3-[cyclopropyl(2-hydroxyethyl)amino]propoxy}-6-methoxyquinazolin-4-yl)amino]-1H-pyrazol-5-yl}-N-(3-fluorophenyl)acetamide (22 mg, 13% yield):

$^1$H-NMR (DMSO d$_6$, TFA): 8.97 (s, 1H), 8.31 (s, 1H), 7.65 (d, 1H), 7.33-7.42 (m, 2H), 7.37 (s, 1H), 6.92 (t, 1H), 6.85 (s, 1H), 4.33 (m, 2H), 4.02 (s, 3H), 3.86 (s, 2H), 3.79 (t, 2H), 3.48 (m, 2H), 3.42 (t, 2H), 2.97 (m, 1H), 2.36 (m, 2H), 1.04 (m, 2H), 0.94 (m, 2H): MS (+ve ESI): 550.2 (M+H)+.

b) An analogous reaction to that described in example 5b, but starting with 2-{3-[(7-{3-[cyclopropyl(2-hydroxyethyl)amino]propoxy}-6-methoxyquinazolin-4-yl)amino]-1H-pyrazol-5-yl}-N-(3-fluorophenyl)acetamide (1.1 g, 2.0 mmol) yielded a mixture of di-tert-butyl 2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (150 mg, 10% yield) together with di-tert-butyl 2-{[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (730 mg, 52% yield) which was used in the next step:

$^1$H-NMR (DMSO d$_6$, TFA): 8.97 (s, 1H), 8.32 (s, 1H), 7.78 (d, 1H), 7.36 (m, 2H), 7.34 (s, 1H), 6.87 (m, 2H), 4.33 (m, 2H), 4.16 (m, 2H), 4.03 (s, 3H), 3.88 (s, 2H), 3.33 (m, 2H), 3.24 (m, 2H), 2.38 (m, 2H), 1.47 (s, 18H):

MS (+ve ESI): 702.5 (M+H)+.

EXAMPLE 19

Preparation of compound 19 in table 1—2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate (400 mg, 0.508 mmol) yielded compound 19 in table 1 (365 mg, 96% yield):

¹H-NMR (DMSO d₆, AcOD): 8.92 (s, 1H), 8.33 (s, 1H), 7.71 (m, 1H), 7.44 (s, 1H), 7.19 (m, 2H), 6.82 (s, 1H), 4.30 (m, 4H), 4.00 (s, 3H), 3.94 (s, 2H), 3.42 (m, 2H), 3.29 (m, 4H), 2.82 (m, 1H), 2.31 (m, 2H), 2.13 (m, 2H), 1.87 (m, 4H):

MS (+ve ESI): 676.4 (M+H)⁺.

di-tert-butyl 2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) Cyclobutane carbonyl chloride (5 ml, 43.8 mmol) was slowly added to a solution of ethyl glycinate (5.86 g, 42 mmol) in dichloromethane (100 ml) and triethylamine (14.6 ml, 105 mmol) at 0° C. The mixture was then stirred at ambient temperature for 14 hours. The reaction mixture was washed with a dilute hydrochloric acid (1.0 N), the organic phase was separated, dried and evaporated in vacuo to give a yellow solid. Recrystallisation from dichloromethane/petroleum ether yielded ethyl N-(cyclobutylcarbonyl)glycinate as a white solid (7.78 g, 100% yield):

¹H-NMR (DMSO d₆): 8.08 (t, 1H), 4.09 (q, 2H), 3.79 (s, 2H), 3.07 (m, 1H), 2.00-2.18 (m, 4H), 1.89 (m, 1H), 1.78 (m, 1H), 1.20 (t, 3H).

b) Ethyl N-(cyclobutylcarbonyl)glycinate (7.6 g, 41 mmol) in tetrahydrofuran (40 ml) was added to a solution of diborane (100 ml of a 1.0 N solution in tetrahydrofuran, 100 mmol) and heated at 60° C. for 24 hours. Additional diborane (20 ml of a 1.0 N solution in tetrahydrofuran, 20 mmol) was added to the mixture and heating was carried out for a further 8 hours. Methanol (20 ml) was added cautiously and the reaction stirred for 30 minutes at ambient temperature before slow addition of hydrochloric acid (6 ml of a 6.0 N solution). The reaction was concentrated in vacuo, dichloromethane was added and the solid material removed by suction filtration. The organic filtrate was dried, concentrated in vacuo and purified by chromatography on silica gel, eluting with dichloromethane/methanol (96:4) to dichloromethane/methanol/ammonia (7.0N) (94:5:1) to yield 2-((cyclobutylmethyl)amino)ethanol (4.16 g, 78% yield):

¹H-NMR (DMSO d₆, TFA): 8.38 (br s, 1H), 3.65 (t, 2H), 2.98 (m, 4H), 2.62 (m, 2H), 2.06 (m, 2H), 1.72-1.94 (m, 4H).

c) An analogous reaction to that described in example 6b, but starting with 2-((cyclobutylmethyl)amino)ethanol (129 mg, 1 mmol) yielded 2-{3-[(7-{3-[(cyclobutylmethyl)(2-hydroxyethyl)amino]propoxy}-6-methoxyquinazolin-4-yl)amino]-1H-pyrazol-5-yl}-N-(2,3-difluorophenyl)acetamide (134 mg, 75% yield):

¹H-NMR (DMSO d₆): 8.49 (s, 1H), 8.00 (s, 1H), 7.74 (m, 1H), 7.15-7.30 (m, 3H), 6.75 (m, 1H), 4.25 (m, 2H), 3.96 (s, 3H), 3.86 (s, 2H), 3.60-3.80 (m, 2H), 3.30-3.40 (m, 4H), 2.50-2.80 (m, 4H), 1.60-2.40 (m, 7H):

MS (+ve ESI): 596.2 (M+H)⁺.

d) An analogous reaction to that described in example 6c, but starting with 2-{3-[(7-{3-[(cyclobutylmethyl)(2-hydroxyethyl)amino]propoxy}-6-methoxyquinazolin-4-yl)amino]-1H-pyrazol-5-yl}-N-(2,3-difluorophenyl)acetamide (773 mg, 1.3 mmol) yielded di-tert-butyl 2-{(cyclobutylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate (400 mg, 40% yield):

¹H-NMR (DMSO d₆): 8.45 (s, 1H), 7.99 (s, 1H), 7.72 (m, 1H), 7.20 (m, 3H), 6.83 (s, 1H), 4.15 (s, 2H), 3.94 (s, 3H), 3.85 (m, 4H), 2.60 (m, 4H), 2.47 (m, 3H), 1.88 (m, 4H), 1.75 (m, 2H), 1.60 (m, 2H), 1.36 (s, 18H):

MS (+ve ESI): 788.8 (M+H)⁺.

EXAMPLE 20

Preparation of compound 20 in table 1—2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl dihydrogen phosphate An analogous reaction to that described in example 1, but starting with di-tert-butyl 2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl phosphate (450 mg, 0.56 mmol) yielded compound 20 in table 1 (405 mg, 46% yield):

¹H-NMR (DMSO d₆, TFA): 8.95 (s, 1H), 8.32 (s, 1H), 7.65 (d, 1H), 7.39 (s, 1H), 7.36 (m, 1H), 6.89 (m, 1H), 6.83 (s, 1H), 4.31 (t, 2H), 4.27 (m, 2H), 4.01 (s, 2H), 3.86 (s, 2H), 3.57 (br s, 2H), 3.54 (m, 2H), 3.43 (t, 2H), 2.97 (m, 2H), 2.33 (m, 2H):

MS (+ve ESI): 686.4 (M+H)⁺.

di-tert-butyl 2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl phosphate used as starting material was obtained as follows:

a) A solution of 3-bromo-1,1,1-trifluoropropane (5.5 ml, 51.6 mmol) in dioxane (50 ml) was heated with ethanol amine (3 ml, 51.25 mmol) at 60° C. for 36 hours in the presence of potassium carbonate (14.2 g, 102 mmol). The solvent was evaporated in vacuo and the residue was purified by chromatography on silica gel, eluting with dichloromethane/methanol (95:5) to dichloromethane/methanol/ammonia (7.0 N) (95:5:1) to yield 2-((3,3,3-trifluoropropyl)amino)ethanol (4.47 g, 55% yield):

¹H-NMR (DMSO d₆, TFA): 3.56 (t, 2H), 2.97 (t, 2H), 2.82 (t, 2H), 2.57 (m, 2H).

b) An analogous reaction to that described in example 5a, but starting with 2-((3,3,3-trifluoropropyl)amino)ethanol (221 mg, 1.55 mmol) yielded N-(3-fluorophenyl)-2-{3-[(7-{3-[(2-hydroxyethyl)(3,3,3-trifluoropropyl)amino]propoxy}-6-methoxyquinazolin-4-yl)amino]-1H-pyrazol-5-yl}acetamide (77 mg, 41% yield):

¹H-NMR (DMSO d₆, TFA): 8.96 (s, 1H), 8.29 (s, 1H), 7.63 (d, 1H), 7.31-7.40 (m, 2H), 7.33 (s, 1H), 6.89 (t, 1H), 6.83 (s, 1H), 4.29 (t, 2H), 3.99 (s, 3H), 3.84 (s, 2H), 3.79 (t, 2H), 3.51 (m, 2H), 3.38 (m, 2H), 2.91 (m, 2H), 2.29 (m, 2H):

MS (+ve ESI): 606.2 (M+H)⁺.

c) An analogous reaction to that described in example 5b, but starting with N-(3-fluorophenyl)-2-{3-[(7-{3-[(2-hydroxyethyl)(3,3,3-trifluoropropyl)amino]propoxy}-6-methoxyquinazolin-4-yl)amino]-1H-pyrazol-5-yl}acetamide (651 mg, 1.07 mmol) yielded di-tert-butyl 2-[[3-({4-[(5-{2-[(3-fluorophenyl)amino]-2-oxoethyl}-1H-pyrazol-3-yl)amino]-6-methoxyquinazolin-7-yl}oxy)propyl](3,3,3-trifluoropropyl)amino]ethyl phosphate (455 mg, 53% yield):

¹H-NMR (DMSO d₆): 10.45 (s, 1H), 10.15 (s, 1H), 8.44 (s, 1H), 7.98 (s, 1H), 7.62 (d, 1H), 7.35 (m, 1H), 7.33 (s, 1H), 7.13 (s, 1H), 6.89 (t, 1H), 6.82 (s, 1H), 4.16 (t, 2H), 3.93 (s, 3H), 3.87 (q, 2H), 3.76 (s, 2H), 2.73 (m, 4H), 2.66 (t, 2H), 2.42 (m, 2H), 1.90 (m, 2H), 1.37 (s, 18H):

MS (+ve ESI): 797.9 (M+H)⁺.

EXAMPLE 21

Preparation of compound 21 in table 1—2-{allyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with 2-{allyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl di-tert-butyl phosphate (310 mg, 0.408 mmol) yielded compound 21 in table 1 (293 mg, 100% yield):

$^1$H-NMR (DMSO $d_6$, AcOD): 8.92 (s, 1H), 8.32 (s, 1H), 7.70 (m, 1H), 7.43 (s, 1H), 7.19 (m, 2H), 6.82 (s, 1H), 6.05 (m, 1H), 5.63 (m, 1H), 5.56 (m, 1H), 4.30 (m, 4H), 4.00 (s, 3H), 3.93 (m, 4H), 3.45 (m, 2H), 3.33 (m, 2H), 2.33 (m, 2H):

MS (+ve ESI): 648.3 (M+H)$^+$.

2-{allyl[3-({4-[(5-{2-[(2,3-difluorophenyl)amino]-2-oxoethyl}-1H-pyrazol-3-yl)amino]-6-methoxyquinazolin-7-yl}oxy)propyl)amino}ethyl di-tert-butyl phosphate used as starting material was obtained as follows:

a) Ethylene oxide (2.5 ml, 50 mmol—cooled to −20° C.) was added to a solution of allylamine (14 g, 250 mmol) in methanol (20 ml) at −20° C. The mixture was stirred at ambient temperature for 14 hours, the solvent was evaporated in vacuo and the residual oil was purified by distillation (b.p. 140° C./14 mmHg) to yield 2-(allylamino)ethanol (4.2 g, 84% yield):

$^1$H-NMR (DMSO $d_6$): 5.83 (m, 1H), 5.14 (m, 1H), 5.02 (m, 1H), 3.43 (m, 2H), 3.14 (m, 2H), 2.50 (m, 2H).

b) An analogous reaction to that described in example 6b, but starting with 2-(allylamino)ethanol (101 mg, 1 mmol) yielded 2-{3-[(7-{3-[allyl(2-hydroxyethyl)amino]propoxy}-6-methoxyquinazolin-4-yl)amino]-1H-pyrazol-5-yl}-N-(2,3-difluorophenyl)acetamide (99 mg, 58% yield):

$^1$H-NMR (DMSO $d_6$, TFA): 8.97 (s, 1H), 8.32 (s, 1H), 7.77 (m, 1H), 7.33 (s, 1H), 7.18 (m, 2H), 6.87 (s, 1H), 6.01 (m, 1H), 5.60 (m, 2H), 4.31 (t, 2H), 4.02 (s, 3H), 3.94 (m, 4H), 3.82 (t, 2H), 3.35 (m, 4H), 2.34 (m, 2H):

MS (+ve ESI): 568.2 (M+H)$^+$.

c) An analogous reaction to that described in example 6c, but starting with 2-{3-[(7-{3-[allyl(2-hydroxyethyl)amino]propoxy}-6-methoxyquinazolin-4-yl)amino]-1H-pyrazol-5-yl}-N-(2,3-difluorophenyl)acetamide (1.0 g, 1.76 mmol) yielded 2-{allyl[3-({4-[(5-{2-[(2,3-difluorophenyl)amino]-2-oxoethyl}-1H-pyrazol-3-yl)amino]-6-methoxyquinazolin-7-yl]oxy)propyl]amino}ethyl di-tert-butyl phosphate (310 mg, 23% yield):

$^1$H-NMR (DMSO $d_6$, TFA): 8.97 (s, 1H), 8.30 (s, 1H), 7.75 (m, 1H), 7.32 (s, 1H), 7.20 (m, 2H), 6.85 (s, 1H), 6.00 (m, 1H), 5.74 (m, 2H), 4.30 (m, 4H), 4.01 (s, 3H), 3.95 (m, 4H), 3.50 (m, 2H), 3.37 (m, 2H), 2.30 (m, 2H), 1.45 (s, 18H):

MS (+ve ESI): 760.5 (M+H)$^+$.

EXAMPLE 22

Preparation of compound 22 in table 1—2-{cyclobutyl[3-({4-[(5-{2-[(2,3-difluorophenyl)amino]-2-oxoethyl}1-H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate (450 mg, 0.58 mmol) yielded compound 22 in table 1 (420 mg, 98% yield):

$^1$H-NMR (DMSO $d_6$, AcOD): 8.91 (s, 1H), 8.31 (s, 1H), 7.72 (m, 1H), 7.42 (s, 1H), 7.20 (m, 2H), 6.82 (s, 1H), 4.28 (m, 4H), 4.00 (s, 3H), 3.94 (s, 3H), 3.35 (m, 2H), 3.25 (m, 2H), 2.41 (m, 2H), 2.25 (m, 4H), 1.70 (m, 2H):

MS (+ve ESI): 662.5 (M+H)$^+$.

di-tert-butyl 2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) An analogous reaction to that described in example 6b, but starting with 2-(cyclobutylamino)ethanol (117 mg, 1 mmol—prepared according to D. F. Morrow et al, *J. Med. Chem.* 1973, 16, 736-9.) and potassium iodide (103 mg, 0.62 mmol) in dimethylacetamide (2 ml) at 95° C. for 4 hours under argon yielded 2-{3-[(7-{3-[cyclobutyl(2-hydroxyethyl)amino]propoxy}-6-methoxyquinazolin-4-yl)amino]-1H-pyrazol-5-yl}-N-(2,3-difluorophenyl)acetamide (97 mg, 56% yield):

$^1$H-NMR (DMSO $d_6$, TFA): 8.92 (s, 1H), 8.27 (s, 1H), 7.74 (m, 1H), 7.29 (s, 1H), 7.15-7.20 (m, 2H), 6.83 (s, 1H), 4.30 (m, 2H), 3.98 (s, 3H), 3.98 (m, 3H), 3.68-3.80 (m, 2H), 3.20-3.30 (m, 2H), 3.15 (m, 2H), 2.30 (m, 2H), 2.22 (m, 4H), 1.65-1.82 (m, 2H):

MS (+ve ESI): 582.2 (M+H)$^+$.

b) An analogous reaction to that described in example 6c, but starting with 2-{3-[(7-{3-[cyclobutyl(2-hydroxyethyl)amino]propoxy}-6-methoxyquinazolin-4-yl)amino]-1H-pyrazol-5-yl}-N-(2,3-difluorophenyl)acetamide (668 mg, 1.15 mmol) yielded di-tert-butyl 2-{cyclobutyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate (450 mg, 51% yield):

$^1$H-NMR (DMSO $d_6$): 8.44 (s, 1H), 7.98 (s, 1H), 7.70 (m, 1H), 7.18 (m, 3H), 6.83 (s, 1H), 4.15 (t, 2H), 3.90 (s, 3H), 3.85 (m, 4H), 3.15 (m, 1H), 2.62 (m, 4H), 1.90 (m, 4H), 1.75 (m, 2H), 1.53 (m, 2H), 1.39 (s, 18H):

MS (+ve ESI): 774.8 (M+H)$^+$.

EXAMPLE 23

Preparation of compound 23 in table 1—2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate (360 mg, 0.46 mmol) yielded compound 23 in table 1 (330 mg, 95% yield):

$^1$H-NMR (DMSO $d_6$, AcOD): 8.91 (s, 1H), 8.32 (s, 1H), 7.70 (m, 1H), 7.43 (s, 1H), 7.20 (m, 2H), 6.82 (s, 1H), 4.31 (m, 4H), 4.00 (s, 3H), 3.94 (s, 2H), 3.80 (m, 1H), 3.48 (m, 2H), 3.36 (m, 2H), 2.33 (m, 2H), 2.08 (m, 2H), 1.75 (m, 4H), 1.58 (m, 2H):

MS (+ve ESI): 676.5 (M+H)$^+$.

di-tert-butyl 2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) An analogous reaction to that described in example 6b, but starting with 2-(cyclopentylamino)ethanol (129 mg, 1 mmol-prepared according to D. F. Morrow et al. *J. Med. Chem.* 1973,16,736-9.) yielded 2-{3-[(7-{3-[cyclopentyl (2-hydroxyethyl)amino]propoxy}-6-methoxyquinazolin-4-yl)amino]-1H-pyrazol-5-yl}-N-(2,3-difluorophenyl)acetamide (86 mg, 48% yield):

$^1$H-NMR (DMSO d$_6$, TFA): 8.93 (s, 1H), 8.28 (s, 1H), 7.73 (m, 1H), 7.30 (s, 1H), 7.14 (m, 2H), 6.83 (s, 1H), 4.29 (m, 2H), 3.98 (s, 3H), 3.93 (s, 2H), 3.78 (m, 3H), 3.37 (m, 2H), 3.26 (m, 2H), 2.30 (m, 2H), 2.09 (m, 2H), 1.74 (m, 4H), 1.72 (m, 2H):

MS (+ve ESI): 596.2 (M+H)$^+$.

b) An analogous reaction to that described in example 6c, but starting with 2-{3-[(7-{3-[cyclopentyl(2-hydroxyethyl) amino]propoxy}-6-methoxyquinazolin-4-yl)amino]-1H-pyrazol-5-yl}-N-(2,3-difluorophenyl)acetamide (654 mg, 1.1 mmol) yielded di-tert-butyl 2-{cyclopentyl[3-({4-[(5-{2-[(2,3-difluorophenyl)amino]-2-oxoethyl}-1H-pyrazol-3-yl)amino]-6-methoxyquinazolin-7-yl}oxy)propyl] amino}ethyl phosphate (364 mg, 42% yield):

$^1$H-NMR (DMSO d$_6$): 8.44 (s, 1H), 7.99 (s, 1H), 7.70 (m, 1H), 7.18 (m, 3H), 6.83 (s, 1H), 4.15 (m, 2H), 3.90 (s, 3H), 3.83 (m, 4H), 3.07 (m, 1H), 2.68 (m, 4H), 1.90 (m, 2H), 1.72 (m, 2H), 1.55 (m, 2H), 1.48 (m, 2H), 1.35 (m, 20H):

MS (+ve ESI): 789.0 (M+H)$^+$.

EXAMPLE 24

Preparation of compound 24 in table 1—2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate Hydrochloric acid (1.05 ml of a 4.0 N solution in dioxane, 4.2 mmol) was added to a stirred suspension of di-tert-butyl 2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (519 mg, 0.7 mmol) in dichloromethane (15 ml) and dioxane (30 ml) and the reaction stirred for 7 hours at 45° C. The precipitate was recovered by suction filtration, the residue taken up in dichloromethane/methanol (8:2) and the solid material removed by filtration. The organic filtrate was evaporated in vacuo and the residue triturated with diethyl ether to yield compound 24 in table 1 (430 mg, 88% yield):

$^1$H-NMR (DMSO d$_6$, ACOH): 8.91 (s, 1H), 8.32 (s, 1H), 7.64 (m, 1H), 7.39 (m, 3H), 6.90 (m, 1H), 6.80 (s, 1H), 4.32 (m, 4H), 4.00 (s, 3H), 3.87 (s, 2H), 3.57 (m, 2H), 3.48 (m, 2H), 2.95 (m, 1H), 2.40 (m, 2H), 1.18 (m, 2H), 0.92 (m, 2H):

MS (+ve ESI): 630.4 (M+H)$^+$.

di-tert-butyl 2-{cyclopropyl[3-({4-[(5-{2-[(3-fluorophenyl) amino]-2-oxoethyl}-1H-pyrazol-3-yl)amino]-6-methoxyquinazolin-7-yl}oxy)propyl]amino}ethyl phosphate used as starting material was obtained as follows:

a) Di-tert-butyl-diethylphosphoramidite (523 μl, 2.1 mmol) was added within 5 minutes to a solution of 2-{3-[(7-{3-[cyclopropyl(2-hydroxyethyl)amino]propoxy}-6-methoxyquinazolin-4-yl)amino]-1H-pyrazol-5-yl}-N-(3-fluorophenyl)acetamide (793 mg, 1.4 mmol) in dimethylformamide (8 ml) in the presence of tetrazole (245 mg, 3.5 mmol) at ambient temperature under argon and the mixture was stirred for 1.5 hours. The solution was cooled to 5° C., cumene hydroperoxide (426 mg, 2.8 mmol) was slowly added, and the mixture stirred at 50° C. for 1 hour and at ambient temperature for a further 1 hour. The mixture was cooled to 5° C. and triethyl phosphite (415 mg, 2.5 mmol) was added and the reaction stirred at ambient temperature for 1 hour. The solution was diluted with water, extracted with ethyl acetate and the organic phase was separated, dried and concentrated. The resultant oil was purified by chromatography on silica gel, eluting with dichloromethane/methanol (98:2) to dichloromethane/methanol/ammonia (7.0 N) (95:5:1), to give di-tert-butyl 2-{cyclopropyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate as an off-white solid (630 mg, 59% yield):

$^1$H-NMR (DMSO d$_6$, TFA): 8.97 (s, 1H), 8.32 (s, 1H), 7.65 (d, 1H), 7.35 (m, 3H), 6.86 (m, 2H), 4.33 (m, 4H), 4.03 (s, 3H), 3.87 (s, 2H), 3.66 (m, 2H), 3.53 (m, 2H), 3.00 (m, 1H), 2.38 (m, 2H), 1.45 (s, 18H), 1.07 (m, 2H), 0.96 (m, 2H):

MS (+ve ESI): 759.7 (M+H)$^+$.

EXAMPLE 25

Preparation of compound 25 in table 1—2-[(cyclopropylmethyl)[3-({4-[(5-{2-[(2,3-difluorophenyl) amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{(cyclopropylmethyl)[3-({4-[(5-{2-[(2,3-difluorophenyl)amino]-2-oxoethyl}-1H-pyrazol-3-yl)amino]-6-methoxyquinazolin-7-yl}oxy)propyl] amino}ethyl phosphate (725 mg, 0.94 mmol) yielded compound 25 in table 1 (661 mg, 90% yield):

$^1$H-NMR (DMSO d$_6$, TFA): 8.95 (s, 1H), 8.32 (s, 1H), 7.74 (m, 1H), 7.39 (s, 1H), 7.21 (m, 2H), 6.84 (s, 1H), 4.32 (t, 2H), 4.28 (m, 2H), 4.01 (s, 3H), 3.95 (s, 2H), 3.56 (br s, 2H), 3.46 (t, 2H), 3.19 (d, 2H), 2.32 (m, 2H), 1.18 (m, 1H), 0.68 (m, 2H), 0.47 (m, 2H):

MS (+ve ESI): 662.4 (M+H)$^+$.

di-tert-butyl 2-{(cyclopropylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) Ethylchloroformate (4.2 ml, 37 mmol) was added to a stirred solution of cyclopropylmethylamine (3.00 ml, 34.6 mmol) and triethylamine (7 ml) in dichloromethane (35 ml) at 0° C. over 30 minutes. The reaction was stirred at ambient temperature for 2 hours, water (20 ml) was added to the mixture, and the pH adjusted to 3 by addition of 2.0 N hydrochloric acid. The organic phase was separated, dried and concentrated in vacuo to yield ethyl (cyclopropylmethyl) carbamate (5.9 g, 100% yield):

$^1$H-NMR (CDCl$_3$): 7.24 (br s, 1H), 3.24 (m, 2H), 1.43 (t, 3H), 1.04 (m, 1H), 0.59 (m, 2H), 0.29 (m, 2H):

MS (+ve ESI): 172 (M+H)$^+$.

b) A solution of ethyl (cyclopropylmethyl) carbamate (5.90 g, 34.6 mmol) in tetrahydrofuran (30 ml) was added at ambient temperature to a solution of diborane (130 ml of a 1.0 N solution in tetrahydrofuran, 130 mmol) and chlorotrimethylsilane (34 ml, 268 mmol) and the mixture stirred at ambient temperature for 48 hours. Methanol (20 ml) was added and the reaction stirred for 30 minutes at ambient temperature. Dichloromethane (25 ml) was added, followed by hydrochloric acid (4 ml of a 6.0 N solution, 24 mmol) and the reaction was stirred at ambient temperature for 30 minutes. Methanolic ammonia (7.0 N) was added, the white solid was collected by suction filtration and the organic filtrate was evaporated in vacuo. Purification by chromatography on silica gel, eluting with dichloromethane to dichloromethane/methanol (95:5) to dichloromethane/methanol/ammonia (7.0 N) (90:9:1), yielded 2-((cyclopropylmethyl)amino)ethanol as a pale yellow liquid (2.99 g, 75% yield):

$^1$H-NMR (DMSO d$_6$, TFA): 3.66 (t, 2H), 3.02 (t, 2H), 2.84 (d, 2H), 1.06 (m, 1H), 0.58 (m, 2H), 0.35 (m, 2H).

c) An analogous reaction to that described in example 6b, but starting with 2-(cyclopropylmethyl)amino)ethanol (115 mg, 1 mmol) yielded 2-{3-[(7-{3-[(cyclopropylmethyl)(2-hydroxyethyl)amino]propoxy}-6-methoxyquinazolin-4-yl)amino]-1H-pyrazol-5-yl}-N-(2,3-difluorophenyl)acetamide (6 mg, 3% yield):

$^1$H-NMR (DMSO d$_6$): 10.23 (s, 1H), 10.16 (s, 1H), 8.44 (s, 1H), 7.98 (s, 1H), 7.72 (m, 1H), 7.18 (m, 2H), 7.14 (s, 1H), 6.84 (s, 1H), 4.32 (s, 1H), 4.18 (t, 2H), 3.93 (s, 3H), 3.85 (s, 2H), 3.45 (m, 2H), 2.69 (t, 2H), 2.58 (t, 2H), 2.35 (d, 2H), 1.90 (m, 2H), 0.83 (m, 1H), 0.41 (m, 2H), 0.08 (m, 2H):

MS (+ve ESI): 582.2 (M+H)$^+$.

d) An analogous reaction to that described in example 6c, but starting with 2-{3-[(7-{3-[(cyclopropylmethyl)(2-hydroxyethyl)amino]propoxy}-6-methoxyquinazolin-4-yl)amino]-1H-pyrazol-5-yl}-N-(2,3-difluorophenyl)acetamide (673 mg, 1.16 mmol) yielded di-tert-butyl 2-{(cyclopropylmethyl)[3-({4-[(5-{2-[(2,3-difluorophenyl)amino]-2-oxoethyl}-1H-pyrazol-3-yl)amino]-6-methoxyquinazolin-7-yl}oxy)propyl]amino}ethyl phosphate (110 mg, 12% yield):

$^1$H-NMR (DMSO d$_6$): 10.23 (s, 1H), 10.15 (s, 1H), 8.44 (s, 1H), 7.98 (s, 1H), 7.72 (t, 1H), 7.19 (m 2H), 7.13 (s, 1H), 6.83 (s, 1H), 4.17 (t, 2H), 3.93 (s, 3H), 3.88 (q, 2H), 3.85 (s, 2H), 2.76 (t, 2H), 2.72 (t, 2H), 2.38 (d, 2H), 1.91 (m, 2H), 1.37 (s, 18H), 0.83 (m, 1H), 0.42 (m, 2H), 0.09 (m, 2H):

MS (+ve ESI):774.7 (M+H)$^+$.

EXAMPLE 26

Preparation of Compound 26 in Table 1—2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl dihydrogen phosphate An analogous reaction to that described in example 1, but starting with di-tert-butyl 2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (416 mg, 0.55 mmol) yielded compound 26 in table 1 (455 mg, 100% yield):

$^1$H-NMR (DMSO d$_6$, TFA): 8.94 (s, 1H), 8.31 (s, 1H), 7.65 (d, 1H), 7.38 (m, 2H), 7.36 (s, 1H), 6.90 (m, 1H), 6.83 (s, 1H), 4.30 (t, 2H), 4.22 (m, 2H), 4.01 (s, 3H), 3.94 (m, 1H), 3.86 (s, 2H), 3.37 (s, 2H), 3.27 (br s, 2H), 2.35 (t, 2H), 2.26 (m, 4H), 1.77 (m, 1H), 1.68 (m, 1H):

MS (+ve ESI):644.2 (M+H)$^+$.

di-tert-butyl 2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate used as starting material was obtained as follows:

a) An analogous reaction to that described in example 5a, but starting with 2-(cyclobutylamino)ethanol (178 mg, 1.55 mmol) yielded 2-{3-[(7-{3-[cyclobutyl(2-hydroxyethyl)amino]propoxy}-6-methoxyquinazolin-4-yl)amino]-1H-pyrazol-5-yl}-N-(3-fluorophenyl)acetamide (42 mg, 24% yield):

$^1$H-NMR (DMSO d$_6$, TFA): 8.96 (s, 1H), 8.29 (s, 1H), 7.64 (d, 1H), 7.36 (m, 2H), 7.34 (s, 1H), 6.90 (t, 1H), 6.83 (s, 1H), 4.29 (t, 2H), 4.00 (s, 3H), 3.94 (m, 1H), 3.85 (s, 2H), 3.75 (m, 2H), 3.25 (m, 2H), 3.17 (m, 2H), 2.08-2.39 (m, 6H), 1.76 (m, 1H), 1.69 (m, 1H):

MS (+ve ESI):564.2 (M+H)$^+$.

b) An analogous reaction to that described in example 5b, but starting with 2-{3-[(7-{3-[cyclobutyl(2-hydroxyethyl)amino]propoxy}-6-methoxyquinazolin-4-yl)amino]-1H-pyrazol-5-yl}-N-(3-fluorophenyl)acetamide (474 mg, 0.84 mmol) yielded di-tert-butyl 2-{cyclobutyl[3-({4-[(5-{2-[(3-fluorophenyl)amino]-2-oxoethyl}-1H-pyrazol-3-yl)amino]-6-methoxyquinazolin-7-yl}oxy)propyl]amino}ethyl phosphate (109 mg, 17% yield):

$^1$H-NMR (DMSO d$_6$): 10.46 (s, 1H), 10.16 (s, 1H), 8.44 (s, 1H), 7.98 (s, 1H), 7.62 (d, 1H), 7.34 (m, 1H), 7.33 (s, 1H), 7.13 (s, 1H), 6.89 (t, 1H), 6.82 (s, 1H), 4.15 (t, 2H), 3.93 (s, 3H), 3.84 (q, 2H), 3.76 (s, 2H), 3.16 (m, 1H), 2.64 (t, 2H), 2.59 (t, 2H), 1.96 (m, 2H), 1.88 (m, 2H), 1.77 (m, 2H), 1.55 (m, 2H), 1.38 (s, 18H):

MS (+ve ESI):756.7 (M+H)$^+$.

EXAMPLE 27

Preparation of Compound 27 in Table 2—2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl dihydrogen phosphate An analogous reaction to that described in example 1, but starting with di-tert-butyl 2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl phosphate (230 mg, 0.32 mmol) yielded compound 27 in table 2 (230 mg, 95% yield) as a white solid:

$^1$H-NMR (DMSO d$_6$): 12.00 (s, 1H), 10.40 (s, 1H), 8.95 (s, 1H), 8.80 (d, 1H), 7.70-7.80 (m, 1H), 7.40 (d, 1H), 7.35 (s, 1H), 7.15-7.25 (m, 2H), 6.70 (s, 1H), 4.20-4.30 (m, 2H), 4.05-4.15 (m, 2H), 3.90 (s, 2H), 3.50-3.60 (m, 2H), 3.10-3.25 (m, 2H), 2.27 (m, 1H), 2.10-2.20 (m, 2H), 1.70-1.90 (m, 2H), 1.20 (t, 2H):

MS (+ve ESI):618 (M+H)$^+$,
MS (−ve ESI):616 (M−H)$^−$.

di-tert-butyl 2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl phosphate used as starting material was obtained as follows:

a) Dimethylformamide (0.1 ml) was added to a stirred suspension of 7-(benzyloxy)quinazolin-4(3H)-one (4.00 g, 15.9 mmol) in thionyl chloride (25 ml) and the reaction heated at 85° C. for 1 hour. The reaction was cooled, the excess thionyl chloride was evaporated in vacuo and the residue was azeotroped with toluene (2×25 ml) before being taken up in dimethylacetamide (20 ml). 5-amino-1H-pyrazol-3-ylacetic acid (2.27 g, 15.9 mmol) and was added and the reaction was heated at 90° C. for 2.5 hours. The reaction was cooled to ambient temperature, poured into ice-water (200 ml) and the solid which precipitated was collected by suction filtration to yield (3-{[7-(benzyloxy)quinazolin-4-yl]amino}-1H-pyrazol-5-yl)acetic acid (3.92 g, 60% yield) as a pale orange solid:

$^1$H-NMR (DMSO d$_6$): 12.70 (br s, 1H), 8.75 (s, 1H), 8.70 (d, 1H), 7.57 (m, 2H), 7.35-7.50 (m, 4H), 7.30 (s, 1H), 6.70 (s, 1H), 5.35 (s, 2H), 3.70 (s, 2H):

MS (+ve ESI):376 (M+H)$^+$,
MS (−ve ESI):374 (M−H)$^−$.

b) Phosphorus oxychloride (1.00 ml, 11.6 mmol) was added to a stirred suspension of 2,3-difluoroaniline (1.44 g, 11.6 mmol), (3-{[7-(benzyloxy)quinazolin-4-yl]amino})-1H-pyrazol-5-yl)acetic acid (3.82 g, 9.30 mmol) and pyridine (40 ml) at 0° C. The reaction was stirred for 1 hour at ambient temperature, then cooled to 0° C. and treated with additional phosphorus oxychloride (0.5 ml) before being allowed to warm to ambient temperature over 1 hour. The reaction was poured into 20% aqueous hydrochloric and the resultant solid was collected by suction filtration. Prolonged drying in vacuo, yielded 2-(3-{[7-(benzyloxy)quinazolin-4-yl]amino}-1H-pyrazol-5-yl)-N-(2,3-difluorophenyl)acetamide (4.90 g, 100% yield) as an orange solid which contained some water:

$^1$H-NMR (DMSO d$_6$): 11.30 (s, 1H), 10.30 (s, 1H), 8.80 (s, 1H), 8.70 (d, 1H), 7.80-7.80 (m, 1H), 7.50-7.60 (m, 2H), 7.35-7.45 (m, 5H), 7.30 (s, 1H), 7.10-7.20 (m, 2H), 6.80 (s, 1H), 5.40 (s, 2H), 3.90 (s, 2H):

MS (+ve ESI):487 (M+H)$^+$,

MS (−ve ESI):485 (M−H)$^−$.

c) 2-(3-{[7-(benzyloxy)quinazolin-4-yl]amino}-1H-pyrazol-5-yl)-N-(2,3-difluorophenyl)acetamide (4.90 g, 9.30 mmol) was added to trifluoroacetic acid (75 ml) and the reaction heated at 90° C. for 4 hours. The reaction was cooled, the excess trifluoroacetic acid was removed in vacuo and the residue was taken up in methanol (30 ml). The methanolic solution was added dropwise to aqueous sodium hydrogen carbonate solution (100 ml) causing precipitation of an orange solid. Collection of the solid followed by washing with water yielded N-(2,3-difluorophenyl)-2-{3-[(7-hydroxyquinazolin-4-yl)amino]-1H-pyrazol-5-yl}acetamide (3.60 g, 97% yield) as a pale brown solid after drying in vacuo:

$^1$H-NMR (DMSO d$_6$): 12.50 (br s, 1H), 10.30 (s, 1H), 8.70 (s, 1H), 8.60 (d, 1H), 7.70-7.80 (m, 1H), 7.30-7.40 (m, 2H), 7.10 (d, 1H), 7.00 (s, 1H), 6.80 (br s, 1H), 3.80 (s, 2H):

MS (+ve ESI):397 (M+H)$^+$,

MS (−ve ESI):395 (M−H)$^−$.

d) Methanesulphonyl chloride (864 mg, 7.58 mmol) was added dropwise to a solution of N-(tert-butoxycarbonyl)piperidin-4-ylmethanol (1.63 g, 7.58 mmol) and triethylamine (1.40 ml, 10.0 mmol) in dry tetrahydrofuran (15 ml) at 0° C. and the reaction was stirred at this temperature for 1 hour. The reaction was filtered, the residue was washed with diethyl ether and the combined organic phases were evaporated in vacuo to afford a colourless oil. The oil was taken up in dimethylacetamide (10 ml), N-(2,3-difluorophenyl)-2-{3-[(7-hydroxyquinazolin-4-yl)amino]-1H-pyrazol-5-yl}acetamide (2.00 g, 5.07 mmol) and potassium carbonate (1.39 g, 10.0 mmol) were added and the reaction heated at 70° C. for 16 hours. The reaction mixture was concentrated in vacuo and purified by flash chromatography on silica gel, eluting with 0-5% methanol in dichloromethane, to yield tert-butyl 4-[({4-[(5-{2-[(2,3-difluorophenyl)amino]-2-oxoethyl}-1H-pyrazol-3-yl)amino]quinazolin-7-yl}oxy)methyl]piperidin-1-ylcarboxylate (1.11 g, 38% yield) as a yellow solid:

$^1$H-NMR (DMSO d$_6$): 12.50 (s, 1H), 10.30 (d, 2H), 8.60-8.70 (m, 2H), 7.70-7.80 (m, 1H), 7.30-7.40 (m, 4H), 6.90 (s, 1H), 4.00-4.10 (m, 4H), 3.90 (s, 2H), 2.80-2.90 (m, 2H), 2.00-2.10 (m, 1H), 1.80-1.90 (m, 2H), 1.50 (s, 9H), 1.30-1.40 (m, 2H):

MS (+ve ESI):594 (M+H)$^+$,

MS (−ve ESI):592 (M−H)$^−$.

e) Trifluoroacetic acid (5 ml) was added to a solution of tert-butyl 4-[({4-[(5-{2-[(2,3-difluorophenyl)amino]-2-oxoethyl}-1H-pyrazol-3-yl)amino]quinazolin-7-yl}oxy)methyl]piperidin-1-ylcarboxylate (1.11 g, 1.897 mmol) in dichloromethane (25 ml) and the reaction stirred for 30 minutes at ambient temperature. The volatile substances were removed in vacuo and the product was purified by reverse phase hplc. The fractions from the hplc were concentrated in vacuo to 20% of their original volume and made basic with sodium carbonate, causing precipitation of an orange solid. The solid was collected by suction filtration, dissolved in dichloromethane:methanol (1:9) and washed with water. Solvent evaporation in vacuo yielded N-(2,3-difluorophenyl)-2-(3-{[7-(piperidin-4-ylmethoxy)quinazolin-4-yl]amino}-1H-pyrazol-5-yl)acetamide (612 mg, 66% yield) as an orange powdery solid:

$^1$H-NMR (DMSO d$_6$): 12.40 (s, 1H), 10.20 (br s, 2H), 8.50-8.60 (m, 2H), 7.70-7.80 (m, 1H), 7.00-7.20 (m, 4H), 6.70 (br s, 1H), 4.20 (br s, 1H), 4.00 (d, 2H), 3.90 (s, 2H), 3.10-3.20 (m, 2H), 2.90-3.00 (m, 2H), 1.90-2.00 (m, 1H), 1.70-1.80 (m, 2H), 1.20-1.30 (m, 2H):

MS (+ve ESI):494 (M+H)$^+$,

MS (−ve ESI):492 (M−H)$^−$.

f) Sodium acetoxyborohydride (392 mg, 1.86 mmol) was added to a solution of tert-butyldimethylsilyloxyacetaldehyde (324 mg, 1.86 mmol), N-(2,3-difluorophenyl)-2-(3-{[7-(piperidin-4-ylmethoxy)quinazolin-4-yl]amino}-1H-pyrazol-5-yl)acetamide (612 mg, 1.24 mmol), acetic acid (0.42 ml, 7.4 mmol) in methanol (10 ml) and tetrahydrofuran (30 ml) and the reaction stirred for 18 hours at ambient temperature. Additional sodium acetoxyborohydride (392 mg, 1.86 mmol) and tert-butyldimethylsilyloxyacetaldehyde (324 mg, 1.86 mmol) were added and the reaction stirred for 10 minutes before being concentrated in vacuo. The residue was purified by flash chromatography on a Biotage 40M cartridge, eluting with methanol:dichloromethane (7:93) and then 7.0N ammonia:methanol (1:99) to give 2-{3-[(7-{[1-(2-{[tert-butyl(dimethyl)silyl]oxy}ethyl)piperidin-4-yl]methoxy}quinazolin-4-yl)amino]-1H-pyrazol-5-yl}-N-(2,3-difluorophenyl)acetamide (410 mg, 51% yield) as a pale orange solid after solvent evaporation and drying in vacuo:

$^1$H-NMR (DMSO d$_6$): 12.40 (s, 1H), 10.15 (s, 1H), 10.10 (s, 1H), 8.50 (s, 1H), 8.45 (d, 1H), 7.60-7.70 (m, 1H), 7.00-7.20 (m, 4H), 6.70 (s, 1H), 3.90 (d, 2H), 3.70 (s, 2H), 3.60 (t, 2H), 2.80-2.90 (m, 2H), 2.40 (t, 2H), 1.90-2.00 (m, 2H), 1.70-1.80 (m, 3H), 1.20-1.30 (m, 2H), 0.80 (s, 9H), 0.00 (s, 6H):

MS (+ve ESI):652 (M+H)$^+$,

MS (−ve ESI):650 (M−H)$^−$.

g) Tetra-n-butylammonium fluoride (0.69 ml of a 1.0N solution in tetrahydrofuran, 0.69 mmol) was added to a solution of 2-{3-[(7-{[1-(2-{[tert-butyl(dimethyl)silyl]oxy}ethyl)piperidin-4-yl]methoxy}quinazolin-4-yl)amino]-1H-pyrazol-5-yl}-N-(2,3-difluorophenyl)acetamide (410 mg, 0.63 mmol) in tetrahydrofuran (10 ml). The reaction was stirred for 18 hours at ambient temperature, during which time 2 additional portions of tetra-n-butylammonium fluoride (0.69 mmol) were added. The reaction was concentrated in vacuo and the residue was purified by flash chromatography on a Biotage 40S cartridge, eluting with methanol:dichloromethane (25:75) and then 7.0N ammonia :methanol (1:99) to give N-(2,3-difluorophenyl)-2-{3-[(7-{[1-(2-hydroxyethyl)piperidin-4-yl]methoxy}quinazolin-4-yl)amino]-1H-pyrazol-5-yl}acetamide (258 mg, 76% yield) as a pale orange solid:

$^1$H-NMR (DMSO d$_6$): 12.30 (s, 1H), 10.30 (br s, 1H), 8.50 (br s, 2H), 7.76 (m, 1H), 7.10-7.40 (m, 4H), 6.90 (br s, 1H), 4.40 (br s, 1H), 4.10 (d, 2H), 3.80 (br s, 2H), 3.40-3.50 (m,

2H), 2.90-3.00 (m, 2H), 2.50 (t, 2H), 2.00-2.10 (m, 2H), 1.70-1.80 (m, 3H), 1.30-1.40 (m, 2H):

MS (+ve ESI):538 (M+H)$^+$,

MS (−ve ESI):536 (M−H)$^-$.

h) An analogous reaction to that described in example 6c, but starting with N-(2,3-difluorophenyl)-2-{3-[(7-{1-(2-hydroxyethyl)piperidin-4-yl]methoxy}quinazolin-4-yl)amino]-1H-pyrazol-5-yl}acetamide (235 mg, 0.44 mmol) yielded di-tert-butyl 2-{4-[({4-[(5-{2-[(2,3-difluorophenyl)amino]-2-oxoethyl}-1H-pyrazol-3-yl)amino]quinazolin-7-yl}oxy)methyl]piperidin-1-yl}ethyl phosphate (232 mg, 73% yield) as a white solid:

$^1$H-NMR (DMSO d$_6$): 12.30 (s, 1H), 10.20 (d, 2H), 8.40 (br s, 2H), 7.60-7.70 (m, 1H), 7.30-7.40 (m, 4H), 6.80 (br s, 1H), 4.05 (d, 2H), 3.92 (m, 2H), 3.80 (br s, 2H), 2.80-2.90 (m, 2H), 2.50 (t, 2H), 2.00-2.10 (m, 2H), 1.60-1.70 (m, 3H), 1.40 (s, 18H), 1.20-1.30 (m, 2H):

MS (+ve ESI):730 (M+H)$^+$,

MS (−ve ESI):728 (M−H)$^-$.

EXAMPLE 28

Preparation of Compound 28 in Table 3—2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl dihydrogen phosphate An analogous reaction to that described in example 1, but starting with di(tert-butyl) 2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl phosphate (302 mg, 0.422 mmol) yielded compound 28 in table 3 (300 mg, 100% yield) as a white solid:

$^1$H-NMR (DMSO d$_6$): 12.00 (s, 1H), 10.30 (s, 1H), 8.90 (d, 1H), 7.65-7.75 (m, 1H), 7.50-7.60 (m, 2H), 7.10-7.25 (m, 2H), 6.70 (s, 1H), 4.35 (t, 2H), 4.20-4.30 (m, 2H), 3.90 (s, 2H), 3.40-3.50 (m, 2H), 3.25-3.35 (m, 2H), 3.10-3.20 (m, 2H), 2.20-2.40 (M, 2H), 1.30 (t, 3H):

MS (+ve ESI):606 (M+H)$^+$,

MS (−ve ESI):604 (M−H)$^-$.

di(tert-butyl) 2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl phosphate used as starting material was obtained as follows:

a) 2-Amino-4-fluorobenzoic acid (15 g, 96 mmol) was dissolved in 2-methoxyethanol (97 ml). Formamidine acetate (20.13 g, 193.4 mmol) was added and the mixture heated to reflux for 18 hours. The reaction was cooled, concentrated and the residue stirred in aqueous ammonium hydroxide (0.01 N, 250 ml) for 1 hour. The suspension was filtered, washed with water and dried over phosphorus pentoxide to yield 7-fluoroquinazolin-4(3H)-one as an off-white solid (10.35 g, 65% yield):

$^1$H-NMR (DMSO d$_6$): 12.32 (br s, 1H), 8.19 (dd, 1H), 8.14 (s, 1H), 7.45 (dd, 1H), 7.39 (m, 1H):

MS (−ve ESI):163 (M−H)$^-$,

MS (+ve ESI):165 (M+H)$^+$.

b) Sodium hydride (14.6 g, 365 mmol) was added at 0° C. to a solution of 1,3-propanediol (27.8 g, 365 mmol) in dimethylformamide (70 ml). 7-Fluoroquinazolin-4(3H)-one (10 g, 60.9 mmol) was added portionwise and the reaction mixture heated at 60° C., then at 110° C. for 3 hours. The reaction was cooled to 0° C., quenched with water (280 ml) and adjusted to pH 5.9. The resulting suspension was filtered, washed with water then ether and dried over phosphorus pentoxide to afford 7-(3-hydroxypropoxy)quinazolin-4(3H)-one as a white powder (12.41 g, 92% yield):

$^1$H-NMR (DMSO d$_6$): 11.90 (br s, 1H), 8.04 (s, 1H), 8.00 (d, 1H), 7.10 (m, 2H), 4.17 (t, 2H), 3.58 (t, 2H), 1.92 (m, 2H):

MS (+ve ESI):221 (M+H)$^+$.

c) 7-(3-hydroxypropoxy)quinazolin-4(3H)-one (10.5 g, 47.7 mmol) and thionyl chloride (100 ml, 137 mmol) were combined. Dimethylformamide (1 ml) was added and the reaction mixture heated to 85° C. for 1 hour. The mixture was cooled to room temperature, diluted with toluene and evaporated to dryness. This was repeated until all thionyl chloride was removed. The residue was dissolved in dichloromethane and washed with a saturated sodium bicarbonate solution. The aqueous layer was extracted with dichloromethane. The organics were combined, dried (magnesium sulphate) and concentrated to leave a yellow solid. Trituration with ether removed a less soluble impurity and the ether filtrate was concentrated to leave 4-chloro-7-(3-chloropropoxy)quinazoline as an off-white solid (8.5 g, 70% yield):

$^1$H-NMR (DMSO d$_6$): 13.25 (br s, 1H), 8.34 (s, 1H), 8.06 (d, 1H), 7.17 (m, 2H), 4.21 (t, 2H), 3.83 (t, 2H), 2.23 (m, 2H):

MS (+ve ESI):257, 259 (M+H)$^+$.

d) 4-chloro-7-(3-chloropropoxy)quinazoline (2.5 g, 9.72 mmol) and (3-amino-1H-pyrazol-5-yl)acetic acid (1.37 g, 9.72 mmol) were combined in dimethylformamide (25 ml). A solution of 4M HCl in dioxane (1.25 ml, 4.8 mmol) was added and the reaction heated to 90° C. for 40 minutes. The solution was cooled to room temperature, diluted with water (250 ml) and filtered through celite. The acidic solution was basified to pH 4.9 and the yellow powder filtered. (At pH 3, a red solid precipitated which was isolated, suspended in water and basified to pH 12. Careful adjustment back to pH 4.8 resulted in the precipitation of a yellow powder, which was combined with the first crop). The solid was washed with diethyl ether and dried over phosphorus pentoxide to yield (3-{[7-(3-chloropropoxy)quinazolin-4-yl]amino}-1H-pyrazol-5-yl)acetic acid as a pale orange solid (2.88 g, 82% yield):

$^1$H-NMR (DMSO d$_6$): 12.60 (br s, 2H), 10.78 (br s, 1H), 8.65 (s, 1H), 8.60 (d, 1H), 7.26 (d, 1H), 7.22 (s, 1H), 6.67 (s, 1H), 4.28 (t, 2H), 3.83 (t, 2H), 3.67 (s, 2H), 2.24 (m, 2H)

MS (−ve ESI):360, 362 (M−H)$^-$,

MS (+ve ESI):362, 364 (M+H)$^+$.

e) 2,3-difluoroaniline (1.15 g, 8.95 mmol) was added to a suspension of (3-{[7-(3-chloropropoxy)quinazolin-4-yl]amino}-1H-pyrazol-5-yl)acetic acid (2.70 g, 7.46 mmol) in pyridine (30 ml) and the reaction cooled to 0° C. Phosphorous oxychloride (1.14 g, 7.46 mmol) was added dropwise and the reaction stirred at 0° C. for 1 hour. The reaction was warmed to ambient temperature and more phosphorous oxychloride (0.5 ml) added. The reaction was stirred for 4.5 hours. The reaction mixture was diluted with ethyl acetate: ether (100 ml:37 ml) and stirred for 18 hours. The precipitate was filtered, suspended in water and neutralised with ammonium hydroxide (7%, 15 ml). The resultant yellow suspension was filtered, washed with water and dried (phosphorous pentoxide) to yield 2-(3-{[7-(3-chloropropoxy)quinazolin-4-yl]amino}-1H-pyrazol-5-yl)-N-(2,3-difluorophenyl)acetamide as an orange powder (3.15 g, 89% yield):

$^1$H-NMR (DMSO d$_6$): 10.64 (br s, 1H), 10.27 (s, 1H), 8.60 (s, 1H), 8.55 (d, 1H), 7.70 (m, 1H), 7.20 (m, 6H), 6.68 (s, 1H), 4.27 (t, 2H), 3.83 (m, 4H), 2.25 (m, 2H):

MS (−ve ESI):471, 473 (M−H)$^-$,

MS (+ve ESI):473, 475 (M+H)$^+$.

f) 2-(3-{[7-(3-chloropropoxy)quinazolin-4-yl]amino}-1H-pyrazol-5-yl)-N-(2,3-difluorophenyl)acetamide (300 mg, 0.634 mmol), potassium iodide (210 mg, 1.27 mmol), dimethylamine (2 ml) and 2-(ethylamino)ethanol (226 mg, 2.54 mmol) were combined and heated to 50° C. for 72 hours. The reaction was diluted with dichloromethane (20 ml) and loaded onto a 40S silica biotage column. Elution with dichloromethane followed by increased polarity to dichloromethane:methanol (9:1), then dichloromethane: methanol: ammonia (9:1:0.8) yielded N-(2,3-difluorophenyl)-2-{3-[(7-{3-[ethyl(2-hydroxyethyl)amino]propoxy}-quinazolin-4-yl)amino]-1H-pyrazol-5-yl}acetamide as a pale pink solid (181 mg, 54% yield):

$^1$H-NMR (DMSO d$_6$): 12.35 (s, 1H), 10.25 (s, 2H), 8.52 (s, 2H), 7.71 (m, 1H), 7.16 (m, 4H), 6.78 (s, 1H), 4.33 (t, 1H), 4.17 (t, 2H), 3.84 (s, 2H), 3.43 (m, 2H), 2.60 (t, 2H), 2.49 (m, 4H), 1.88 (m, 2H), 0.96 (t, 3H):

MS (−ve ESI):524 (M−H)$^−$,
MS (+ve ESI):526 (M+H)$^+$.

g) An analogous reaction to that described in example 6c, but starting with N-(2,3-difluorophenyl)-2-{3-[(7-{3-[ethyl(2-hydroxyethyl)amino]propoxy}-quinazolin-4-yl)amino]-1H-pyrazol-5-yl}acetamide (372 mg, 0.71 mmol) yielded di(tert-butyl) 2-[[3-({4-[(5-{2-[(2,3-difluorophenyl)amino]-2-oxoethyl}-1H-pyrazol-3-yl)amino]-quinazolin-7-yl}oxy)propyl](ethyl)amino]ethyl phosphate (304 mg, 60% yield) as a pale yellow solid:

$^1$H-NMR (DMSO d$_6$): 12.30 (s, 1H), 10.20 (d, 2H), 8.60-8.70 (m, 2H), 7.70-7.80 (m, 1H), 7.05-7.25 (m, 4H), 6.80 (br s, 1H), 4.20 (t, 2H), 3.80-3.90 (m, 4H), 2.60-2.70 (m, 4H), 2.40-2.50 (m, 2H), 1.80-1.90 (m, 2H), 1.40 (s, 18H), 0.95 (t, 3H):

MS (+ve ESI):718 (M+H)$^+$,
MS (−ve ESI):716 (M−H)$^−$.

EXAMPLE 29

Preparation of Compound 29 in Table 3—2-[[3-({4-[(5-{2-[(2,3-difluorophenyl)amino]-2-oxoethyl)-1H-pyrazol-3-yl)amino]-quinazolin-7-yl}oxy)propyl](isopropyl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-quinazolin-7-yl}oxy)propyl](isopropyl)amino]ethyl phosphate (372 mg, 0.51 mmol) yielded compound 29 in table 3 (342 mg, 92% yield) as a pale yellow solid:

$^1$H-NMR (DMSO d$_6$): 12.00 (s, 1H), 10.30 (s, 1H), 8.90 (s, 1H), 8.80 (d, 1H), 7.60-7.70 (m, 1H), 7.40-7.50 (m, 2H), 7.10-7.20 (m, 2H), 6.70 (s, 1H), 4.40 (t, 2H), 4.20-4.30 (m, 2H), 3.90 (s, 2H), 3.70-3.80 (m, 1H), 3.40-3.50 (m, 2H), 3.20-3.30 (m, 2H), 2.30-2.40 (m, 2H), 1.35 (d, 6H):

MS (+ve ESI):620 (M+H)$^+$,
MS (−ve ESI):618 (M−H)$^−$.

di-tert-butyl 2-[[3-({4-[(5-{2-[(2,3-difluorophenyl)amino]-2-oxoethyl}-1H-pyrazol-3-yl)amino]-quinazolin-7-yl}oxy)propyl](isopropyl)amino]ethyl phosphate used as starting material was obtained as follows:

a) An analogous reaction to that described in example 28f, but starting with 2-(isopropylamino)ethanol (262 mg, 2.54 mmol) yielded N-(2,3-difluorophenyl)-2-{3-[(7-{3-[isopropyl(2-hydroxyethyl)amino]propoxy}-quinazolin-4-yl)amino]-1H-pyrazol-5-yl}acetamide as an off-white solid (182 mg, 53% yield):

$^1$H-NMR (DMSO d$_6$): 12.35 (s, 1H), 10.20 (s, 1H), 8.50 (s, 2H), 7.71 (m, 1H), 7.20 (m, 4H), 6.78 (s, 1H), 4.29 (br s, 1H), 4.19 (t, 2H), 3.85 (s, 2H), 3.38 (dt, 2H), 2.88 (m, 1H), 2.55 (t, 2H), 2.45 (t, 2H), 1.82 (m, 2H), 0.93 (d, 6H):

MS (−ve ESI):538 (M−H)$^−$,
MS (+ve ESI):540 (M+H)$^+$.

b) An analogous reaction to that described in example 6c, but starting with N-(2,3-difluorophenyl)-2-{3-[(7-{3-[isopropyl(2-hydroxyethyl)amino]propoxy}-quinazolin-4-yl)amino]-1H-pyrazol-5-yl}acetamide (414 mg, 0.77 mmol) yielded di-tert-butyl 2-[[3-({4-[(5-{2-[(2,3-difluorophenyl)amino]-2-oxoethyl}-1H-pyrazol-3-yl)amino]-quinazolin-7-yl}oxy)propyl](isopropyl)amino]ethyl phosphate (374 mg, 67% yield) as a white solid:

$^1$H-NMR (DMSO d$_6$): 12.40 (s, 1H), 10.20 (d, 2H), 8.50-8.60 (m, 2H), 7.60-7.80 (m, 1H), 7.10-7.30 (m, 4H), 6.80 (br s, 1H), 4.15-4.25 (m, 2H), 3.80-3.90 (m, 4H), 2.85-3.00 (m, 1H), 2.50-2.65 (m, 4H), 1.80-1.90 (m, 2H), 1.40 (s, 18H), 1.00 (s, 3H), 0.98 (s, 3H):

MS (+ve ESI):b 732 (M+H)$^+$,
MS (−ve ESI):730 (M−H)$^−$.

EXAMPLE 30

Preparation of Compound 30 in Table 3—3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl dihydrogen phosphate An analogous reaction to that described in example 1, but starting with di-tert-butyl 3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl phosphate (490 mg, 0.67 mmol) yielded compound in table 3 (480 mg, 99% yield) as a pale yellow dihydrochloride salt:

$^1$H-NMR (DMSO d$_6$): 12.00 (s, 1H), 10.35 (s, 1H), 9.20 (br s, 1H), 8.90 (s, 1H), 8.80 (d, 1H), 7.72 (m, 1H), 7.50 (d, 2H), 7.40 (s, 1H), 7.20-7.30 (m, 2H), 6.70 (s, 1H), 4.30 (t, 2H), 3.90-4.00 (m, 2H), 3.85 (s, 2H), 3.10-3.20 (m, 2H), 2.20-2.30 (m, 2H), 2.00-2.10 (m, 2H), 1.40 (d, 6H):

MS (+ve ESI):620 (M+H)$^+$.
MS (−ve ESI):618 (M−H)$^−$.

di-tert-butyl 3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl phosphate used as starting material was obtained as follows:

a) An analogous reaction to that described in example 28f, but starting with 3-amino-3-methylbutan-1-ol (655 mg, 6.36 mmol) yielded N-(2,3-difluorophenyl)-2-{3-[(7-{3-[(3-hydroxy-1,1-dimethylpropyl)amino]propoxy}quinazolin-4-yl)amino]-1H-pyrazol-5-yl}acetamide as an off-white solid (450 mg, 39% yield):

$^1$H-NMR (DMSO d$_6$): 12.40 (s, 1H), 10.20 (br s, 2H), 8.60-8.70 (m, 2H), 7.70-7.80 (m, 1H), 7.25-7.35 (m, 4H), 6.80 (br s, 1H), 4.20 (t, 2H), 3.90 (s, 2H), 3.60 (t, 2H), 2.70 (t, 2H), 1.90-2.00 (m, 2H), 1.50 (t, 2H), 1.00 (s, 6H):

MS (+ve ESI):540 (M+H)$^+$,
MS (−ve ESI):538 (M−H)$^−$.

b) An analogous reaction to that described in example 6c, but starting with N-(2,3-difluorophenyl)-2-{3-[(7-{3-[(3-hydroxy-1,1-dimethylpropyl)amino]propoxy}quinazolin-4-yl)amino]-1H-pyrazol-5-yl}acetamide (212 mg, 0.38 mmol) yielded di-tert-butyl 3-{[3-({4-[(5-{2-[(2,3-difluorophenyl)amino]-2-oxoethyl}-1H-pyrazol-3-yl)amino]quinazolin-7-yl}oxy)propyl]amino}-3-methylbutyl phosphate (204 mg, 72% yield) as a pale yellow solid:

¹H-NMR (DMSO d₆): 12.40 (s, 1H), 10.20 (d, 2H), 8.50-8.60 (m, 2H), 7.65-7.75 (m, 1H), 7.20-7.30 (m, 4H), 6.80 (s, 1H), 4.30 (t, 2H), 3.90-4.00 (m, 2H), 3.85 (s, 2H), 2.70-2.80 (m, 2H), 1.90-2.00 (m, 2H), 1.60-1.70 (m, 2H), 1.40 (s, 18H), 1.10 (s, 6H):

MS (+ve ESI):732 (M+H)⁺,
MS (−ve ESI):730 (M−H)⁻.

EXAMPLE 31

Preparation of Compound 31 in Table 3—2-{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}ethyl dihydrogen phosphate An analogous reaction to that described in example 1, but starting with di(tert-butyl) 2-{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}ethyl phosphate (204 mg, 0.27 mmol) yielded compound 31 in table 3 (198 mg, 97% yield) as a pale yellow dihydrochloride salt:

¹H-NMR (DMSO d₆): 12.00 (s, 1H), 10.80 (s, 1H), 10.50 (s, 1H), 8.95 (s, 1H), 8.80 (d, 1H), 7.60-7.80 (m, 1H), 7.50 (d, 1H), 7.40 (s, 1H), 7.20-7.30 (m, 2H), 6.70 (s, 1H), 4.35 (t, 2H), 3.90-4.00 (m, 1H), 3.85 (s, 2H), 3.60-3.70 (m, 1H), 3.30-3.50 (m, 2H), 3.00-3.25 (m, 2H), 2.20-2.40 (m, 4H), 1.90-2.10 (m, 3H), 1.70-1.80 (m, 1H):

MS (+ve ESI):632 (M+H)⁺,
MS (−ve ESI):630 (M−H)⁻.

di(tert-butyl) 2-{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}ethyl phosphate used as starting material was obtained as follows:

a) An analogous reaction to that described in example 28f, but starting with (2S)-2-(2-hydroxyethyl)pyrrolidine (731 mg, 6.36 mmol) yielded N-(2,3-difluorophenyl)-2-{3-[(7-{3-[(2S)-2-(2-hydroxyethyl)pyrrolidin-1-yl]propoxy}-quinazolin-4-yl)amino]-1H-pyrazol-5-yl}acetamide as a white solid (260 mg, 22% yield):

¹H-NMR (DMSO d₆): 12.30 (s, 1H), 10.20 (s, 2H), 8.40-8.70 (m, 2H), 7.70-7.80 (m, 1H), 7.10-7.30 (m, 4H), 6.80 (br s, 1H), 4.30-4.50 (m, 1H), 4.20 (t, 2H), 3.80-3.90 (m, 2H), 3.30-3.50 (m, 2H), 3.10-3.20 (m, 1H), 2.90-3.00 (m. 1H), 2.30-2.40 (m, 1H), 2.10-2.20 (m, 1H), 1.90-2.00 (m, 1H), 1.75-1.85 (m, 3H), 1.68 (m, 1H), 1.50-1.60 (m, 2H), 1.30-1.40 (m, 2H):

MS (+ve ESI):520 (M+H)⁺,
MS (−ve ESI):550 (M−H)⁻.

b) An analogous reaction to that described in example 6c, but starting with N-(2,3-difluorophenyl)-2-{3-[(7-{3-[(2S)-2-(2-hydroxyethyl)pyrrolidin-1-yl]propoxy}-quinazolin-4-yl)amino]-1H-pyrazol-5-yl}acetamide (212 mg, 0.38 mmol) yielded di(tert-butyl) 2-{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}ethyl phosphate (204 mg, 72% yield) as a pale yellow solid:

¹H-NMR (DMSO d₆, 373K): 12.00 (s, 1H), 9.90 (s, 2H), 9.80 (s, 1H), 8.50 (s, 1H), 8.40 (d, 1H), 7.70-7.80 (m, 1H), 7.20-7.30 (m, 4H), 6.70 (br s, 1H), 4.30 (t, 2H), 3.90-4.00 (m, 2H), 3.80 (s, 2H), 3.00-3.10 (m, 1H), 2.40-2.50 (m, 1H), 2.20-2.30 (m, 1H), 1.80-2.00 (m, 4H), 1.70-1.80 (m, 2H), 1.62 (m, 1H), 1.40-1.50 (m, 1H), 1.40 (s, 18H), 0.90-1.00 (m, 1H):

MS (+ve ESI):742 (M+H)⁺,
MS (−ve ESI): 740 (M−H)⁻.

EXAMPLE 32

Preparation of Compound 32 in Table 3—{(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate An analogous reaction to that described in example 1, but starting with di(tert-butyl) {(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl phosphate (355 mg, 0.49 mmol) yielded compound 32 in table 3 (355 mg, 100% yield) as a pale yellow dihydrochloride salt (as the dihydrate):

¹H-NMR (DMSO d₆): 12.00 (br s, 1H), 10.40 (s, 1H), 8.93 (s, 1H), 8.82 (d, 1H), 7.68 (m, 1H), 7.40-7.50 (m, 2H), 7.15-7.25 (m, 2H), 6.75 (s, 1H), 4.35 (t, 2H), 4.10-4.30 (m, 1H), 3.92 (s, 2H), 3.81 (m, 1H), 3.55-3.70 (m, 2H), 3.27 (m, 1H), 3.18 (m, 1H), 2.10-2.35 (m, 4H), 1.85-2.10 (m, 3H), 1.75-1.85 (m, 1H):

MS (+ve ESI):618 (M+H)⁺.

di(tert-butyl) {(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl phosphate used as starting material was obtained as follows:

a) An analogous reaction to that described in example 28f, but starting with D-prolinol (257 mg, 2.54 mmol) yielded N-(2,3-difluorophenyl)-2-{3-[(7-{3-[(2R)-2-(hydroxymethyl)pyrrolidin-1-yl]propoxy}-quinazolin-4-yl)amino]-1H-pyrazol-5-yl}acetamide as a pink solid (206 mg, 60% yield):

¹H-NMR (DMSO d₆): 11.60 (br s, 7H), 10.25 (s, 1H), 8.52 (m, 2H), 7.75 (m, 1H), 7.16 (m, 4H), 6.67 (s, 1H), 4.22 (t, 2H), 3.84 (s, 2H), 3.50 (d, 2H), 3.35 (m, 1H), 3.28 (m, 1H), 3.07 (m, 1H), 2.86 (m, 1H), 2.72 (m, 1H), 2.05 (m, 2H), 1.95 (m, 1H), 1.60-1.90 (m, 4H):

MS (−ve ESI):536 (M−H)⁻,
MS (+ve ESI):538 (M+H)⁺.

b) An analogous reaction to that described in example 6c, but starting with N-(2,3-difluorophenyl)-2-{3-[(7-{3-[(2R)-2-(hydroxymethyl)pyrrolidin-1-yl]propoxy}-quinazolin-4-yl)amino]-1H-pyrazol-5-yl}acetamide (437 mg, 0.81 mmol) yielded di(tert-butyl) {(2R)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl phosphate (355 mg, 60% yield) as a pale yellow solid:

¹H-NMR (DMSO d₆): 12.30 (br s, 1H), 10.20 (s, 2H), 8.50 (s, 2H), 7.68 (m, 1H), 7.10-7.20 (m, 4H), 6.78 (br s, 1H), 4.15 (t, 2H), 3.80 (m, 3H), 3.65 (m, 1H), 3.10 (m, 1H), 2.93 (m, 1H), 2.64 (m, 1H), 2.19 (m, 1H), 1.80-1.95 (m, 3H), 1.68 (m, 2H), 1.60 (m, 1H), 1.33 (s, 18H):

MS (−ve ESI):728 (M−H)⁻,
MS (+ve ESI):730 (M+H)⁺.

EXAMPLE 33

Preparation of Compound 33 in Table 3—2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl dihydrogen phosphate An analogous reaction to that described in example 1, but starting with di-tert-butyl 2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl phosphate (271 mg, 0.37 mmol) yielded compound 33 in table 3 (266 mg, 98% yield) as the dihydrochloride salt:

¹H-NMR (DMSO d₆): 12.02 (br s, 1H), 10.40 (s, 1H), 9.95 (s, 1H), 9.85 (s, 1H), 7.70 (s, 1H), 7.47 (m, 2H), 7.20 (m, 2H), 6.73 (s, 1H), 4.23-4.37 (m, 4H), 3.92 (s, 2H), 3.43 (m, 2H), 3.32 (m, 2H), 3.13 (n, 2H), 2.28 (m, 2H), 1.76 (m, 2H), 0.95 (t, 3H):

MS (+ve ESI):618.4 (M+H)⁺,
MS (−ve ESI):620.4 (M−H)⁻.

di-tert-butyl 2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl phosphate used as starting material was obtained as follows:

a) An analogous reaction to that described in example 28f, but starting with 2-(propylamino)ethanol (262 mg, 2.54 mmol) yielded N-(2,3-difluorophenyl)-2-{3-[(7-{3-[(2-hydroxyethyl)(propyl)amino]propoxy}-quinazolin-4-yl)amino]-1H-pyrazol-5-yl}acetamide as a pink solid (168 mg, 49% yield):

¹H-NMR (DMSO d₆): 12.35 (s, 1H), 10.22 (s, 2H), 8.51 (s, 2H), 7.71 (m, 1H), 7.20 (m, 4H), 6.78 (s, 1H), 4.30 (t, 1H), 4.17 (t, 2H), 3.85 (s, 2H), 3.43 (m, 2H), 2.59 (t, 2H), 2.49 (m, 2H), 2.39 (t, 2H), 1.87 (m, 2H), 1.39 (m, 2H), 0.82 (t, 3H):

MS (−ve ESI):538 (M−H)⁻,
MS (+ve ESI):540 (M+H)⁺.

b) An analogous reaction to that described in example 6c, but starting with N-(2,3-difluorophenyl)-2-{3-[(7-{3-[(2-hydroxyethyl)(propyl)amino]propoxy}-quinazolin-4-yl)amino]-1H-pyrazol-5-yl}acetamide (690 mg, 1.28 mmol) yielded di-tert-butyl 2-[[3-({4-[(5-{2-[(2,3-difluorophenyl)amino]-2-oxoethyl}-1H-pyrazol-3-yl)amino]-quinazolin-7-yl}oxy)propyl](propyl)amino]ethyl phosphate (271 mg, 29% yield) as a pale yellow solid:

MS (−ve ESI):730 (M−H)⁻,
MS (+ve ESI):732 (M+H)⁺.

EXAMPLE 34

Preparation of Compound 34 in Table 3—2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl dihydrogen phosphate An analogous reaction to that described in example 1, but starting with di(tert-butyl) 2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl phosphate (400 mg, 0.54 mmol) yielded compound 34 in table 3 (360 mg, 95% yield) as a pale yellow dihydrochloride salt:

¹H-NMR (DMSO d₆): 12.00 (s, 1H), 10.34 (s, 1H), 8.93 (s, 1H), 8.85 (d, 1H), 7.68 (m, 1H), 7.47 (d, 1H), 7.44 (s, 1H), 7.20 (m, 2H), 6.74 (s, 1H), 4.33 (t, 2H), 4.28 (m, 2H), 3.93 (s, 2H), 3.44 (m, 2H), 3.36 (m, 2H), 3.16 (m, 2H), 2.30 (m, 2H), 1.71 (m, 2H), 1.34 (m, 2H), 0.93 (t, 3H):

MS (+ve ESI):634 (M+H)⁺.

di(tert-butyl) 2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl phosphate used as starting material was obtained as follows:

a) An analogous reaction to that described in example 28f, but starting with 2-(butylamino)ethanol (891 mg, 7.61 mmol) yielded N-(2,3-difluorophenyl)-2-{3-[(7-{3-[(2-hydroxyethyl)(butyl)amino]propoxy}-quinazolin-4-yl)amino]-1H-pyrazol-5-yl}acetamide as a pale yellow solid (625 mg, 45% yield):

¹H-NMR (DMSO d₆): 12.65 (s, 1H), 12.32 (s, 1H), 10.17 (m, 2H), 8.52 (m, 2H), 7.72 (m, 1H), 7.05-7.30 (m, 4H), 6.78 (br s, 1H), 4.30 (m, 1H), 4.20 (t, 2H), 3.85 (br s, 2H), 3.44 (m, 2H), 2.63 (m, 2H), 2.54 (m, 2H), 2.45 (m, 2H), 1.90 (m, 2H), 1.38 (m, 2H), 1.26 (m, 2H), 0.84 (t, 3H):

MS (+ve ESI):554 (M+H)⁺.

b) An analogous reaction to that described in example 6c, but starting with N-(2,3-difluorophenyl)-2-{3-[(7-{3-[(2-hydroxyethyl)(butyl)amino]propoxy}-quinazolin-4-yl)amino]-1H-pyrazol-5-yl}acetamide (605 mg, 1.09 mmol) yielded di(tert-butyl) 2-[[3-({4-[(5-{2-[(2,3-difluorophenyl)amino]-2-oxoethyl}-1H-pyrazol-3-yl)amino]-quinazolin-7-yl}oxy)propyl](butyl)amino]ethyl phosphate (400 mg, 50% yield) as a pale yellow solid:

¹H-NMR (CDCl₃): 12.80 (br s, 1H), 9.47 (br s, 1H), 9.40 (br s, 1H), 8.72 (s, 1H), 8.13 (d, 1H), 8.05 (m, 1H), 7.22 (s, 1H), 7.18 (d, 1H), 7.03 (m, 1H), 6.86 (m, 1H), 6.15 (br s, 1H), 4.15 (t, 2H), 4.00 (q, 2H), 3.83 (s, 2H), 2.73 (t, 2H), 2.64 (t, 2H), 2.47 (t, 2H), 1.93 (m, 2H), 1.48 (s, 18H), 1.44 (m, 2H), 1.29 (m, 2H), 0.89 (t, 3H):

MS (+ve ESI):746 (M+H)⁺.

EXAMPLE 35

Preparation of Compound 35 in Table 3—2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl dihydrogen phosphate An analogous reaction to that described in example 1, but starting with di-tert-butyl 2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl phosphate (405 mg, 0.53 mmol) yielded compound 35 in table 3 (388 mg, 100% yield) as a pale yellow dihydrochloride salt:

¹H-NMR (DMSO d₆): 12.00 (s, 1H), 10.33 (s, 1H), 8.93 (s, 1H), 8.83 (d, 1H), 7.69 (m, 1H), 7.49 (d, 1H), 7.41 (s, 1H), 7.20 (m, 2H), 6.74 (s, 1H), 4.32 (t, 2H), 4.29 (m, 2H), 3.93 (s, 2H), 3.77 (m, 1H), 3.46 (m, 2H), 3.35 (m, 2H), 2.31 (m, 2H), 2.08 (m, 2H), 1.83 (m, 2H), 1.74 (m, 2H), 1.57 (m, 2H):

MS (+ve ESI):646 (M+H)⁺.

di-tert-butyl 2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl phosphate used as starting material was obtained as follows:

a) An analogous reaction to that described in example 28f, but starting with 2-(cyclopentylamino)ethanol (1.00 g, 7.75 mmol) yielded N-(2,3-difluorophenyl)-2-{3-[(7-{3-[cyclopentyl(2-hydroxyethyl)amino]propoxy}-quinazolin-4-yl)amino]-1H-pyrazol-5-yl}acetamide as a pale yellow solid (533 mg, 37% yield):

¹H-NMR (DMSO d₆): 12.66 (s, 1H), 12.30 (s, 1H), 10.16 (m, 2H), 8.52 (m, 2H), 7.72 (m, 1H), 7.06-7.40 (m, 4H), 6.80 (s, 1H), 4.32 (n 1H), 4.19 (t, 2H), 3.85 (br s, 2H), 3.43 (m, 2H), 3.06 (m, 1H), 2.66 (m, 2H), 2.56 (m, 2H), 1.90 (m, 2H), 1.73 (m, 2H), 1.58 (m, 2H), 1.48 (m, 2H), 1.32 (m, 2H):

MS (+ve ESI):566 (M+H)⁺.

b) An analogous reaction to that described in example 6c, but starting with 2-{3-[(7-{3-[cyclopentyl(2-hydroxyethyl)amino]propoxy}-quinazolin-4-yl)amino]-1H-pyrazol-5-yl}-N-(2,3-difluorophenyl)acetamide (482 mg, 0.85 mmol) yielded di-tert-butyl 2-{cyclopentyl[3-({4-[(5-{2-[(2,3-difluorophenyl)amino]-2-oxoethyl}-1H-pyrazol-3-yl)amino]-quinazolin-7-yl}oxy)propyl]amino}ethyl phosphate (411 mg, 64% yield) as a pale yellow solid:

¹H-NMR (CDCl₃): 12.70 (br s), 1H), 9.35 (m, 2H), 8.71 (s, 1H), 8.05 (m, 2H), 7.20 (s, 1H), 7.12 (d, 1H), 7.01 (m, 1H), 6.86 (m, 1H), 6.17 (br s), 1H), 4.11 (t, 2H), 3.98 (q, 2H), 3.83 (s, 2H), 3.08 (m, 1H), 2.80 (t, 2H), 2.72 (t, 2H), 1.95 (m, 2H), 1.78 (m, 2H), 1.69 (m, 2H), 1.62 (m, 2H), 1.50 (s, 18H), 1.35 (m, 2H):

MS (+ve ESI):758 (M+H)⁺.

EXAMPLE 36

Preparation of Compound 36 in Table 3—{(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl dihydrogen phosphate An analogous reaction to that described in example 1, but starting with di(tert-butyl) {(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl phosphate (425 mg, 0.58 mmol) yielded compound 36 in table 3 (400 mg, 99% yield) as an off-white solid:

¹H-NMR (DMSO d₆): 12.00 (s, 1H), 10.35 (s, 1H), 8.94 (s, 1H), 8.85 (d, 1H), 7.67 (m, 1H), 7.47 (d, 1H), 7.43 (s, 1H), 7.20 (m, 2H), 6.74 (s, 1H), 4.34 (t, 2H), 4.15-4.32 (m, 2H), 3.92 (s, 2H), 3.78 (m, 1H), 3.52-3.72 (m, 2H), 3.30 (m, 1H), 3.19 (m, 1H), 2.24-2.42 (m, 2H), 2.20 (m, 1H), 2.02 (m, 1H), 1.96 (m, 1H), 1.82 (m, 1H):

MS (+ve ESI):618 (M+H)⁺.

di(tert-butyl) {(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl phosphate used as starting material was obtained as follows:

a) An analogous reaction to that described in example 28f, but starting with L-prolinol (770 mg, 7.62 mmol) yielded N-(2,3-difluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide as a pale yellow solid (547 mg, 40% yield):

¹H-NMR (DMSO d₆): 12.66 (s, 1H), 12.35 (s, 1H), 10.20 (m, 2H), 8.51 (m, 2H), 7.72 (m, 1H), 7.20 (m, 4H), 6.77 (br s, 1H), 4.21 (t, 2H), 3.81 (br s, 2H), 3.47 (m, 1H), 2.90-3.42 (m, 6H), 2.05 (m, 2H), 1.90 (m, 1H), 1.72 (m, 1H), 1.62 (m, 1H):

MS (+ve ESI):538 (M+H)⁺.

b) An analogous reaction to that described in example 6c, but starting with N-(2,3-difluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide (485 mg, 0.90 mmol) yielded di(tert-butyl) {(2S)-1-[3-({4-[(5-{2-[(2,3-difluorophenyl)amino]-2-oxoethyl}-1H-pyrazol-3-yl)amino]-quinazolin-7-yl}oxy)propyl]pyrrolidin-2-yl}methyl phosphate (430 mg, 65% yield) as a pale yellow solid:

¹H-NMR (CDCl₃): 12.70 (br s, 1H), 9.52 (br s, 1H), 9.37 (br s, 1H), 8.10 (s, 1H), 8.06 (m, 1H), 7.18 (s, 1H), 7.11 (d, 1H), 7.02 (m, 1H), 6.85 (m, 1H), 6.22 (br s, 1H), 4.12 (m, 2H), 3.92 (m, 1H), 3.84 (s, 2H), 3.68 (m, 1H), 3.12 (m, 1H), 2.97 (m, 1H), 2.73 (m, 1H), 2.48 (m, 1H), 2.25 (q, 1H), 1.85-2.05 (m, 3H), 1.55-1.85 (m, 3H), 1.45 (s, 18H):

MS (+ve ESI): 730 (M+H)⁺.

EXAMPLE 37

Preparation of Compound 37 in table 3—{(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate An analogous reaction to that described in example 1, but starting with di(tert-butyl) {(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl phosphate (654 mg, 0.92 mmol) yielded compound 37 in table 3 (596 mg, 97% yield) as an off-white dihydrochloride salt:

¹H-NMR (DMSO d₆): 11.95 (s, 1H), 10.73 (s, 1H), 8.94 (s, 1H), 8.82 (d, 1H), 7.65 (d, 1H), 7.46 (d, 1H), 7.38 (m, 3H), 6.90 (m, 1H), 6.74 (s, 1H), 4.32 (t, 2H), 4.21 (m, 2H), 3.85 (s, 2H), 3.78 (m, 1H), 3.64 (m, 2H), 3.29 (m, 1H), 3.19 (q, 1H), 2.31 (m, 3H), 2.20 (m, 1H), 2.00 (m, 3H), 1.81 (m, 1H):

MS (+ve ESI): 599.8 (M+H)⁺.

di(tert-butyl) {(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl phosphate used as starting material was obtained as follows:

a) An analogous reaction to that described in example 28f, but starting with L-prolinol (0.89 ml, 8.80 mmol) and 2-(3-{[7-(3-chloropropoxy)quinazolin-4-yl]amino}-1H-pyrazol-5-yl)-N-(3-fluorophenyl)acetamide (1.00 g, 2.20 mmol) yielded N-(3-fluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide as a cream solid (795 mg, 70% yield):

¹H-NM (DMSO d₆): 12.35 (m, 1H), 10.42 (s, 1H), 10.19 (m, 1H), 8.50 (s, 2H), 7.63 (d, 1H), 7.35 (m, 2H), 7.16 (m, 2H), 6.90 (t, 1H), 6.73 (m, 1H), 4.28 (t, 1H), 4.18 (t, 2H), 3.73 (s, 2H), 3.40 (m, 1H), 3.20 (m, 1H), 3.07 (m, 1H), 2.97 (m, 1H), 2.43 (m, 2H), 2.15 (q, 1H), 1.94 (m, 2H), 1.81 (m, 1H), 1.64 (m, 2H), 1.55 (m, 1H):

MS (+ve ESI): 520.1 (M+H)⁺.

b) An analogous reaction to that described in example 6c, but starting with N-(3-fluorophenyl)-2-{3-[(7-{3-[(2S)-2-(hydroxymethyl)pyrrolidin-1-yl]propoxy}-quinazolin-4-yl)amino]-1H-pyrazol-5-yl}acetamide (730 mg, 1.41 mmol) yielded di(tert-butyl) {(2S)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl phosphate (654 mg, 65% yield) as a pale yellow solid which was used in the next step without further characterisation. 2-(3-{[7-(3-chloropropoxy)quinazolin-4-yl]amino}-1H-pyrazol-5-yl)-N-(3-fluorophenyl)acetamide used as starting material was obtained as follows:

c) Pentafluorophenyl trifluoroacetate (23.25 g, 83 mmol) was added dropwise to a solution of (3-{[7-(3-chloropropoxy)quinazolin-4-yl]amino}-1H-pyrazol-5-yl)acetic acid (15.0 g, 41 mmol) and pyridine (6.7 ml, 83 mmol) in dimethylformamide (150 ml) with cooling to maintain the solution temperature at <23° C. The solution was stirred at ambient temperature for 30 minutes before addition of 3-fluoroaniline (9.22 g, 83 mmol). The reaction was stirred for 2.5 hours at ambient temperature and then a further portion of 3-fluoroaniline (2 ml) was added and the mixture was heated at 90° C. for 3 hours. The reaction mixture was poured into dilute hydrochloric acid (0.1 M) and ice (ca. 500 ml) and the resultant solid was filtered, washed with water and then diethyl ether and then dried to give 2-(3-{

[7-(3-chloropropoxy)quinazolin-4-yl]amino}-1H-pyrazol-5-yl)-N-(3-fluorophenyl)acetamide (17.7 g, 94% yield) as a brown solid:

¹H-NMR (DMSO d₆): 12.50 (br s, 1H), 10.42 (s, 1H), 8.59 (s, 1H), 8.54 (d, 1H), 7.62 (m, 1H), 7.35 (m, 2H), 7.24 (m, 1H), 7.19 (m, 1H), 6.90 (m, 1H), 6.67 (br s, 1H), 4.28 (t, 2H), 3.84 (t, 2H), 3.76 (s, 2H), 2.27 (quintet, 2H).

MS (+ve ESI): 455 (M+H)⁺.

EXAMPLE 38

Preparation of Compound 38 in Table 3—2-{cyclopentyl[3-({4-[(5-{2-[(3-fluorophenyl)amino]-2-oxoethyl}-1H-pyrazol-3-yl)amino]-quinazolin-7-yl}oxy)propyl]amino}ethyl dihydrogen phosphate An analogous reaction to that described in example 1, but starting with di-tert-butyl 2-{cyclopentyl[3-({4-[(5-{2-[(3-fluorophenyl)amino]-2-oxoethyl}-1H-pyrazol-3-yl)amino]-quinazolin-7-yl}oxy)propyl]amino}ethyl phosphate (572 mg, 0.77 mmol) yielded compound 38 in table 3 (568 mg, 100% yield):

¹H-NMR (DMSO d₆): 11.95 (s, 1H), 10.73 (s, 1H), 8.94 (s, 1H), 8.82 (d, 1H), 7.65 (d, 1H), 7.48 (d, 1H), 7.38 (m, 3H), 6.89 (m, 1H), 6.75 (s, 1H), 4.30 (m, 4H), 3.85 (s, 2H), 3.78 (t, 1H), 3.47 (m, 2H), 3.37 (m, 2H), 2.60 (m, 2H), 2.08 (m, 2H), 1.78 (m, 4H), 1.56 (m, 2H):

MS (+ve ESI): 628.4 (M+H)⁺.

di-tert-butyl 2-{cyclopentyl[3-({4-[(5-{2-[(3-fluorophenyl)amino]-2-oxoethyl}-1H-pyrazol-3-yl)amino]-quinazolin-7-yl}oxy)propyl]amino}ethyl phosphate used as starting material was obtained as follows:

a) An analogous reaction to that described in example 37a, but starting with 2-(cyclopentylamino)ethanol (1.13 ml, 8.80 mmol) yielded 2-{3-[(7-{3-[cyclopentyl(2-hydroxyethyl)amino]propoxy}-quinazolin-4-yl)amino]-1H-pyrazol-5-yl}-N-(3-fluorophenyl)acetamide as a cream solid (620 mg, 51% yield):

¹H-NMR (DMSO d₆): 12.31 (m, 1H), 10.39 (s, 1H), 10.16 (m, 1H), 8.50 (s, 2H), 7.62 (d, 1H), 7.35 (m, 2H), 7.16 (m, 2H), 6.90 (t, 1H), 6.78 (m, 1H), 4.29 (m, 1H), 4.16 (t, 2H), 3.74 (s, 2H), 3.40 (m, 2H), 3.05 (t, 1H), 2.66 (t, 2H), 2.54 (obs m, 2H), 1.86 (t, 2H), 1.72 (m, 2H), 1.54 (m, 2H), 1.45 (m, 2H), 1.31 (m, 2H)

MS (+ve ESI): 548.1 (M+H)⁺.

b) An analogous reaction to that described in example 6c, but starting with 2-{3-[(7-{3-[cyclopentyl(2-hydroxyethyl)amino]propoxy}-quinazolin-4-yl)amino]-1H-pyrazol-5-yl}-N-(3-fluorophenyl)acetamide (580 mg, 1.06 mmol) yielded di-tert-butyl 2-{cyclopentyl[3-({4-[(5-{2-[(3-fluorophenyl)amino]-2-oxoethyl}-1H-pyrazol-3-yl)amino]-quinazolin-7-yl}oxy)propyl]amino}ethyl phosphate (572 mg, 72% yield) as a pale yellow solid which was used in the next step without further characterisation.

EXAMPLE 39

Preparation of Compound 39 in Table 3—2-[[3-{4-[(5-{2-[(3-fluorophenyl)amino]-2-oxoethyl}-1H-pyrazol-3-yl)amino]-quinazolin-7-yl}oxy)propyl](ethyl)amino]ethyl dihydrogen phosphate An analogous reaction to that described in example 1, but starting with di(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate (539 mg, 0.77 mmol) yielded compound 39 in table 3 (504 mg, 99% yield) as a pale yellow dihydrochloride salt:

¹H-NMR (DMSO d₆): 11.98 (s, 1H), 10.79 (s, 1H), 8.93 (s, 1H), 8.83 (d, 1H), 7.65 (d, 1H), 7.47 (d, 1H), 7.38 (m, 3H), 6.89 (t, 1H), 6.74 (s, 1H), 4.32 (t, 2H), 4.28 (m, 2H), 3.85 (s, 2H), 3.42 (m, 2H), 3.34 (m, 2H), 3.27 (q, 2H), 2.29 (m, 2H), 1.28 (t, 3H):

MS (+ve ESI): 587.8 (M+H)⁺.

di(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate used as starting material was obtained as follows:

a) An analogous reaction to that described in example 37a, but starting with N-(ethylamino)ethanol (1.07 ml, 11.0 mmol) yielded N-(3-fluorophenyl)-2-{3-[(7-{3-[ethyl(2-hydroxyethyl)amino]propoxy}-quinazolin-4-yl)amino]-1H-pyrazol-5-yl}acetamide as a yellow solid (660 mg, 59% yield):

¹H-NMR (DMSO d₆): 12.31 (m, 1H), 10.39 (s, 1H), 10.15 (m, 1H), 8.51 (s, 2H), 7.62 (d, 1H), 7.35 (m, 2H), 7.16 (m, 2H), 6.90 (t, 1H), 6.78 (m, 1H), 4.29 (m, 1H), 4.20 (t, 2H), 3.76 (s, 2H), 3.45 (m, 2H), 3.30 (m, 4H), 2.61 (t, 2H), 1.89 (t, 2H), 0.95 (t, 3H):

MS (+ve ESI): 508.4 (M+H)⁺.

b) An analogous reaction to that described in example 6c, but starting with N-(3-fluorophenyl)-2-{3-[(7-{3-[ethyl(2-hydroxyethyl)amino]propoxy}-quinazolin-4-yl)amino]-1H-pyrazol-5-yl}acetamide (620 mg, 1.22 mmol) yielded di(tert-butyl) 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl phosphate (539 mg, 63% yield) as a pale yellow solid which was used in the next step without further characterisation.

Compound 39, synthesised above as the dihydrochloride salt, could also be prepared as the free base according to the following method: I c) An analogous reaction to that described in example 6d, but starting with Compound 39 yielded the free base of Compound 39 as a pale yellow solid:

¹H-NMR (DMSO d₆): 10.53 (s, 1H), 8.57 (s, 1H), 8.54 (d, 1H), 7.62 (d, 1H), 7.37 (m, 2H), 7.27 (s, 1H), 7.21 (d, 1H), 6.88 (m, 1H), 6.65 (s, 1H), 4.27 (t, 2H), 4.05 (m, 2H), 3.75 (s, 2H), 3.24 (m, 2H), 3.21 (t, 2H), 3.13 (q, 2H), 2.18 (m, 2H), 1.24 (t, 3H):

MS (+ve ESI): 588 (M+H)⁺.

$C_{26}H_{31}FN_7O_6P+3.0H_2O$ requires C, 48.7%; H, 5.8%; N, 15.3%; Found C, 48.8%; H, 5.35%; N, 15.15%.

EXAMPLE 40

Preparation of Compound 40 in Table 3—3-{[3-({4-[(5-{2-[(3-fluorophenyl)amino]-2-oxoethyl}-1H-pyrazol-3-yl)amino]quinazolin-7-yl}oxy)propyl]amino}-3-methylbutyl dihydrogen phosphate An analogous reaction to that described in example 1, but starting with di-tert-butyl 3-{[3-({4-[(5-{2-[(3-fluorophenyl)amino]-2-oxoethyl}-1H-pyrazol-3-yl)amino]quinazolin-7-yl}oxy)propyl]amino}-3-methylbutyl phosphate (247 mg, 0.35 mmol) yielded compound 40 in table 3 (235 mg, 100% yield) as a pale yellow dihydrochloride salt:

¹H-NMR (DMSO d₆): 11.98 (s, 1H), 10.76 (s, 1H), 8.94 (s, 1H), 8.83 (d, 1H), 7.65 (d, 1H), 7.48 (d, 1H), 7.37 (m, 3H), 6.89 (t, 1H), 6.75 (s, 1H), 4.35 (t, 2H), 4.00 (q, 2H), 3.85 (s, 2H), 3.11 (m, 2H), 2.26 (m, 2H), 2.05 (t, 2H), 1.35 (s, 6H):

MS (+ve ESI): 601.8 (M+H)⁺.

di-tert-butyl 3-{[3-({4-[(5-{2-[(3-fluorophenyl)amino]-2-oxoethyl}-1H-pyrazol-3-yl)amino]quinazolin-7-yl}oxy)propyl]amino}-3-methylbutyl phosphate used as starting material was obtained as follows:

a) An analogous reaction to that described in example 37a, but starting with 3-amino-3-methylbutan-1-ol (1.15 ml, 11.0 mmol) yielded N-(3-fluorophenyl)-2-{3-[(7-{3-[(3-hydroxy-1,1-dimethylpropyl)amino]propoxy}quinazolin-4-yl)amino]-1H-pyrazol-5-yl}acetamide as a pale yellow solid (310 mg, 27% yield):
$^{1}$H-NMR (DMSO d$_{6}$): 12.31 (m, 1H), 10.40 (m, 1H), 8.50 (m, 2H), 7.62 (d, 1H), 7.35 (m, 2H), 7.11 (m, 2H), 6.89 (t, 1H), 6.56 (m, 1H), 4.18 (t, 2H), 3.71 (s, 2H), 3.52 (t, 2H), 2.65 (t, 2H), 1.86 (m, 2H), 1.52 (t, 2H), 1.04 (s, 6H):
MS (+ve ESI): 522.5 (M+H)$^{+}$.

b) An analogous reaction to that described in example 6c, but starting with N-(3-fluorophenyl)-2-{3-[(7-{3-[(3-hydroxy-1,1-dimethylpropyl)amino]propoxy}quinazolin-4-yl)amino]-1H-pyrazol-5-yl}acetamide (310 mg, 0.59 mmol) yielded di-tert-butyl 3-{[3-({4-[(5-{2-[(3-fluorophenyl)amino]-2-oxoethyl}-1H-pyrazol-3-yl)amino]quinazolin-7-yl}oxy)propyl]amino}-3-methylbutyl phosphate (247 mg, 58% yield) as a pale yellow solid which was used in the next step without further characterisation.

EXAMPLE 41

Preparation of Compound 41 in Table 3—2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl dihydrogen phosphate An analogous reaction to that described in example 1, but starting with di-tert-butyl 2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl phosphate (270 mg, 0.38 mmol) yielded compound 41 in table 3 (248 mg, 96% yield) as a dihydrochloride salt:
$^{1}$H-NMR (DMSO d$_{6}$): 11.98 (s, 1H), 10.77 (s, 1H), 8.96 (s, 1H), 8.84 (d, 1H), 7.65 (d, 1H), 7.46 (d, 1H), 7.32-7.41 (m, 3H), 6.88 (m, 1H), 6.73 (s, 1H), 6.73 (s, 1H), 4.32 (t, 2H), 4.27 (t, 2H), 3.87 (s, 2H), 3.43 (t, 2H), 3.14 (m, 2H), 2.28 (m, 2H), 1.75 (m, 2H), 0.94 (t, 3H):
MS (+ve ESI): 602 (M+H)$^{+}$,
MS (−ve ESI): 600 (M−H)$^{−}$.

di-tert-butyl 2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl phosphate used as starting material was obtained as follows:

a) An analogous reaction to that described in example 37a, but starting with 2-(propylamino)ethanol (0.89 g, 8.6 mmol) yielded N-(3-fluorophenyl)-2-{3-[(7-{3-[(2-hydroxyethyl)(propyl)amino]propoxy}-quinazolin-4-yl)amino]-1H-pyrazol-5-yl}acetamide as a pale yellow solid (480 mg, 32% yield):
$^{1}$H-NMR (DMSO-d$_{6}$): 12.30 (br s, 1H), 10.38 (s, 1H), 10.15 (br s, 1H), 8.50 (s, 2H), 7.60 (d, 1H), 7.34 (m, 2H), 7.15 (br s, 2H), 6.90 (dd, 1H), 6.78 (br s, 1H), 4.30 (br s, 1H), 4.18 (t, 2H), 3.75 (s, 2H), 3.45 (s, 2H), 2.33-2.75 (m, 6H), 1.90 (t, 2H), 1.40 (m, 2H), 0.80 (m, 3H):
MS (+ve ESI): 522 (M+H)$^{+}$,
MS (−ve ESI): 520 (M−H)$^{−}$.

b) An analogous reaction to that described in example 6c, but starting with N-(3-fluorophenyl)-2-{3-[(7-{3-[(2-hydroxyethyl)(propyl)amino]propoxy}-quinazolin-4-yl)amino]-1H-pyrazol-5-yl}acetamide (470 mg, 0.90 mmol) yielded di-tert-butyl 2-[[3-({4-[(5-{2-[(3-fluorophenyl)amino]-2-oxoethyl}-1H-pyrazol-3-yl)amino]-quinazolin-7-yl}oxy)propyl](propyl)amino]ethyl phosphate (271 mg, 42% yield) as a pale yellow solid:
$^{1}$H-NMR (DMSO d$_{6}$): 12.08 (br s, 1H), 10.00 (s, 1H), 9.89 (br s, 1H), 8.53 (s, 1H), 8.42 (d, 1H), 7.59 (d, 1H), 7.34 (m, 2H), 7.17 (m, 2H), 6.84 (m, 1H), 6.56 (br s, 1H), 4.25 (t, 2H), 3.94 (m, 2H), 3.76 (s, 2H), 2.79 (t, 2H), 2.71 (t, 2H), 2.50 (t, 2H), 1.93 (m, 2H), 1.48 (m, 20H), 0.89 (t, 3H):
MS (+ve ESI): 714 (M+H)$^{+}$,
MS (−ve ESI): 712 (M−H)$^{−}$.

EXAMPLE 42

Preparation of Compound 42 in Table 3—{(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl dihydrogen phosphate An analogous reaction to that described in example 1, but starting with di(tert-butyl) {(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl phosphate (280 mg, 0.39 mmol) yielded compound 42 in table 3 (268 mg, 100% yield) as a pale yellow dihydrochloride salt:
$^{1}$H-NMR (DMSO d$_{6}$): 11.96 (s, 1H), 10.75 (s, 1H), 8.94 (s, 1H), 8.82 (d, 1H), 7.65 (d, 1H), 7.43 (d, 1H), 7.28-7.41 (m, 3H), 6.91 (m, 1H), 6.71 (s, 1H), 4.31 (t, 2H), 4.20 (m, 2H), 3.86 (s, 2H), 3.77 (m, 1H), 3.55-3.69 (m, 2H), 3.29 (m, 1H), 3.17 (m, 1H), 2.22-2.37 (m, 2H), 2.17 (m, 1H), 2.04 (m, 1H), 1.90 (m, 1H), 1.79 (m, 1H):
MS (+ve ESI): 600 (M+H)$^{+}$,
MS (−ve ESI): 598 (M−H)$^{−}$.

di(tert-butyl) {(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl phosphate used as starting material was obtained as follows:

a) An analogous reaction to that described in example 37a, but starting with D-prolinol (0.87 g, 8.6 mmol) yielded N-(3-fluorophenyl)-2-f{3-[(7-{3-[(2R)-2-(hydroxymethyl)-pyrrolidin-1-yl]propoxy}-quinazolin-4-yl)amino]-1H-pyrazol-5-yl}acetamide as a pale yellow solid (530 mg, 35% yield):
$^{1}$H-NMR (DMSO-d$_{6}$): 12.33 (br s, 1H), 10.38 (s, 1H), 10.20 (br s, 1H), 8.50 (s, 2H), 7.60 (d, 1H), 7.35 (m, 2H), 7.15 (s, 2H), 6.89 (dd, 1H), 6.75 (br s, 1H), 4.30 (br s, 1H), 4.16 (t, 2H), 3.73 (s, 2H), 3.39 (m, 1H), 3.19 (m, 1H), 3.08 (m, 1H), 2.98 (m, 1H), 2.17 (m, 1H), 1.95 (m, 2H), 1.80 (m, 1H), 1.49-1.73 (m, 4H):
MS (+ve ESI): 520 (M+H)$^{+}$,
MS (−ve ESI): 518 (M−H)$^{−}$.

b) An analogous reaction to that described in example 6c, but starting with N-(3-fluorophenyl)-2-{3-[(7-{3-[(2R)-2-(hydroxymethyl)pyrrolidin-1-yl]propoxy}-quinazolin-4-yl)amino]-1H-pyrazol-5-yl}acetamide (530 mg, 1.02 mmol) yielded di(tert-butyl) {(2R)-1-[3-({4-[(5-{2-[(3-fluorophenyl)amino]-2-oxoethyl}-1H-pyrazol-3-yl)amino]-quinazolin-7-yl}oxy)propyl]pyrrolidin-2-yl}methyl phosphate (280 mg, 39% yield) as a pale yellow solid:
MS (+ve ESI): 712 (M+H)$^{+}$,
MS (−ve ESI): 710 (M−H)$^{−}$.

EXAMPLE 43

Preparation of Compound 43 in Table 3—3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl dihydrogen phosphate An analogous reaction to that described in example 1, but starting with di-tert-butyl 3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl phosphate (45 mg, 0.06 mmol) yielded compound 43 in table 3 (36 mg, 95% yield) as a pale yellow dihydrochloride salt:

$^1$H-NMR (DMSO $d_6$): 10.35 (br s, 1H), 8.78-9.10 (m, 2H), 7.55-7.62 (m, 1H), 7.42-7.50 (m, 2H), 7.28-7.40 (m, 2H), 6.80-6.87 (m, 1H), 6.65-6.79 (br m, 1H), 4.35 (t, 2H), 3.95-4.02 (m, 2H), 3.85 (s, 2H), 3.28 (t, 2H), 3.15-3.25 (m, 4H), 2.25-2.35 (m, 2H), 2.05-2.15 (m, 2H), 1.31 (t, 3H):

MS (+ve ESI): 602 (M+H)$^+$.

di-tert-butyl 3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl phosphate used as starting material was obtained as follows:

a) An analogous reaction to that described in example 37a, but starting with 3-aminopropan-1-ol (247 mg, 3.3 mmol) yielded N-(3-fluorophenyl)-2-{3-[(7-{3-[(3-hydroxypropyl)amino]propoxy}quinazolin-4-yl)amino]-1H-pyrazol-5-yl}acetamide as a pale yellow solid (295 mg, 54% yield):

$^1$H-NMR (DMSO $d_6$): 10.42 (br s, 1H), 8.43-8.54 (m, 2H), 7.58-7.63 (m, 1H), 7.29-7.38 (m, 2H), 7.11-7.18 (m, 2H), 6.84-6.91 (m, 1H), 6.56-6.78 (br m, 1H), 4.18 (t, 2H), 3.72 (s, 2H), 3.45 (t, 2H), 2.67 (t, 2H), 2.58 (t, 2H), 1.84-1.95 (m, 2H), 1.51-1.61 (m, 2H):

MS (+ve ESI): 494 (M+H)$^+$.

b) Tri(acetoxy)borohydride (750 mg, 1.48 mmol) was added to a solution of N-(3-fluorophenyl)-2-{3-[(7-{3-[(3-hydroxypropyl)amino]propoxy}quinazolin-4-yl)amino]-1H-pyrazol-5-yl}acetamide (290 mg, 0.59 mmol) and acetaldehyde (39 mg, 0.88 mmol) in dimethylformamide (3 ml) at ambient temperature and the reaction stirred for 2 hours. The reaction mixture was filtered, diluted with dichloromethane (10 ml) and purified by flash chromatography on silica gel, eluting with 3-12% methanol: dichloromethane. Evaporation of the fractions in vacuo yielded 2-{3-[(7-{3-[ethyl(3-hydroxypropyl)amino]propoxy}-quinazolin-4-yl)amino]-1H-pyrazol-5-yl}-N-(3-fluorophenyl)acetamide (105 mg, 34% yield) as a white solid:

$^1$H-NMR (DMSO dc): 10.41 (br s, 1H), 10.13-10.30 (br s, 1H), 8.43-8.55 (m, 2H), 7.57-7.65 (m, 1H), 7.28-7.39 (m, 2H), 7.09-7.21 (m, 2H), 6.83-6.92 (m, 1H), 6.65-6.81 (m, 1H), 4.15 (t, 2H), 3.73 (s, 2H), 3.41 (t, 2H), 2.41-2.58 (m, 6H under DMSO), 1.82-1.93 (m, 2H), 1.48-1.58 (m, 2H), 0.94 (t, 3H):

MS (+ve ESI): 522 (M+H)$^+$.

c) An analogous reaction to that described in example 6c, but starting with 2-{3-[(7-{3-[ethyl(3-hydroxypropyl)amino]propoxy}quinazolin-4-yl)amino]-1H-pyrazol-5-yl}-N-(3-fluorophenyl)acetamide (90 mg, 0.17 mmol) yielded di-tert-butyl 3-[[3-({4-[(5-{2-[(3-fluorophenyl)amino]-2-oxoethyl}-1H-pyrazol-3-yl)amino]-quinazolin-7-yl}oxy)propyl](ethyl)amino]propyl phosphate (45 mg, 37% yield) as a pale yellow solid:

MS (+ve ESI): 714 (M+H)$^+$,
MS (−ve ESI): 712 (M−H)$^−$.

EXAMPLE 44

Preparation of Compound 44 in Table 3—2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl dihydrogen phosphate Di-tert-butyl 2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl phosphate (200 mg, 0.3 mmol) was solubilised in dioxane (7 ml) and treated with a mixture of dioxane/hydrochloric acid (4.0 N, 0.5 ml) at 20° C. overnight. A light yellow solid was recovered by filtration and dried in vacuo (55° C., 12 h) to yield 2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl dihydrogen phosphate (200 mg, 85% yield) as a pale yellow solid:

$^1$H-NMR (DMSO $d_6$, CH$_3$COOD): 8.95 (s, 1H), 8.82 (d, 1H), 7.65 (d, 1H), 7.46 (d, 1H), 7.37 (m, 3H), 6.88 (m, 1H), 6.78 (s, 1H), 4.33 (m, 2H), 4.28 (m, 2H), 3.86 (s, 2H), 3.76 (m, 2H), 3.53 (m, 2H), 3.45 (m, 4H), 3.34 (s, 3H), 2.30 (m, 2H):

MS (+ve ESI): 618 (M+H)$^+$.

di-tert-butyl 2-[[3-({4-[(5-{2-[(3-fluorophenyl)amino]-2-oxoethyl}-1H-pyrazol-3-yl)amino]quinazolin-7-yl}oxy)propyl](2-methoxyethyl)amino]ethyl phosphate used as starting material, was obtained as follows:

a) 2-((2-methoxyethyl)amino)ethanol (750 mg, 6.29 mmol) was added to a solution of 2-(3-{[7-(3-chloropropoxy)quinazolin-4-yl]amino}-1H-pyrazol-5-yl)-N-(3-fluorophenyl)acetamide (960 mg, 2.11 mmol) and potassium iodide (700 mg, 4.22 mmol) in 1-methyl-2-pyrrolidinone (8 ml). The mixture was stirred at 80° C. for 1.5 hours, cooled, added onto a silica gel column, and purified by chromatography eluting successively with dichloromethane, dichloromethane: methanol 96:4 to 92:8 to give N-(3-fluorophenyl)-2-{3[(7-{3-[(2-hydroxyethyl)(2-methoxyethyl)amino]propoxy}quinazolin-4-yl)amino]-1H-pyrazol-5-yl}acetamide (600 mg, 53% yield) as an off white solid.

$^1$H-NMR (DMSO $d_6$, TFA): 9.0 (s, 1H), 8.83 (d, 1H), 7.65 (d, 1H), 7.48 (d, 1H), 7.36 (m, 2H), 7.28 (s, 1H), 6.88 (m, 1H), 6.80 (s, 1H), 4.32 (m, 2H), 3.86 (s, 2H), 3.80 (m, 2H), 3.73 (m, 2H), 3.48 (m, 4H), 3.37 (m, 2H), 3.34 (s, 3H), 2.28 (m, 2H)

MS (+ve ESI): 538 (M+H)$^+$.

b) Di-tert-butyl-diethylphosphoramidite (0.56 ml, 2 mmol) was slowly added to a mixture of N-(3-fluorophenyl)-2-{3-[(7-{3-[(2-hydroxyethyl)(2-methoxyethyl)amino]propoxy}quinazolin-4-yl)amino]-1H-pyrazol-5-yl}acetamide (540 mg, 1 mmol) and tetrazole (200 mg, 3 mmol) in dimethylformamide (5 ml) at 20° C. for 2 hours. The mixture was then cooled to 0° C. and hydrogen peroxide (9.0 N, 0.33 ml, 2.93 mmol) was slowly added and stirring at ambient temperature was continued for 12 hours. Sodium metabisulphite (1.14 g, 6 mmol) in solution in water (12 ml) was then added to the reaction mixture at 0° C., which was slowly allowed to warm to ambient temperature. The solvents were then evaporated and the residue was purified by silica gel chromatography, eluting with dichloromethane: methanolic ammonia (3.0 N) 96:4 to 94:6 to yield di-tert-butyl 2-[[3-({4-[(5-{2-[(3-fluorophenyl)amino]-2-oxoethyl}1H-pyrazol-3-yl)amino]quinazolin-7-yl}oxy)propyl](2-methoxyethyl)amino]ethyl phosphate (220 mg, 30% yield):

$^1$H-NMR (DMSO $d_6$, TFA): 8.98 (s, 1H), 8.81 (d, 1H), 7.63 (d, 1H), 7.48 (d, 1H), 7.36 (m, 2H), 7.27 (s, 1H), 6.90 (t, 1H), 6.77 (s, 1H), 4.30 (m, 2H), 4.26 (m, 2H), 3.84 (s, 2H), 3.72 (m, 2H), 3.55 (m, 2H), 3.48 (m, 2H), 3.42 (m, 2H), 3.34 (s, 3H), 2.26 (m, 2H), 1.44 (s, 18H):

MS (+ve ESI): 730 (M+H)+.

EXAMPLE 45

Preparation of Compound 45 in Table 4—2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl dihydrogen phosphate An analogous reaction to that described in example 1, but starting with di-tert-butyl 2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl phosphate (550 mg, 0.74 mmol) yielded compound 45 in table 4 (504 mg, 96% yield) as the dihydrochloride salt:

$^1$H-NMR (DMSO d$_6$): 11.95 (s, 1H), 10.34 (s, 1H), 8.90 (s, 1H), 8.83 (d, 1H), 7.68 (m, 1H), 7.45 (m, 2H), 7.22 (m, 2H), 6.72 (s, 1H), 4.23 (m, 4H), 3.91 (s, 2H), 3.40 (m, 2H), 3.20 (m, 2H), 3.08 (m, 2H), 1.88 (m, 4H), 1.71 (m, 2H), 0.90 (t, 3H):

MS (+ve ESI): 634 (M+H)+,
MS (−ve ESI): 632 (M−H)−.

di-tert-butyl 2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl phosphate used as starting material was obtained as follows:

a) 1,4-Dihydroxybutane (33.0 ml, 366 mmol) was added over 10 minutes to a stirred suspension of sodium hydride (14.6 g of a 60% dispersion in oil, 366 mmol) in dimethylacetamide (200 ml) at 0° C. and the reaction stirred for 15 minutes before being heated to 60° C. A solution of 7-fluoroquinazolin-4(3H)-one (10.0 g, 61.0 mmol) in dimethylacetamide (60 ml) was added over 5 minutes and the reaction stirred at 110° C. for a further 5 hours. The reaction was cooled, poured onto ice (500 g) and treated with brine (500 ml) and 5.0 N hydrochloric acid (until pH<6). The resultant solid was collected by suction filtration, washed with water and diethyl ether and then taken up in dimethylacetamide (100 ml). The reaction was filtered and the filtrate evaporated in vacuo to yield 7-(4-hydroxy-butoxy)quinazolin-4(3H)-one (5.88 g, 41% yield) as a white solid after drying in vacuo:

$^1$H-NMR (DMSO d$_6$): 8.15 (s, 1H), 8.10 (m, 1H), 7.18 (m, 2H), 4.22 (m, 2H), 3.58 (m, 2H), 1.90 (m, 2H), 1.70 (m, 2H):

MS (+ve ESI): 235 (M+H)+,
MS (−ve ESI): 233 (M−H)−.

b) Dimethylformamide (0.5 ml) was added to a stirred suspension of 7-(4-hydroxy-butoxy)quinazolin-4(3H)-one (4.86 g, 20.0 mmol) in thionyl chloride (50 ml) and the reaction heated at reflux for 1 hour. The reaction was cooled, the excess thionyl chloride was evaporated in vacuo and the residue was azeotroped with toluene (2×50 ml) before being taken up in dimethylacetamide (50 ml). 5-amino-1H-pyrazole-3-acetic acid (2.82 g, 20 mmol) and 4.0 N hydrochloric acid in dioxan (5.0 ml, 20 mmol) were added and the reaction was stirred at 90° C. for 40 minutes. The reaction was cooled to ambient temperature, poured into ice-water (500 ml) and acidified to pH>12 with 40% aqueous sodium hydroxide solution. The reaction was filtered, the filtrate was acidified to pH<4.8 and the solid which precipitated was collected by suction filtration to yield-(3-{[7-(4-chlorobutoxy)quinazolin-4-yl]amino}-1H-pyrazol-5-yl)acetic acid (7.07 g, 91% yield) as a pale orange solid:

$^1$H-NMR (DMSO d$_6$): 12.45 (br s, 2H), 8.57 (s, 1H), 8.50 (d, 1H), 7.17 (m, 2H), 6.60 (s, 1H), 4.18 (m, 2H), 3.75 (m, 2H), 3.65 (s, 2H), 1.90 (m, 4H):

MS (+ve ESI): 376 (M+H)+,
MS (−ve ESI): 374 (M−H)−.

c) Phosphorus oxychloride (1.8 ml, 19.5 mmol) was added to a stirred suspension of 2,3-difluoroaniline (2.88 g, 22.3 mmol), (3-{[7-(4-chlorobutoxy)quinazolin-4-yl]amino}-1H-pyrazol-5-yl)acetic acid (6.97 g, 18.6 mmol) and pyridine (100 ml) at 0° C. The reaction was stirred for 2.5 hours at 0° C., additional phosphorus oxychloride (0.3 ml) was added and the reaction allowed to warm to ambient temperature over 18 hours. Ethyl acetate (200 ml) and diethyl ether (100 ml) were added, the reaction was stirred and the sticky solid collected by filtration before being suspended in water (300 ml). Dilute aqueous ammonia was added until the pH was >7 and the resultant solid was collected by suction filtration. Washing of the resultant solid with water and then acetonitrile, followed by prolonged drying in vacuo, yielded 2-(3-{[7-(4-chlorobutoxy)quinazolin-4-yl]amino}-1H-pyrazol-5-yl)-N-(2,3-difluorophenyl)acetamide (7.6 g, 84% yield) as a pale brown solid:

$^1$H-NMR (DMSO d$_6$): 10.20 (s, 1H), 8.63 (s, 1H), 8.58 (d, 1H), 7.69 (m, 1H), 7.23 (m, 1H), 7.15 (m, 3H), 6.68 (s, 1H), 4.14 (m, 2H), 3.81 (s, 2H), 3.70 (m, 2H), 1.88 (m, 4H):

MS (+ve ESI): 487 (M+H)+
MS (−ve ESI): 485 (M−H)−.

d) An analogous reaction to that described in example 28f, but starting with 2-(propylamino)ethanol (765 mg, 7.40 mmol) and 2-(3-{[7-(4-chlorobutoxy)quinazolin-4-yl]amino}-1H-pyrazol-5-yl)-N-(2,3-difluorophenyl)acetamide (1.20 g, 2.47 mmol) yielded N-(2,3-difluorophenyl)-2-{3-[(7-{4-[propyl(2-hydroxyethyl)amino]butoxy}-quinazolin-4-yl)amino]-1H-pyrazol-5-yl}acetamide as a brown solid (625 mg, 46% yield):

$^1$H-NMR (DMSO d$_6$): 10.3 (br s, 1H), 8.49 (s, 1H), 8.45 (m, 1H), 7.70 (m, 1H), 7.15 (m, 3H), 7.1 (s, 1H), 6.58 (br, s, 1H), 4.1 (m, 2H), 3.80 (s, 2H), 3.42 (m, 2H), 2.45 (m, 4H), 2.33 (m, 2H), 1.77 (m, 2H), 1.55 (m, 2H), 1.35 (m, 2H), 0.81 (t, 3H):

MS (+ve ESI): 554 (M+H)+
MS (−ve ESI): 552 (M−H)−.

e) An analogous reaction to that described in example 6c, but starting with N-(2,3-difluorophenyl)-2-{3-[(7-{4-[(2-hydroxyethyl)(propyl)amino]butoxy}-quinazolin-4-yl)amino]-1H-pyrazol-5-yl}acetamide (540 mg, 0.98 mmol) yielded di-tert-butyl 2-[[4-({4-[(5-{2-[(2,3-difluorophenyl)amino]-2-oxoethyl}-1H-pyrazol-3-yl)amino]-quinazolin-7-yl}oxy)butyl](propyl)amino]ethyl phosphate (566 mg, 78% yield) as a pale yellow solid:

$^1$H-NMR (DMSO d$_6$): 12.3 (s, 1H), 10.18 (m, 2H), 8.51 (m, 2H), 7.72 (m, 1H), 7.15 (m, 4H), 6.77 (s, 1H), 4.15 (m, 2H), 3.85 (m, 4H), 2.65 (m, 2H), 2.40 (m, 2H), 1.78 (m, 2H), 1.56 (m, 2H), 1.4 (m, 2H), 1.39 (s, 18H), 0.85 (t, 3H):

MS (+ve ESI): 746 (M+H)+
MS (−ve ESI): 744 (M−H)−.

EXAMPLE 46

Preparation of Compound 46 in Table 4—2-[[4-({4-[5-{2-[(2,3-difluorophenyl)amino]-2-oxoethyl}-1H-pyrazol-3-yl)amino]-quinazolin-7-yl}oxy)butyl](ethyl)amino]ethyl dihydrogen phosphate An analogous reaction to that described in example 1, but starting with di(tert-butyl) 2-[[4-({4-[(5-{2-[(2,3-difluorophenyl)amino]-2-oxoethyl}-1H-pyrazol-3-yl)amino]- quinazolin-7-yl}oxy)butyl](ethyl)amino]ethyl phosphate (386 mg, 0.53 mmol) yielded compound 46 in table 4 (340 mg, 93% yield) as a white dihydrochloride salt:
$^1$H-NMR (DMSO d$_6$): 11.97 (s, 1H), 10.35 (s, 1H), 8.92 (s, 1H), 8.85 (d, 1H), 7.67 (m, 1H), 7.45 (m, 2H), 7.18 (m, 2H), 6.75 (s, 1H), 4.23 (m, 4H), 3.90 (s, 2H), 3.39 (m, 2H), 3.20 (m, 4H), 1.87 (m, 4H), 1.25 (t, 3H):
MS (+ve ESI): 619 (M+H)+
MS (−ve ESI): 617 (M−H)−.

di(tert-butyl) 2-[[4-({4-[(5-{2-[(2,3-difluorophenyl)amino]-2-oxoethyl}-1H-pyrazol-3-yl)amino]-quinazolin-7-yl}oxy)butyl](ethyl)amino]ethyl phosphate used as starting material was obtained as follows:
a) An analogous reaction to that described in example 45d, but starting with 2-(ethylamino)ethanol (468 mg, 5.25 mmol) yielded N-(2,3-difluorophenyl)-2-{3-[(7-{4-[ethyl(2-hydroxyethyl)amino]butoxy}-quinazolin-4-yl)amino]-1H-pyrazol-5-yl}acetamide as an off-white solid (443 mg, 47% yield):
$^1$H-NMR (DMSO d$_6$): 10.25 (br s, 1H), 8.45 (m, 2H), 7.70 (m, 1H), 7.12 (m, 4H), 6.58 (br s, 1H), 4.25 (br s, 1H), 4.13 (m, 2H), 3.80 (s, 2H), 3.42 (m, 2H), 1.76 (m, 2H), 1.55 (m, 2H), 0.95 (t, 3H):
MS (+ve ESI): 540 (M+H)+
MS (−ve ESI): 538 (M−H)−.

b) An analogous reaction to that described in example 6c, but starting with N-(2,3-difluorophenyl)-2-{3-[(7-{4-[ethyl(2-hydroxyethyl)amino]butoxy}-quinazolin-4-yl)amino]-1H-pyrazol-5-yl}acetamide (385 mg, 0.71 mmol) yielded di(tert-butyl) 2-[[4-({4-[(5-{2-[(2,3-difluorophenyl)amino]-2-oxoethyl}-1H-pyrazol-3-yl)amino]-quinazolin-7-yl}oxy)butyl](ethyl)amino]ethyl phosphate (393 mg, 75% yield) as a pale yellow solid:
$^1$H-NMR (DMSO d$_6$): 12.30 (s, 1H), 10.18 (br s, 1H), 8.50 (m, 2H), 7.71 (m, 1H), 7.15 (m, 4H), 6.78 (s, 1H), 4.3 (m, 2H), 3.85 (m, 4H), 2.68 (m, 2H), 1.78 (m, 2H), 1.58 (m, 2H), 1.40 (s, 18H), 0.97 (t, 3H):
MS (+ve ESI): 732 (M+H)+
MS (−ve ESI): 730 (M−H)−.

EXAMPLE 47

Preparation of Compound 47 in Table 4—{(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate An analogous reaction to that described in example 1, but starting with di(tert-butyl) {(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl phosphate (464 mg, 0.62 mmol) yielded compound 47 in table 4 (400 mg, 91% yield) as an off-white dihydrochloride salt:
$^1$H-NMR (DMSO d$_6$): 11.95 (s, 1H), 10.35 (s, 1H), 8.92 (s, 1H), 8.83 (d, 1H), 7.68 (m, 1H), 7.45 (m, 2H), 7.18 (m, 2H), 6.71 (s, 1H), 4.2 (m, 4H), 3.92 (s, 2H), 3.72 (m, 1H), 3.60 (m, 1H), 3.45 (m, 1H), 3.15 (m, 2H), 2.15 (m, 1H), 1.7-2.1 (m, 7H):
MS (+ve ESI): 631 (M+H)+
MS (−ve ESI): 630 (M−H)−.

di(tert-butyl) {(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl phosphate used as starting material was obtained as follows:
a) An analogous reaction to that described in example 45d, but starting with D-prolinol (530 mg, 5.25 mmol) yielded N-(2,3-difluorophenyl)-2-{3-[(7-{4-[(2R)-2-(hydroxymethyl)pyrrolidin-1-yl]butoxy}-quinazolin-4-yl)amino]-1H-pyrazol-5-yl}acetamide as an off-white solid (516 mg, 54% yield):
$^1$H-NMR (DMSO d$_6$): 10.25 (br s, 1H), 8.45 (m, 2H), 7.7 (m, 1H), 7.15 (m, 4H), 6.6 (br s, 1H), 4.30 (br s, 1H), 4.21 (m, 2H), 3.80 (s, 2H), 3.40 (m, 1H), 3.20 (m, 1H), 3.05 (m, 1H), 2.85 (m, 1H), 2.40 (m, 1H), 2.30 (m, 1H), 2.10 (m, 1H), 1.77 (m, 3H), 1.6 (m, 5H):
MS (+ve ESI): 552 (M+H)+.
MS (−ve ESI): 550 (M−H)−.

b) An analogous reaction to that described in example 6c, but starting with N-(2,3-difluorophenyl)-2-{3-[(7-{4-[(2R)-2-(hydroxymethyl)pyrrolidin-1-yl]butoxy}-quinazolin-4-yl)amino]-1H-pyrazol-5-yl}acetamide (450 mg, 0.82 mmol) yielded di(tert-butyl) {(2R)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl phosphate (470 mg, 77% yield) as a pale yellow solid:
$^1$H-NMR (DMSO d$_6$): 12.3 (s, 1H), 10.18 (s, 1H), 8.50 (m, 2H), 7.71 (m, 1H), 7.18 (m, 4H), 6.77 (s, 1H), 4.15 (m, 2H), 3.80 (m, 3H), 3.62 (m, 1H), 3.05 (m, 1H), 2.80 (m, 1H), 2.65 (m, 1H), 2.37 (m, 1H), 2.18 (m, 1H), 1.80 (m, 3H), 1.62 (m, 5H), 1.38 (s, 18H):
MS (+ve ESI): 744 (M+H)+.
MS (−ve ESI): 742 (M−H)−.

EXAMPLE 48

Preparation of Compound 48 in Table 4—2-[[4-({4-[(5-{2-[(2,3-difluorophenyl)amino]-2-oxoethyl-1H-pyrazol-3-yl)amino]quinazolin-7-yl}oxy)butyl](methyl)amino]ethyl dihydrogen-phosphate An analogous reaction to that described in example 1, but starting with di-tert-butyl 2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl phosphate (250 mg, 0.35 mmol) yielded compound 48 in table 4 (263 mg, 100% yield) as an off-white dihydrochloride salt:
$^1$H-NMR (DMSO d$_6$): 11.95 (s, 1H), 10.35 (s, 1H), 8.92 (s, 1H), 8.83 (d, 1H), 7.69 (m, 1H), 7.45 (m, 2H), 7.29 (m, 2H), 6.75 (s, 1H), 4.22 (m, 4H), 3.81 (s, 2H), 3.39 (m, 2H), 3.20 (m, 2H), 2.80 (s, 3H), 1.85 (m, 4H):
MS (+ve ESI): 605 (M+H)+
MS (−ve ESI): 603 (M−H)−.

di-tert-butyl 2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl phosphate used as starting material was obtained as follows:
a) An analogous reaction to that described in example 45d, but starting with 2-(methylamino)ethanol (394 mg, 5.25 mmol) yielded)-(2,3-difluorophenyl)-2-{3-[(7-{4-[(2-hydroxyethyl)(methyl)amino]butoxy}quinazolin-4-yl)amino]-1H-pyrazol-5-yl}acetamide as an off-white solid (536 mg, 58% yield):
$^1$H-NMR (DMSO d$_6$): 10.25 (br s, 1H), 8.45 (m, 2H), 7.71 (m, 1H), 7.15 (m, 4H), 6.58 (br s, 1H), 4.3 (br s, 1H), 4.12 (m, 2H), 3.80 (s, 2H), 3.45 (m, 2H), 2.39 (m, 4H), 2.15 (s, 3H), 1.79 (m, 2H), 1.58 (m, 2H):
MS (+ve ESI): 526 (M+H)+
MS (−ve ESI): 524 (M−H)−.

b) An analogous reaction to that described in example 6c, but starting with N-(2,3-difluorophenyl)-2-{3-[(7-{4-[(2-hydroxyethyl)(methyl)amino]butoxy}quinazolin-4-yl)

amino]-1H-pyrazol-5-yl}acetamide (460 mg, 0.88 mmol) yielded di-tert-butyl 2-[[4-({4-[(5-{2-[(2,3-difluorophenyl)amino]-2-oxoethyl}-1H-pyrazol-3-yl)amino]quinazolin-7-yl}oxy)butyl](methyl)amino]ethyl phosphate (368 mg, 59% yield) as a pale yellow solid:

$^1$H-NMR (DMSO d$_6$): 12.30 (s, 1H), 10.17 (m, 2H), 8.50 (m, 2H), 7.70 (m, 1H), 7.18 (m, 4H), 6.77 (s, 1H), 4.15 (m, 2H), 3.9 (m, 2H), 3.85 (s, 2H), 2.60 (m, 2H), 2.43 (m, 2H), 2.20 (s, 3H), 1.8 (m, 2H), 1.58 (m, 2H), 1.40 (s, 18H):

MS (+ve ESI): 718 (M+H)$^+$

MS (−ve ESI): 716 (M−H)$^−$.

EXAMPLE 49

Preparation of Compound 49 in Table 4—{(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl dihydrogen phosphate An analogous reaction to that described in example 1, but starting with di(tert-butyl) {(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl phosphate (386 mg, 0.53 mmol) yielded compound 49 in table 4 (340 mg, 93% yield) as an off-white dihydrochloride salt:

$^1$H-NMR (DMSO d$_6$): 11.7 (br s, 1H), 10.30 (s, 1H), 8.87 (s, 1H), 8.75 (d, 1H), 7.68 (m, 1H), 7.40 (m, 2H), 7.19 (m, 2H), 6.71 (s, 1H), 4.20 (m, 2H), 4.18 (m, 2H), 3.90 (s, 2H), 3.7 (m, 1H), 3.58 (m, 1H), 3.42 (m, 1H), 3.1 (m, 2H), 2.15 (m, 1H), 1.75-2.1 (m, 7H):

MS (+ve ESI): 630 (M+H)$^+$

MS (−ve ESI): 632 (M−H)$^−$.

di(tert-butyl) {(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl phosphate used as starting material was obtained as follows:

a) An analogous reaction to that described in example 45d, but starting with L-prolinol (530 mg, 5.25 mmol) yielded N-(2,3-difluorophenyl)-2-{3-[(7-{4-[(2S)-2-(hydroxymethyl)pyrrolidin-1-yl]butoxy}-quinazolin-4-yl)amino]-1H-pyrazol-5-yl}acetamide as an off-white solid (550 mg, 57% yield):

$^1$H-NMR (DMSO d$_6$): 12.38 (br s, 1H), 10.20 (br s, 1H), 8.47 (m, 2H), 7.70 (m, 1H), 7.15 (m, 4H), 6.62 (br s, 1H), 4.28 (br s, 1H), 4.15 (m, 2H), 3.81 (s, 2H), 3.40 (m, 1H), 3.20 (m, 1H), 3.02 (m, 1H), 2.81 (m, 1H), 2.38 (m, 1H), 2.30 (m, 1H), 2.10 (m, 1E1), 1.78 (m, 3H), 1.58 (m, 5H):

MS (+ve ESI): 552 (M+H)$^+$

MS (−ve ESI): 550 (M−H)$^−$.

b) An analogous reaction to that described in example 6c, but starting with N-(2,3-difluorophenyl)-2-{3-[(7-{4-[(2S)-2-(hydroxymethyl)pyrrolidin-1-yl]butoxy}-quinazolin-4-yl)amino]-1H-pyrazol-5-yl}acetamide (340 mg, 0.62 mmol) yielded di(tert-butyl) {(2S)-1-[4-({4-[(5-{2-[(2,3-difluorophenyl)amino]-2-oxoethyl}-1H-pyrazol-3-yl)amino]-quinazolin-7-yl}oxy)butyl]pyrrolidin-2-yl}methyl phosphate (328 mg, 71% yield) as a pale yellow solid:

$^1$H-NMR (DMSO d$_6$): 12.30 (br s, 1H), 10.15 (s, 2H), 8.48 (m, 2H), 7.68 (m, 1H), 7.15 (m, 4H), 6.75 (br s, 1H), 4.12 (m, 2H), 3.80 (m, 2H), 3.61 (m, 1H), 3.05 (m, 1H), 2.80 (m, 1H), 2.62 (m, 1H), 2.35 (m, 1H), 2.15 (m, 1H), 1.81 (m, 3H), 1.60 (m, 5H), 1.38 (s, 18H):

MS (+ve ESI): 744 (M+H)$^+$

MS (−ve ESI): 742 (M−H)$^−$.

EXAMPLE 50

Preparation of Compound 50 in Table 5—2-{ethyl[3-({6-fluoro-4-[(5-{2-[(3-fluorophenyl)amino]-2-oxoethyl}-1H-pyrazol-3-yl)amino]quinazolin-7-yl]oxy)propyl]amino}ethyl dihydrogen phosphate An analogous reaction to that described in example 1, but starting with di-tert-butyl 2-{ethyl[3-({6-fluoro-4-[(5-{2-[(3-fluorophenyl)amino]-2-oxoethyl}-1H-pyrazol-3-yl)amino]quinazolin-7-yl}oxy)propyl]amino}ethyl phosphate (275 mg, 0.38 mmol) yielded compound 50 in table 5 (260 mg, 100% yield) as an off-white dihydrochloride salt:

$^1$H-NMR (DMSO d$_6$): 12.0 (br s, 1H), 10.87 (s, 1H), 8.96 (s, 1H), 8.87 (d, 1H), 7.65 (m, 2H), 7.38 (m, 2H), 6.89 (m, 2H), 6.77 (s, 1H), 4.42 (t, 2H), 4.26 (m, 2H), 3.86 (s, 2H), 3.44 (t, 2H), 3.35 (m, 2H), 3.28 (m, 2H), 2.33 (m, 2H), 1.31 (t, 3H):

MS (+ve ESI): 606 (M+H)$^+$.

di-tert-butyl 2-{ethyl[3-({6-fluoro-4-[(5-{2-[(3-fluorophenyl)amino]-2-oxoethyl}-1H-pyrazol-3-yl)amino]quinazolin-7-yl}oxy)propyl]amino}ethyl phosphate phosphate used as starting material was obtained as follows:

a) Benzyl alcohol (4.27 g, 39.5 mmol) was added dropwise to a stirred suspension of sodium hydride (1.6 g of a 60% dispersion in mineral oil, 40.0 mmol) in dimethylformamide (50 ml) at 0° C. The reaction was stirred at 0° C. for 1 hour before addition of 6,7-difluoroquinazolin-4(1H)-one (3.60 g, 19.8 mmol) whereupon the reaction was heated to 60° C. for 2 hours. The reaction was cooled to ambient temperature, poured into water (200 ml) and the resultant solid collected by suction filtration. Drying of the solid in vacuo yielded 7-(benzyloxy)-6-fluoroquinazolin-4(1H)-one (4.45 g, 83% yield) as a pale brown solid:

$^1$H-NMR (DMSO d$_6$): 12.24 (br s, 1H), 8.05 (s, 1H), 7.80 (d, 1H), 7.52 (m, 2H), 7.44 (m, 3H), 7.38 (t, 1H), 5.35 (s, 2H).

b) 7-(Benzyloxy)-6-fluoroquinazolin-4(1H)-one (2.00 g, 7.41 mmol) was taken up in phosphorus oxychloride (20 ml) and the reaction heated at reflux for 90 minutes. The reaction was cooled, azeotroped with toluene (2×50 ml) and taken up in dichloromethane (5 ml) The organic phase was washed with saturated aqueous sodium hydrogen carbonate solution and thend ried over magnesium sulphate. Solvent evaporation in vacuo followed by drying of the solid in vacuo yielded 7-(benzyloxy)-4-chloro-6-fluoroquinazoline (1.50 g, 71% yield) as a pale yellow solid:

$^1$H-NMR (CDCl$_3$): 8.93 (s, 1H), 7.89 (d, 1H), 7.51 (m, 3H), 7.35-7.46 (m, 3H), 5.32 (s, 2H).

c) A mixture of 7-(benzyloxy)-4-chloro-6-fluoroquinazoline (1.20 g, 4.16 mmol) and 2-(3-amino-1H-pyrazol-5-yl)-N-(3-fluorophenyl)acetamide (0.97 g, 4.15 mmol) were heated at reflux in 2-propanol (20 ml) for 2 hours. The reaction was cooled to ambient temperature, diluted with diethyl ether and the resultant solid collected by suction filtration. Prolonged drying in vacuo yielded 2-(3-{[7-(benzyloxy)-6-fluoroquinazolin-4-yl]amino}-1H-pyrazol-5-yl)-N-(3-fluorophenyl)acetamide (2/.00 g, 92% yield) as a pale yellow solid:

$^1$H-NMR (DMSO d$_6$): 11.72 (br s, 1H), 10.71 (s, 1H), 8.90 (s, 1H), 8.82 (d, 1H), 7.65 (m, 2H), 7.55 (m, 2H), 7.32-7.50 (m, 5H), 6.89 (m, 1H), 6.76 (s, 1H), 5.42 (s, 2H), 3.84 (s, 2H):

MS (+ve ESI): 487 (M+H)$^+$.

d) A solution of 2-(3-{[7-(benzyloxy)-6-fluoroquinazolin-4-yl]amino}-1H-pyrazol-5-yl)-N-(3-fluorophenyl)acetamide (hydrochloride salt) (1.95 g, 3.74 mmol) in trifluoroacetic acid (20 ml) was heated at reflux for 7 hours. The reaction was cooled to ambient temperature, and the trifluoroacetic acid removed in vacuo. Trituration of the residue with diethyl ether (2×25 ml) yielded 2-{3-[(6-fluoro-7-hydroxyquinazolin-4-yl)amino]-1H-pyrazol-5-yl}-N-(3-fluorophenyl)acetamide (2.00 g, 100% yield) as a pale yellow solid:

MS (+ve ESI): 397 (M+H)+.

e) Caesium carbonate (2.67 g, 8.2 mmol) was added to a stirred solution of 2-{3-[(6-fluoro-7-hydroxyquinazolin-4-yl)amino]-1H-pyrazol-5-yl}-N-(3-fluorophenyl)acetamide (2.09 g, 4.10 mmol) and 3-bromo-1-chloropropane (0.44 ml, 4.5 mmol) in dimethylformamide (20 ml) and the reaction heated at 70° C. for 1 hour. The reaction was cooled to ambient temperature, poured into water (150 ml) and the resultant solid was collected by suction filtration. Purification by flash chromatography on silica gel, eluting with 3-8% methanol: dichloromethane gave 2-(3-{[7-(3-chloropropoxy)-6-fluoroquinazolin-4-yl]amino}-1H-pyrazol-5-yl)-N-(3-fluorophenyl)acetamide (1.10 g, 57% yield) as a pale yellow solid, following solvent evaporation in vacuo:

MS (+ve ESI): 473 (M+H)+.

f) An analogous reaction to that described in example 45d, but starting with 2-(ethylamino)ethanol (282 mg, 3.17 mmol) and 2-(3-{[7-(3-chloropropoxy)-6-fluoroquinazolin-4-yl]amino}-1H-pyrazol-5-yl)-N-(3-fluorophenyl)acetamide (500 mg, 1.06 mmol) yielded 2-{3-[(7-{3-[ethyl(2-hydroxyethyl)amino]propoxy}-6-fluoroquinazolin-4-yl)amino]-1H-pyrazol-5-yl}-N-(3-fluorophenyl)acetamide (408 mg, 73% yield) as an off-white solid:

$^1$H-NMR (DMSO $d_6$): 12.40 (s, 1H), 10.40 (s, 1H), 10.15 (s, 1H), 8.53 (s, 1H), 8.50 (br s, 1H), 7.62 (d, 1H), 7.35 (m, 3H), 6.89 (m, 1H), 6.78 (br s, 1H), 4.28 (m, 3H), 3.75 (br s, 2H), 3.45 (m, 2H), 2.62 (t, 2H), 2.50 (m, 4H under DMSO), 1.91 (m, 2H), 0.98 (t, 3H):

MS (+ve ESI): 526 (M+H)+.

g) An analogous reaction to that described in example 6c, but starting with 2-{3-[(7-{3-[ethyl(2-hydroxyethyl)amino]propoxy}-6-fluoroquinazolin-4-yl)amino]-1H-pyrazol-5-yl}-N-(3-fluorophenyl)acetamide (266 mg, 0.51 mmol) yielded di-tert-butyl 2-{ethyl[3-({6-fluoro-4-[(5-{2-[(3-fluorophenyl)amino]-2-oxoethyl}-1H-pyrazol-3-yl)amino]quinazolin-7-yl}oxy)propyl]amino}ethyl phosphate (288 mg, 79% yield) as a pale yellow solid:

$^1$H-NMR (CDCl$_3$): 12.70 (br s, 1H), 9.90 (br s, 1H), 9.40 (s, 1H), 8.60 (s, 1H), 7.98 (d, 1H), 7.56 (d, 1H), 7.15-7.30 (m, 3H), 6.76 (m, 1H), 6.24 (br s, 1H), 4.14 (t, 2H), 4.03 (q, 2H), 3.83 (s, 2H), 2.79 (t, 2H), 2.70 (t, 2H), 2.61 (m, 2H), 1.95 (m, 2H), 1.48 (s, 18H), 1.05 (t, 3H):

MS (+ve ESI: 718 (M+H)+.

2-(3-amino-1H-pyrazol-5-yl)-N-(3-fluorophenyl)acetamide used in step 50c was prepared as follows:

h) Pentafluorophenyl trifluoroacetate (11.9 g, 42.5 mmol) was added dropwise to a solution of (3-amino-1H-pyrazol-5-yl)acetic acid (3.00 g, 21.3 mmol) and pyridine (3.80 ml, 46.7 mmol) in dimethylformamide (25 ml) at 0° C. The reaction was allowed to warm to ambient temperature over 90 minutes before addition of 3-fluoroaniline (4.10 ml, 42.5 mml). The reaction was stirred for 2.5 hours at ambient temperature and then poured into 0.2 N hydrochloric acid and extracted with dichloromethane (3×50 ml). Addition of excess diethyl ether caused precipitation of 2,2,2-trifluoro-N-(5-{2-[(3-fluorophenyl)amino]-2-oxoethyl}-1H-pyrazol-3-yl)acetamide (2.08 g, 30% yield) which was isolated as a pale orange solid:

MS (+ve ESI): 331 (M+H)+.

i) A solution of 2,2,2-trifluoro-N-(5-{2-[(3-fluorophenyl)amino]-2-oxoethyl}-1H-pyrazol-3-yl)acetamide (3.10 g, 9.4 mmol) in methanol (25 ml) and 2.0N aqueous hydrochloric acid (20 ml, 40 mml) was heated at 50° C. for 2.5 hours. The reaction was cooled to ambient temperature, basified with solid sodium hydrogen carbonate and then concentrated in vacuo until a solid began to precipitate. Collection of the resultant solid by suction filtration followed by prolonged drying in vacuo yielded 2-(3-amino-1H-pyrazol-5-yl)-N-(3-fluorophenyl)acetamide (1.05 g, 48% yield) as a pale brown solid:

$^1$H-NMR (DMSO $d_6$): 11.25 (br s, 1H), 10.30 (br s 1H), 7.60 (d, 1H), 7.32 (m, 2H), 6.86 (m, 1H), 5.31 (s, 1H), 4.62 (br s, 2H), 3.48 (s, 2H).

The invention claimed is:

1. A compound, which is 2-[[3-({4-[(5-{2-[(3-fluorophenyl)amino]-2-oxoethyl}-1H-pyrazol-3-yl)amino]-quinazolin-7-yl}oxy)propyl](ethyl)amino]ethyl dihydrogen phosphate, or a pharmaceutically acceptable salt thereof.

2. A pharmaceutical composition comprising a compound according to claim 1 in association with a pharmaceutically acceptable diluent or carrier.

* * * * *

UNITED STATES PATENT AND TRADEMARK OFFICE
CERTIFICATE OF CORRECTION

| | | |
|---|---|---|
| PATENT NO. | : 7,528,121 B2 | Page 1 of 1 |
| APPLICATION NO. | : 10/539220 | |
| DATED | : May 5, 2009 | |
| INVENTOR(S) | : Heron et al. | |

It is certified that error appears in the above-identified patent and that said Letters Patent is hereby corrected as shown below:

On the Title page,

[*] Notice:    Subject to any disclaimer, the term of this patent is extended or adjusted under 35 USC 154(b) by 620 days Delete the phrase "by 620 days" and insert -- by 935 days --

Signed and Sealed this

Thirteenth Day of April, 2010

David J. Kappos
*Director of the United States Patent and Trademark Office*